United States Patent
Monck et al.

(10) Patent No.: US 11,286,298 B2
(45) Date of Patent: **\*Mar. 29, 2022**

(54) BIOPHARMACEUTICAL COMPOSITIONS

(71) Applicant: GLAXOSMITHKLINE INTELLECTUAL PROPERTY (NO. 2) LIMITED, Brentford (GB)

(72) Inventors: Myrna A. Monck, Waltham, MA (US); Narendra B. Bam, King of Prussia, PA (US); Jennifer Dally, King of Prussia, PA (US); Michelle Spatara, King of Prussia, PA (US)

(73) Assignee: GLAXOSMITHKLINE INTELLECTUAL PROPERTY (NO. 2) LIMITED, Brentford (GB)

( \* ) Notice: Subject to any disclaimer, the term of this patent is extended or adjusted under 35 U.S.C. 154(b) by 0 days.

This patent is subject to a terminal disclaimer.

(21) Appl. No.: 17/373,412

(22) Filed: Jul. 12, 2021

(65) Prior Publication Data

US 2021/0340247 A1 Nov. 4, 2021

Related U.S. Application Data

(60) Continuation of application No. 16/806,071, filed on Mar. 2, 2020, which is a division of application No. 15/754,768, filed as application No. PCT/IB2016/055012 on Aug. 22, 2016, now Pat. No. 10,870,695.

(60) Provisional application No. 62/209,000, filed on Aug. 24, 2015, provisional application No. 62/240,131, filed on Oct. 12, 2015, provisional application No. 62/247,906, filed on Oct. 29, 2015, provisional application No. 62/249,497, filed on Nov. 2, 2015.

(51) Int. Cl.
*C07K 16/24* (2006.01)
*A61P 11/06* (2006.01)
*A61P 11/02* (2006.01)

(52) U.S. Cl.
CPC ............ *C07K 16/244* (2013.01); *A61P 11/02* (2018.01); *A61P 11/06* (2018.01); *C07K 2317/24* (2013.01); *C07K 2317/40* (2013.01); *C07K 2317/90* (2013.01); *C07K 2317/94* (2013.01)

(58) Field of Classification Search
CPC .................................................. C07K 16/244
See application file for complete search history.

(56) References Cited

U.S. PATENT DOCUMENTS

| | | | |
|---|---|---|---|
| 5,683,892 A | 11/1997 | Ames, Jr. et al. |
| 5,693,323 A | 12/1997 | Ames, Jr. et al. |
| 5,783,184 A | 7/1998 | Appelbaum et al. |
| 5,851,525 A | 12/1998 | Ames, Jr. et al. |
| 5,998,586 A | 12/1999 | Bodmer et al. |
| 6,056,957 A | 5/2000 | Chou et al. |
| 6,129,913 A | 10/2000 | Ames et al. |
| 6,316,227 B1 | 11/2001 | Bodmer et al. |
| 6,451,982 B1 | 9/2002 | Chou et al. |
| 6,734,286 B2 | 5/2004 | Bodmer et al. |
| 6,946,130 B2 | 9/2005 | Ames et al. |
| 7,399,837 B2 | 7/2008 | Ames et al. |
| 7,982,005 B2 | 7/2011 | Ames et al. |
| 8,071,810 B2 | 12/2011 | Schnatbaum et al. |
| 8,652,474 B2 | 2/2014 | Harris et al. |
| 9,493,583 B2 | 11/2016 | Charvet et al. |
| 9,834,600 B2 | 12/2017 | Hargreave et al. |
| 10,870,695 B2 | 12/2020 | Monck et al. |
| 2009/0148905 A1 | 6/2009 | Ashman et al. |
| 2010/0086547 A1 | 4/2010 | Patel et al. |
| 2010/0303827 A1 | 12/2010 | Sharma, Sr. et al. |
| 2011/0020339 A1 | 1/2011 | Hargreave et al. |
| 2012/0301478 A1 | 11/2012 | Ogura et al. |
| 2014/0023655 A1 | 1/2014 | Monck et al. |
| 2014/0044717 A1 | 2/2014 | Kranz et al. |
| 2014/0044727 A1 | 2/2014 | Monck et al. |
| 2015/0210764 A1 | 7/2015 | Mondal et al. |
| 2016/0207993 A1 | 7/2016 | Ashman et al. |

FOREIGN PATENT DOCUMENTS

| | | |
|---|---|---|
| EP | 0 800 536 B1 | 11/2006 |
| EP | 2 274 009 B1 | 11/2013 |
| EP | 2 152 290 B1 | 6/2014 |
| EP | 2738172 A1 | 6/2014 |
| EP | EP 2848615 A1 | 3/2015 |
| JP | 2011-504742 | 2/2011 |
| WO | WO 97/48418 A1 | 12/1997 |
| WO | WO 98/57979 A1 | 12/1998 |
| WO | WO 2007/100902 A2 | 9/2007 |
| WO | WO 2008/134724 A2 | 11/2008 |
| WO | WO 2009/068649 A2 | 6/2009 |
| WO | WO 2009/070642 A1 | 6/2009 |
| WO | WO 2009/120927 A2 | 10/2009 |
| WO | WO 2010/073119 A1 | 7/2010 |
| WO | WO 2012/109429 A2 | 8/2012 |
| WO | WO 2012/138958 A1 | 10/2012 |
| WO | WO 2012/141978 A2 | 10/2012 |

(Continued)

OTHER PUBLICATIONS

Goswami et al., "Developments and Challenges for mAb-Based Therapeutics", Antibodies, vol. 2, No. 3, pp. 452-500 (2013).

(Continued)

*Primary Examiner* — Prema M Mertz
(74) *Attorney, Agent, or Firm* — Cynthia Lan Martin; Duke Fitch

(57) ABSTRACT

The present disclosure relates to compositions, for treating interleukin 5 (IL-5) mediated diseases, and related methods.

17 Claims, 7 Drawing Sheets
Specification includes a Sequence Listing.

(56) References Cited

FOREIGN PATENT DOCUMENTS

| WO | WO 2014/141149 A1 | 9/2014 |
| WO | WO 2014/158231 A1 | 10/2014 |
| WO | WO 2015/049519 A2 | 4/2015 |
| WO | WO 2015/112886 A2 | 7/2015 |
| WO | WO 2015/117711 A1 | 8/2015 |
| WO | WO 2016/198663 A1 | 12/2016 |

OTHER PUBLICATIONS

Taillé et al., "Mepolizumab in a population with severe eosinophilic asthma and corticosteroid dependence: results from a French early access programme", Euopean Respiratory journal, vol. 55, No. 6,1902345, pp. 1-11 (Jun. 2020).

Manali Mukherjee, et al., "anti-il5 therapy For asthma and beyond", World allergy organization journal, biomed central ltd, London, UK, vol. 7, No. 1, p. 32, Dec. 4, 2014.

Tyther Raymond, et al., "Quality Issues Arising from Post-translational Modification of Recombinant Antibodies", Jan. 1, 2011, Antibody Expression and Production, pp. 293-303.

Hui F. Liu, et al., "Recovery and purification process development for monoclonal antibody production", MABS, vol. 2, No. 5, Sep. 1, 2010 (Sep. 1, 2010), pp. 480-499.

Kang Xuezhen, et al., "Monoclonal antibody heterogeneity analysis and deamidation monitoring with high-performance cation-exchange chromatofocusing using simple, two component buffer systems", Journal of Chromatography A, vol. 1283, Jan. 31, 2013, pp. 89-97.

Andrew M. Goetze et al: "Assessing monoclonal antibody product quality attribute criticality through clinical studies", MABS, vol. 2, No. 5, Sep. 1, 2010 (Sep. 1, 2010) pp. 500-507.

Markus Haberger et al., "Assessment of chemical modifications of sites in the CDRs of recombinant antibodies", MABS, vol. 6, No. 2, Jan. 17, 2014 (Jan. 17, 2014), pp. 327-339.

Chartrain M et al., "Development and production of commercial therapeutic monoclonal antibodies in mammalian cell expression systems: An overview of the current upstream technologies", Current Pharmaceutical Biotechnology, vol. 9, No. 6, Dec. 1, 2008, pp. 447-467.

Flood, E.M., et al. "Pediatric eosinophilic esophagitis: patient/caregiver perspectives on quality of life impacts and the content validity of new symptom questionnaires". J. Pediatr. Gastroenterol. Nutr., 43(4): E25, Abtract 38 (Oct. 2006).

Rothenberg, M.E., et al. "Steroid-sparing effects of Anti-IL-5 monoclonal antibody (Mepolizumab) therapy in patients with HES: A multicenter, randomized, double-blind, placebo-controlled trial". Blood, 108: 373 (2006).

Klion, A.D., et al. "Safety and tolerability of Anti-IL-5 monoclonal antibody (Mepolizumab) therapy in patients with HES: A multi-center, randomized, double-blind, placebo-controlled trial". Blood, 108: 2694 (2006).

Weller, P.F., et al. "Effects of Mepolizumab, an anti-interleukin-5 monoclonal antibody, on blood eosinophil counts in patients with hypereosinophilic syndrome". J. Allergy Clin. Immunol., 119(1): S209, Abstract 821, (2007).

Rosenwasser, L.J., et al. "Corticosteroid-sparing effects of Mepolizumab, an Anti-Interleukin-5 monoclonal antibody, in patients with hypereosinophilic Syndrome". J. Allergy Clin. Immunol., S160, Abstract 628 (Jan. 2007).

Stein, M., et al. "Anti-IL-5 therapy (Mepolizumab) for eosinophilic esophagitis: Cytokine secretion and decreased peripheral blood and esophageal eosinophilia". Abstract Sa.60. doi:10.1016/j.clim.2006.04.292.

Parkin, X., et al. "Rationale and design of a double-blind, placebo-controlled trial to evaluate the corticosteroid-sparing effects of anti-IL5 monoclonal antibody (Mepolizumab) in subjects with hypereosinophilic syndrome". Haematologica/The Hematology Journal, 91 (S1): 36, Abstract 0095 (2006).

Shear, N., et al. "Rationale and design of a placebo-controlled trial to evaluate the steroid-sparing effects of anti-IL5 monoclonal antibody (Mepolizumab): Focus on cutaneous Outcomes in patients with hypereosinophilic syndrome (HES)". 65th Annual Meeting, JAAD, Feb. 2-6, 2007.

Shear, N., et al. "Rationale and design of a placebo-controlled trial to evaluate the steroid-sparing effects of anti-IL5 monoclonal antibody (Mepolizumab): Focus on cutaneous outcomes in patients with hypereosinophilic syndrome (HES)". J. Am. Acad. Dermatol., AB71, Abstract P716, Feb. 2007.

Stein, M.L., et al. "Humanized Anti-IL-5 therapy (Mepolizumab) reduces eosinophil responsiveness to the eotaxins". J. Allergy Clin. Immunol., 119(1): S135, Abstract 531 (2007).

Straumann, A., et al. "Mepolizumab, a humanized monoclonal antibody to IL-5, for severe Eosinophilic esophagitis in adults: A randomized, placebo-controlled double-blind trial". Gastroenterology, 132(7): 2586 (2007).

Rosenwasser, L.J., et al. "Corticosteroid-sparing effects of Mepolizumab, an anti-interleukin-5 monoclonal antibody, in patients with hypereosinophilic syndrome", 5th Biennial Symposium International Eosinophil Society, Absract, Jul. 18, 2007.

Weller, P.F., et al. "Effects of Mepolizumab, an anti-interleukin-5 monoclonal antibody on blood eosinophil counts in patients with hypereosinophilic syndrome", 5th Biennial Symposium International Eosinophil Society, Absract, Jul. 18, 2007.

Conus, S., et al. "Anti-IL-5 antibody therapy does not alter physiologic eosinophil infiltration of the duodenal mucosa", 5th Biennial Symposium International Eosinophil Society, Absract, Jul. 18, 2007.

Straumann, A., et al. "Mepolizumab, a humanized monoclonal antibody to IL-5, for severe eosinophilic esophagitis in adults: A randomized, placebo-controlled double-blind trial", 15th annual United European Gastroenterology Week (UEGW), Abstract, Oct. 27, 2007.

Straumann, A., et al. "Mepolizumab, a humanized monoclonal antibody to IL-5, for severe eosinophilic esophagitis in adults: A randomized, placebo-controlled double-blind trial", 5th Biennial Symposium International Eosinophil Society, Absract, Jul. 18, 2007.

Georgelas, A., et al. "Mepolizumab (humanized anti-IL-5 Mab) treatment of the hypereosinophilic syndrome reduces serum levels of the eosinophil-derived neurotoxin", 5th Biennial Symposium International Eosinophil Society, Absract, Jul. 18, 2007.

Florence Roufosse. "Hypereosinophilic syndrome and its treatment". EURODIS (2007) European Organisation for Rare Diseases—4th European Conference on Rare Diseases, Abstract, Nov. 27, 2007.

Stein, M.L., et al. "Increased high molecular weight IL-5 complex after anti-IL-5 (Mepolizumab) therapy". J. Allergy Clin. Immunol., S118, Abstract 454, Feb. 2008.

Tofts. "IL-5 directed approaches (in the treatment of eosinophil-driven disease)". New Drugs and Targets for Asthma and COPD, National Heart & Lung Institute, London, Abstract, Nov. 21, 2007.

Gevaert, P., et al. "Mepolizumab, a humanised Anti-IL-5 monoclonal antibody, as treatment of severe nasal polyposis". J. Allergy Clin. Immunol., 121(3): 797, Abstract LB26 (2008).

Straumann, A., et al. "Mepolizumab, a humanized monoclonal antibody to IL-5, for severe eosinophilic esophagitis in adults: A randomized, placebo-controlled double-blind trial". J. Allergy Clin. Immunol., S44, Abstract 171, Feb. 2008.

Nair, P., et al. "Prednisone-sparing effect of mepolizumab on eosinophilic bronchitis with or without asthma: a randomized, placebo-controlled trial". American Thoracic Society, Abstract 952307 (2008).

Kim, S.H., et al. "Mepolizumab as a steroid-sparing treatment in the Churg Strauss Syndrome". Am. J. Respir. Grit. Care. Med., 179: A5468 (2009).

Haldar, P., et al. "Mepolizumab (Anti-IL5) and exacerbation frequency in refractory eosinophilic asthma". Am. J. Respir. Grit. Care Med., 179: A3638 (2009).

Gupta, S., et al. "CT assessment of changes in airway dimensions with Mepolizumab treatment in refractory eosinophilic asthma". Am. J. Respir. Grit. Care. Med., 179: A3641 (2009).

(56) References Cited

OTHER PUBLICATIONS

Miller, L.A., et al. "Anti-IL-5 treatment attenuates the asthma phenotype in infant monkeys, but also affects normal lung development". Am. J. Respir. Grit. Care Med., 179: A2209 (2009).
Thomson, M., et al. "Safety and pharmacodynamics of mepolizumab, a humanised monoclonal antibody against IL-5, in paediatric subjects with eosinophilic oesophagitis: a randomised, double-blind, controlled clinical trial", Abstract, United European Gastroenterology Week (UEGW), Nov. 21, 2009.
Gupta, S., et al. "PK and PD of Mepolizumab in pediatric subjects with eosinophilic esophagitis: A randomized, double-blind, controlled clinical trial". J. Pediatr. Gastroenterol. Nutr., 49(Supp.1): E65 (2009).
Aceves, S., et al., "Clinical characteristics of pediatric eosinophilic esophagitis subjects with inadequate response to or intolerance of prior therapies receiving Mepolizumab in a multicenter clinical trial". J. Allergy Clin. Immunol., 125(2): AB159, Abstract 626 (2010).
Gupta, S., et al. "Utility of eosinophil-derived neurotoxin as a biomarker in eosinophilic esophagitis: Results from a randomized, double-blind, controlled trial of Mepolizumab in pediatric patients". J. Allergy Clin. Immunol., AB234, Abstract 915, Feb. 2010.
Assa'ad, A., et al. "Utility of eosinophil-derived neurotoxin as a biomarker in eosinophilic esophagitis: Results from a randomized, double-blind, controlled trial of Mepolizumab in pediatric patients". J. Allergy Clin. Immunol., 125(2): AB129, Abstract 510 (2010).
Collins, M.H., et al. "Effect of a monoclonal antibody (Mepolizumab) against Interleukin-5 (IL-5) in reducing eosinophilic inflammation in children with eosinophilic esophagitis (EoE)". Society for Pediatric Pathology, Spring Meeting, Washington, DC. Mar. 20-21, 2010.
Moosig, F., et al. "Mepolizumab, a humanized Anti-IL-5 antibody, has steroid-sparing potential in Churg-Strauss Syndrome". ACR, S925, Abstract 2203, (2010).
Abberley, L., et al. "The validation of a method for the analysis of Mepolizumab using the Gyros Platform". EAS Abstracts, p. 5, Abstract 23 (Nov. 2010).
Pavord, I., et al. "Mepolizumab (anti-IL-5) reduces exacerbations in patients with refractory eosinophilic asthma". European Respiratory Society 2012 Annual Conference, Abstract, Sep. 1, 2012.
Klion, A.D., et al. "Long-term Safety and Efficacy of Mepolizumab for the Treatment of Hypereosinophilic Syndrome". J. Allergy Clin. Immunol., 129(2): AB203, Abstract 766 (2012).
Otani, I.M., et al. "The effect of Anti-IL-5 therapy on esophageal mastocytosis in pediatric eosinophilic esophagitis". J. Allergy Clin. Immunol., AB202, Abstract 763 (2012).
Ortega, H.G., et al. "The role of Mepolizumab in atopic and non-atopic patients with refractory eosinophilic asthma". Am. J. Respir. Grit. Care Med., 187: A3861 (2013).
Ortega, H., et al. "Blood eosinophil count is a useful biomarker to identify patients with severe eosinophilic asthma". European Respiratory Journal, 42: P855 (2013).
Philipson, R.S., et al. "Mepolizumab in the treatment of eosinophilic granulomatosis with polyangiitis". EULAR, European League Against Rheumatism 2014, Abstract, Jun. 11, 2014.
Zeiger, R.S., et al. "Characteristics and outcomes of severe uncontrolled asthma (sua) in a large managed care organization". Am. J. Respir. Grit. Care Med., 191: A6280 (2015).
Lefebvre, P., et al. "Economic and clinical burden of acute and chronic systemic corticosteroid-related complications in asthma patients". Am. J. Respir. Grit. Care Med., 191: A4161 (2015).
Suruki, R.Y., et al. "Exacerbation frequency and risk for subsequent exacerbation in adolescents and adults with asthma". Am. J. Respir. Grit. Care Med., 191: A1701 (2015).
Chastek, B., et al. "The few who use the most: Costs of severe and persistent asthma in a US managed care plan". Am. J. Respir. Grit. Care Med., 191: A4164 (2015).
Suruki, R.Y., et al. "Exacerbation frequency among pediatric patients with asthma in a US healthcare claims database". Am. J. Respir. Grit. Care Med., 183: A3751 (2011).

Suruki, R.Y., et al. "Description and frequency of exacerbations in a 12-month period among pediatric patients with asthma in the United Kingdom (UK) primary care setting". Am. J. Respir. Grit. Care Med., 183: A3750 (2011).
Ortega, H., et al. "Late-breaking abstract: Reduction in exacerbations with mepolizumab in severe eosinophilic asthma: MENSA study". European Respiratory Journal, 44: 2906 (2014).
Bel, E.H., et al. "Late-breaking abstract: Oral corticosteroid-sparing effect of mepolizumab in severe eosinophilic asthma: the SIRIUS study". European Respiratory Journal, 44: 2907 (2014).
Engelkes, M., et al. "Late-breaking abstract: Multinational, database cohort study to assess severe exacerbation rate in asthma". European Respiratory Journal, 46: PA4082 (2015).
Ortega, H., et al. "Response to treatment with mepolizumab in elderly patients". Am. J. Respir. Grit. Care Med., 191: A4177 (2015).
Albers, F.C., et al. "Effect of mepolizumab in severe eosinophilic asthma patients with history of omalizumab treatment". J. Allergy Clin. Immunol., 135 (2), AB383, Abstract L7, (2015).
Forshag, M., et al. "Healthcare resource use associated with exacerbations in patients with severe eosinophilic asthma". Am. J. Grit. Care Med., 191: A4174 (2015).
Prazma, C.M., et al. "Effect of mepolizumab in OCS dependent severe eosinophilic asthma patients with history of omalizumab treatment". J. Allergy Clin. Immunol., 135(2), AB383, Abstract L6 (2015).
Prazma, C.M., et al. "The impact of duration of oral corticosteroid use on co-morbidities in a severe asthma population treated with mepolizumab". Am. J. Respir. Grit. Care Med., 191: A4279 (2015).
Pavord, I., et al. "A meta-analysis of exacerbations requiring hospitalization from studies of mepolizumab in severe eosinophilic asthma". Am. J. Respir. Grit. Care Med., 191: A4260 (2015).
Duncan, E.A., et al. "Observational experience describing the use of mepolizumab in patients with hypereosinophilic syndrome". Am. J. Respir. Grit. Care Med., 191: A1365 (2015).
Shimoda, T., et al. "Efficacy and safety of Mepolizumab in patients with eosinophilic severe asthma: Phase III, Japanese subgroup analysis". JRS (2016)—English translation.
Shimoda, T., et al. "Efficacy and safety of Mepolizumab in patients with eosinophilic severe asthma: Phase III, Japanese subgroup analysis". JRS (2016)—in Japanese. (English translation provided above (in C105).
Suruki, R., et al. "Occurrence and reoccurrence of asthma—related and all-cause emergency department (ED)/hospitalization events". Chest, 148(4—Meeting Abstracts):10A (2015).
Engelkes, M., et al. "Late-breaking abstract: Multinational, database cohort study to assess all-cause mortality following severe asthma exacerbations". European Respiratory Journal, 46: PA4083 (2015).
Idzko, M., et al. "Effect of mepolizumab in severe eosinophilic asthma patients (subgroup analyses comparing European Union to non EU)". Pneumologie, 70:432 (2016). English translation.
Idzko, M., et al. "Wirkung von Mepolizumab bei patienten mit schwerem eosinophilem asthma (subgruppenanalyse der europaischen union im vergleich zu nicht EU landern)". Pneumologie, 70:432 (2016). In German. (English translation provided in C109).
Suruki, R.Y., et al. "The identification and description of severe asthma patients in a cross-sectional study the ideal study". J. Allergy Clin. Immunol., 137(2), AB103, Abstract 335 (2016).
Nelsen, L.M., Characterization of a severe asthma patient population with and without eosinophilic inflammation and frequent exacerbations by multiple pros (ideal). Am. J. Respir. Grit. Care Med., 193: A4330 (2016).
Albers, F., et al. "Effect of mepolizumab in patients with severe eosinophilic asthma receiving different levels of standard of care". Canadian Respiratory Conference, Abstract 37, Apr. 14, 2016.
McDonald, V., et al. "The relationship between patient and clinician rated response to therapy relative to ACQ-5 scores and exacerbation rates in severe eosinophilic asthma (SEA)". The Thoracic Society of Australian & New Zealand (TSANZ) 2016 Annual Scientific Meeting, Abstract, Apr. 1, 2016.
Albers, F.C., et al. "Effect of mepolizumab in severe eosinophilic asthma patients in relation to their baseline ACQ-5 and SGRQ scores". Allergy, 71 (Suppl.102): 118-272, Abstract 553 (2016).

(56) References Cited

OTHER PUBLICATIONS

Nelson, L., et al., "Quantitative validity of the Sgrq in patients with severe asthma". J. Allergy Clin. Immunol., AB204, Abstract 666 (2016).
Suruki, R.Y., et al. "Evaluation of exacerbation frequency and re-hospitalization, and risk for subsequent exacerbations in asthma patients in a UK primary care setting", British Thoracic Society Winter Meeting, Abstract, Dec. 2, 2015.
Suruki, R.Y., et al. "Evaluation of exacerbation frequency and re-hospitalization, and risk for subsequent exacerbations in asthma patients in a UK primary care setting". Thorax, 70(Suppl.3): A188, Abstract P221 (2015).
Cockle, S., et al. "Impact of asthma exacerbations on health status in patients with severe asthma". J. Allergy Clin. Immunol., AB8, Abstract 23 (2016).
Albers, F., et al. "Effect of mepolizumab (MEPO) in patients with severe eosinophilic asthma (ESA) previously treated with omalizumab (OMA)". 20$^{th}$ Congress, CPLF Jan. 2016. English translation.
Albers, F., et al. "Effet du mepolizumab (MEPO) chez des patients atteints d'asthme severe eosinophilique (ASE) precedemment traits par omalizumab (OMA)". Revue des Maladies Respiratoires vol. 33, Supplement, Jan. 2016, p. A30, Abstract presented at Congres de Pneumologie de Langue Frangaise (CPLF). In French. (See English translation in C120).
Prazma, C., et al. "Effect of Mepolizumab (MEPO) in patients with severe eosinophilic asthma (ESA), corticosteroid-related and previously treated with omalizumab (OMA)". CPLF (2015) English.
Prazma, C., et al. "Effet du Mepolizumab (MEPO) chex des patients atteints d'asthme severe eosinophilique (ASE), corticodependants et precedemment traits par Omalizumab (OMA)". CPLF (2015). In French. (See English translation in C122).
Albers, F.C., et al. "Long-term safety and efficacy of mepolizumab in patients with severe eosinophilic asthma". J. Allergy Clin. Immunol., ABM, Abstract 43 (2016).
Prazma, C.M., et al. "Steroid sparing response with Mepolizumab: durability of steroid reduction in severe asthma". J. Allergy Clin. Immunol., AB16, Abstract 49 (2016).
Stynes, G., et al. "Comparative effectiveness of Mepolizumab and Omalizumab in severe asthma: An indirect comparison". J. Allergy Clin. Immunol., AB82, Abstract 271 (2016).
Kovacs, N.C., et al. "Patient-reported symptoms from a diverse group of subjects with hypereosinophilic syndrome". J. Allergy Clin. Immunol., 137(2), AB167, Abstract 548 (2016).
Yancey, S.W., et al. "Exacerbation reduction in severe eosinophilic asthma based on eosinophil thresholds". J. Allergy Clin. Immunol., AB208, Abstract 677 (2016).
Albers, F.C., et al. "Effect of mepolizumab in severe eosinophilic asthma patients eligible for omalizumab treatment". Am. J. Respir. Grit. Care Med., 193: A6470 (2016).
Suruki, R., et al. "Evaluation of Us subjects in the identification and description of severe asthma patients in a cross-sectional study—the ideal study". Am. J. Respir. Grit. Care Med., 193:A1730 (2016).
Verhamme, K., et al. "Risk factors of severe asthma exacerbations: A real world study". Am. J. Respir. Grit. Care Med., 193: A1712 (2016).
Austin, D., et al. "A blood eosinophil count of greater than 150 cells/ul predicts sputum eosinophilia ≥ 3% in patients with severe asthma with other markers of inflammatory lung disease". Am. J. Respir. Grit. Care Med., 193: A4338 (2016).
Suruki, R., et al. "Prevalence of severe eosinophilic asthma in pediatric asthma patients identified in a US healthcare claims database". Am. J. Respir. Grit. Care Med., 193: A1731 (2016).
Bradford, E., et al. "Burden of disease in severe asthma mepolizumab population stratified by blood eosinophil count". Am. J. Respir. Grit. Care Med., 193: A6471 (2016).
Albers, F.C., et al. "Evaluation of patients with severe asthma eligible for treatment with mepolizumab or omalizumab, according to EU criteria". Allergy, 71(Supp. 102): 540, Abstract 1191 (2016).
Forshag, M., et al. "Healthcare Resource Use Associated with Exacerbations in Patients with Severe Eosinophilic Asthma". SIAAIC (2016) English translation.
Forshag, M., et al. "Risorse sanitarie impiegate per le esacerbazioni in pazienti con Asma Grave Eosinofilica". SIAAIC (2016). In Italian. (see C136 and C137 for English translations).
Nelson, L.M., et al. "Qualitative evidence of content validity of the SGRQ in patients with severe asthma". Allergy, 71 (Suppl. 102): 538, Abstract 1185 (2016).
Albers, F.C., et al. "Efficacy of mepolizumab in reducing exacerbations in patients with severe eosinophilic asthma who would be eligible for omalizumab treatment". Allergy, 71 (Suppl. 102): 66, Abstract 131 (2016).
NCT02377427, Feb. 26, 2015.
NCT02377427, Jul. 30, 2015.
NCT01842607, Apr. 25, 2013.
NCT01842607, Aug. 20, 2015.
NCT01691859, Sep. 20, 2012.
NCT01691859, Jul. 23, 2015.
NCT02135692, May 8, 2014.
NCT02135692, Aug. 20, 2015.
NCT02654145, Jan. 11, 2016.
NCT02555371, Sep. 17, 2015.
NCT02594332, Nov. 2, 2015.
NCT01520051, Jan. 25, 2012.
NCT01520051, Feb. 6, 2012.
NCT02020889, Dec. 19, 2013.
NCT02020889, Jul. 23, 2015.
NCT01463644, Nov. 1, 2011.
NCT01463644, Feb. 19, 2015.
NCT02836496, Jul. 14, 2016.
NCT01691508, Sep. 20, 2012.
NCT01691508, Jun. 4, 2015.
NCT02281318, Oct. 30, 2014.
NCT02281318, Aug. 20, 2015.
NCT01691521, Sep. 20, 2012.
NCT01691521, Jul. 30, 2015.
NCT02105948, Apr. 3, 2014.
NCT02105948, Aug. 6, 2015.
NCT02105961, Apr. 3, 2014.
NCT02105961, Aug. 20, 2015.
NCT01471327, Nov. 10, 2011.
NCT01471327, Jun. 6, 2013.
NCT01705795, Oct. 11, 2012.
NCT01705795, Jul. 9, 2015.
NCT02293265, Nov. 13, 2014.
NCT02293265, Aug. 13, 2015.
NCT02559791, Sep. 23, 2015.
Brorson, K., et al. "Therapeutic monoclonal antibodies and consistent ends: terminal heterogeneity, detection, and impact on quality". Current Opinion in Biotechnology, 30: 140-146 (2014).
Esnault, S., et al. "Human eosinophils release IL-1β and increase expression of IL-17A in activated CD4+ T lymphocytes". Clin. Exp. Allergy, 42(12): 1756-1764 (Dec. 2012).
Esnault, S., et al. "Identification of genes expressed by human airway eosinophils after an in vivo allergen challenge". PLOS One, 8(7): e67560, pp. 1-9 (Jul. 2013).
Goetze, A., et al. "Assessing monoclonal antibody product quality attribute criticality through clinical studies". mAbs, 2(5): 500-507 (Sep./Oct. 2010).
Johansson, M.W., et al. "Anti-IL-5 attenuates activation and surface density of β$_2$-integrins on circulating eosinophils after segmental antigen challenge". Clinical & Experimental Allergy, 43:292-303 (2012).
Liu, H., et al. "Effect of posttranslational modifications on the thermal stability of a recombinant monoclonal antibody". Immunology Letters, 106: 144-153 (2006).
Liu, H., et al. "Disulfide bond structures of IgG molecules". mAbs, 4(1): 17-23 (2012).
Kunert, R., et al. "Advances in recombinant antibody manufacturing". Appl. Microbiol. Biotechnol., 100: 3451-3461 (2016).

(56) References Cited

OTHER PUBLICATIONS

Smith, D., et al. "Pharmacokinetics and pharmacodynamics of Mepolizumab, an Anti-Interleukin-5 monoclonal antibody". Clin. Pharmacokinet., 50(4): 215-227 (2011).
Vidarsson, G., et al. "IgG subclasses and allotypes: from structure to effector functions". Frontiers in Immunology, 5: 1-17 (Oct. 2014). Doi: 10.3389/fimmu.2014.00520.
Zauner, G., et al. "Glycoproteomic analysis of antibodies". Molecular & Cellular Proteomics, 12: 10.1074/mcp.R112.026005, 856-865 (2013).
Press Release. "GSK receives European marketing authorization for Nucala® (mepolizumab) in 31 countries". Dec. 2, 2015.
Press Release. "GSK presents new data on the long-term efficacy & safety of Nucala® for the treatment of severe asthma with an eosinophilic phenotype." Mar. 5, 2016.
Press Release. "GSK announces outcome of US FDA Advisory Committee recommending approval of mepolizumab for the treatment of adults with severe asthma". Jun. 11, 2015.
Press Release. "GSK announces start of Phase III study for mepolizumab in patients with Eosinophilic Granulomatosis with Polyangiitis". Feb. 14, 2014.
Press Release. "Regulatory update: mepolizumab for the treatment of hypereosinophilic syndrome (HES)". Jul. 28, 2009.
Press Release. "GSK receives marketing authorization for Nucala® (mepolizumab) in Japan". Mar. 29, 2016.
Press Release. "GSK receives positive CHMP opinion in Europe for novel anti-IL5 biological Nucala (mepolizumab) for the treatment of patients with severe refractory eosinophilic asthma". Sep. 24, 2015.
Press Release. "GSK's Nucala® (mepolizumab) receives approval from US FDA". Nov. 4, 2015.
Zhang, et al. "MFI on sub-visible particle quantification, an assay precision study". American Association of Pharmaceutical Scientists, National Biotechnology Conference, San Diego, CA, Poster, May 21, 2012.
Varma, et al. "Evaluation of high concentration liguid formulations of a monoclonal antibody in various containers", 2012 Workshop on Protein Aggregation and Immunogenicity, Breckenridge, CO, Poster, Jul. 9, 2012.
Farhat Syed. "Personalised medicine—an industry perspective", Annual Maastricht Symposium on Global and European Health, Maastricht, Netherlands, Oral Presentation, Oct. 10, 2013.
Varma, et al. "Evaluation of high concentration liquid formulations (up to 200 mg/ml) of a monoclonal antibody in glass and plastic syringes", 2014 Parenteral Drug Association, Universe of Pre-filled syringes, Oral Presentation, Oct. 6, 2014.
Levy, N.E., et al. "Development and characterization of a protein A capture step for improved impurity clearance", 2015 American Chemical Society National Meeting, Division of Biochemical Technology, Denver, CO, Poster, Mar. 22, 2015.
Badalaty, L., et al. "A high throughput approach to hydrophobic interaction chromatography step development for multiple distinct therapeutic biopharmaceuticals", 28th International Symposium, Exhibit, & Workshops on Preparative and Process Chromatography, Philadelphia, PA, Poster, Jul. 26, 2015.
Rothenberg, M.E., et al. "Steroid-sparing effects of anti-IL-5 monoclonal antibody (mepolizumab) therapy in patients with HES: a multicenter, randomized, double-blind, placebo-controlled trial". American Society of Hematology, 48th Annual Meeting, Oral Presentation, Dec. 9, 2006.
Multi-centre clinical trial: Intravenous mepolizumab in children with eosinophilic esophagitis. Clinical Trials.gov, NCT00358449, first posted Jul. 31, 2006, update Mar. 15, 2012.
Straumann, A., et al. "A randomized, placebo-controlled, double-blind trial of mepolizumab (Anti-IL-5) for the treatment of severe eosinophilic esophagitis in adults". Digestive Disease Week, Chicago, IL, Oral Presentation, May 4, 2009.
Gupta, S., et al. "Pharmacokinetics and pharmacodynamics of mepolizumab in pediatric subjects with eosinophilic esophagitis: a randomized, double-blind, controlled clinical trial". North American Society for Pediatric Gastroenterology, Hepatology & Nutrition, Oral Presentation, Oct. 1, 2009.
Thomson, M., et al. "Safety and pharmacodynamics of mepolizumab, a humanized monoclonal antibody against IL-5, in paediatric subjects with eosinophilic oesophagitis: a randomized, double-blind, controlled clinical trial", United European Gastroenterology Week, London, United Kingdon, Oral Presentation, Nov. 21, 2009.
Gupta, S., et al. "Utility of eosinophil-derived neurotoxin as a biomarker in eosinophilic esophagitis: results from a randomized, double-blind, controlled trial of mepolizumab in pediatric patients". American Academy of Allergy, Asthma & Immunology, Oral Presentation, Feb. 25, 2010.
Collins, M.H., et al. Effect of a monoclonal antibody (mepolizumab) against interleukin-5 (IL-5) in reducing eosinophilic inflammation in children with eosinophilic esophagitis (EE), Society for Pediatric Pathology—2010 Spring Meeting, Oral Presentation, Mar. 20, 2010.
Moosig, F., et al. "Targeting IL-5 in refractory/relapsing Churg-Strauss Syndrome", 2010 Annual Scientific Meeting of the American College of Rheumatology, Atlanta, GA, Oral Presentation, Nov. 7, 2010.
Suruki, R.Y., et al. "Description and frequency of exacerbations in a 12-month period among pediatric patients with asthma in the United Kingdom (UK) primary care setting". American Thoracic Society International Meeting, Denver, CO. (May 16, 2011).
Roufosse, F.E., et al. "Long-term safety of mepolizumab for the treatment of hypereosinophilic syndrome", American Academy of Allergy, Asthma & Immunology, Oral Presentation, Mar. 2, 2012.
Richard Philipson. "Mepolizumab in Churg-Strauss Syndrome", EUVAS (2012) European Vasculitis Study Group, Oral Presentation, Jun. 4, 2012.
Pavord, I., et al. "Mepolizumab (anti-IL-5) reduces exacerbations in patients with refractory eosinophilic asthma". European Respiratory Socient, Vienna, Austria, Oral Presentation, Sep. 2, 2012.
Suruki, R.Y., et al. "Exacerbation frequency among pediatric patients with asthma in a U.S. Healthcare claims database". American Thoracic Society, Oral Presentation, May 13, 2011.
Suruki, R.Y., et al. "Description and Frequency of Exacerbations in a 12-month Period Among Pediatric Patients with Asthma in the United Kingdom (UK) Primary Care Setting", American Thoracic Society, Oral Presentation, May 13, 2011.
S.J. Pascoe. "An Industry View of Future Developments in Pharmacotherapy in Obstructive Lung Disease", Canadian Thoracic Society Respiratory Conference, Oral Presentation, Apr. 24, 2014.
Ortega, H.G., et al. "Reduction in Exacerbations with Mepolizumab in Severe Eosinophilic Asthma". European Respiratory Society Congress, Munich, Germany, Sep. 6, 2014.
Bel, E.H., et al. "Oral corticosteroid-sparing effect of mepolizumab in severe eosinophilic asthma". European Respiratory Society Congress, Munich, Germany, Sep. 6, 2014.
Hector Ortega. "Predictors of Treatment Response in Eosinophilic Diseases", International Eosinophil Society, Oral Presentation, Chicago, IL, Jul. 14, 2015.
Oliver Keene. "Estimands in Confirmatory Trials: Time to Face De Facto", PSI (2016) Statisticians in the Pharmaceutical Industry—39th Annual Conference, Oral Presentation, May 22, 2016.
Albers, F.C., et al. "Efficacy of mepolizumab in reducing exacerbations in patients with severe eosinophilic asthma who would be eligible for omalizumab treatment". European Academy of Allergy and Clinical Immunology Congress, Vienna, Austria, Oral Presentation, Jun. 16, 2016.
Nagasaki, T., et al. "Prevalence of severe eosinophilic asthma and asthma exacerbations". The 65th Annual Meeting of the Japanese Society of Allergology, Jun. 17, 2016. (English).
Nagasaki, T., et al. "Prevalence of severe eosinophilic asthma and asthma exacerbations". The 65th Annual Meeting of the Japanese Society of Allergology, Jun. 17, 2016. (Japanese).
Wang Wet Al: "Antibody Structure, Instability, and formulation", Journal of Pharmaceutical Sciences, American Chemical Society and American Pharmaceutical Association, US, vol. 96, No. 1, Jan. 1, 2007 (Jan. 1, 2007), pp. 1-26.

BIOPHARMACEUTICAL COMPOSITIONS

FIELD OF THE DISCLOSURE

The present disclosure relates to compositions, for treating interleukin 5 (IL-5) mediated diseases, and related methods.

BACKGROUND OF THE DISCLOSURE

IL-5 plays a role in a number of different diseases such as asthma, severe eosinophilic asthma, severe asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid and eosinophilic esophagitis. These serious diseases affect hundreds of millions of people world wide.

Mepolizumab is a monoclonal antibody that binds to soluble IL-5 and blocks the soluble IL-5 from binding to its receptor. The structure of IL-5 is indicative of a secreted protein and there is no evidence of any membrane-bound forms of IL-5 on any cell types. Thus, Fc effector functions are not part of the mepolizumab mechanism of action. Based on the mechanism of action and pharmacokinetic properties of mepolizumab, there are two functional domains involved in the biological activity of this monoclonal antibody. These are a) binding to IL-5 in complementary determining region (CDR) which provides the mechanism of action; and b) binding to neonatal Fc receptor (FcRn) receptor in Fc region, which determines the half-life. Through extensive characterization studies performed throughout the development of the product, it has been determined that deamidation, oxidation, and aggregation are critical quality attributes of mepolizumab. Importantly, it has been found that specific levels of these variants must be maintained to ensure appropriate biological function.

Thus, a need exists for compositions suitable for maintaining the biological function of mepolizumab and for treating IL-5 mediated disease. Such compositions and related methods are provided by the present disclosure.

SUMMARY OF THE DISCLOSURE

One aspect of the disclosure is a composition comprising an antibody having a heavy chain amino acid sequence as shown in SEQ ID NO: 1 and a light chain amino acid sequence as shown in SEQ ID NO: 2, or an antibody variant having a heavy chain amino acid sequence at least 90% identical to the heavy chain amino acid sequence and/or a light chain amino acid sequence at least 90% identical to the light chain amino acid sequence, wherein the composition comprises: ≤80% acidic antibody variants.

Another aspect of the disclosure is a composition comprising an antibody having a heavy chain amino acid sequence as shown in SEQ ID NO: 1 and a light chain amino acid sequence as shown in SEQ ID NO: 2, or an antibody variant having a heavy chain amino acid sequence at least 90% identical to the heavy chain amino acid sequence and/or a light chain amino acid sequence at least 90% identical to the light chain amino acid sequence, wherein the composition comprises: ≤80% acidic antibody variants and ≤20% aggregated antibody variants.

Another aspect of the disclosure is a composition comprising an antibody having a heavy chain amino acid sequence as shown in SEQ ID NO: 1 and a light chain amino acid sequence as shown in SEQ ID NO: 2, or an antibody variant having a heavy chain amino acid sequence at least 90% identical to the heavy chain amino acid sequence and/or a light chain amino acid sequence at least 90% identical to the light chain amino acid sequence, wherein the composition comprises: ≤25% deamidated antibody variant at N31 of the light chain amino acid sequence; and ≤20% aggregated antibody variants.

Another aspect of the disclosure is a composition comprising an antibody having a heavy chain amino acid sequence as shown in SEQ ID NO: 1 and a light chain amino acid sequence as shown in SEQ ID NO: 2, or an antibody variant having a heavy chain amino acid sequence at least 90% identical to the heavy chain amino acid sequence and/or a light chain amino acid sequence at least 90% identical to the light chain amino acid sequence, wherein the composition comprises: ≤25% deamidated antibody variants at N31 of the light chain amino acid sequence; ≤55% oxidised antibody variants at M64 of the heavy chain amino acid sequence; ≤3% oxidised variant at W52 of the heavy chain amino acid sequence; and ≤20% aggregated antibody variants.

Another aspect of the disclosure is a composition comprising an antibody having a heavy chain amino acid sequence as shown in SEQ ID NO: 1 and a light chain amino acid sequence as shown in SEQ ID NO: 2, or an antibody variant having a heavy chain amino acid sequence at least 90% identical to the heavy chain amino acid sequence and/or a light chain amino acid sequence at least 90% identical to the light chain amino acid sequence, wherein the composition comprises: ≤25% deamidated antibody variants at N31 of the light chain amino acid sequence; ≤35% deamidated antibody variants at N386 of the heavy chain amino acid sequence; and ≤20% aggregated antibody variants.

Another aspect of the disclosure is a composition comprising an antibody having a heavy chain amino acid sequence as shown in SEQ ID NO: 1 and a light chain amino acid sequence as shown in SEQ ID NO: 2, or an antibody variant having a heavy chain amino acid sequence at least 90% identical to the heavy chain amino acid sequence and/or a light chain amino acid sequence at least 90% identical to the light chain amino acid sequence, wherein the composition comprises: ≤25% deamidated antibody variants at N31 of the light chain amino acid sequence; ≤35% deamidated antibody variants at N386 of the heavy chain amino acid sequence; ≤55% oxidised antibody variants at M64 of the heavy chain amino acid sequence, M254 of the heavy chain amino acid sequence, M430 of the heavy chain amino acid sequence; ≤3% oxidised antibody variants at W52 of the heavy chain amino acid sequence; and ≤20% aggregated antibody variants.

Another aspect of the disclosure is a composition comprising a purified preparation of a monoclonal antibody and a buffering agent, wherein the composition is at a pH from 6.8 to 7.2, wherein the buffering agent is histidine, phosphate, citric acid, citrate or a salt thereof, wherein the purified preparation comprises the isoforms represented by peak 65, peak 78, peak 88, peak 92, the main peak and peak 112 shown in FIG. 1, wherein the antibody comprises a heavy chain amino acid sequence having at least 90% identity to the amino acid sequence of SEQ ID NO: 1 and a light chain amino acid sequence having at least 90% identity to the amino acid sequence of SEQ ID NO: 2, and wherein the antibody is produced by a Chinese Hamster Ovary cell.

Another aspect of the disclosure is a composition comprising a purified preparation of a monoclonal antibody and a buffering agent, wherein the composition is at a pH from 6.8 to 7.2, wherein the buffering agent is phosphate or a salt thereof, wherein the purified preparation comprises the isoforms represented by peak 65, peak 78, peak 88, peak 92, the main peak and peak 112 shown in FIG. 1, wherein the antibody comprises a heavy chain amino acid sequence having at least 90% identity to the amino acid sequence of SEQ ID NO: 1 and a light chain amino acid sequence having at least 90% identity to the amino acid sequence of SEQ ID NO: 2, and wherein the antibody is produced by a Chinese Hamster Ovary cell.

Another aspect of the disclosure is a composition comprising a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2; and b) a main form of the antibody comprising greater than, or equal to, 50% of the protein in the composition as measured using capillary isoelectric focusing of the composition.

Another aspect of the disclosure is a composition comprising a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2; b) a main form of the antibody comprising greater than, or equal to, 50% of the protein in the composition as measured using capillary isoelectric focusing of the composition; and c) acidic forms of the antibody comprising about 20% to about 45% of the protein in the composition as measured using capillary isoelectric focusing of the composition.

Another aspect of the disclosure is a composition comprising a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2; b) a main form of the antibody comprising greater than, or equal to, 50% of the protein in the composition as measured using capillary isoelectric focusing of the composition; and c) a basic form of the antibody comprising about 1% to about 15% of the protein in the composition as measured using capillary isoelectric focusing of the composition.

Another aspect of the disclosure is a composition comprising a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2; b) a main form of the antibody comprising greater than, or equal to, 50% of the protein in the composition as measured using capillary isoelectric focusing of the composition; c) acidic forms of the antibody comprising about 20% to about 45% of the protein in the composition as measured using capillary isoelectric focusing of the composition; and d) a basic form of the antibody comprising about 1% to about 15% of the protein in the composition as measured using capillary isoelectric focusing of the composition.

Another aspect of the disclosure is a composition comprising a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2; and b) deamidated forms of the antibody comprising at least one selected from the group consisting of a heavy chain amino acid residue deamidated at asparagine 299, a heavy chain amino acid residue deamidated at asparagine 317, a heavy chain amino acid residue deamidated at asparagine 386 and a light chain amino acid residue deamidated at asparagine 31.

Another aspect of the disclosure is a composition comprising a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2; and b) oxidized forms of the antibody comprising at least one selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and light chain amino acid residue oxidized at cysteine 220.

Another aspect of the disclosure is a composition comprising a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2; b) deamidated forms of the antibody comprising at least one selected from the group consisting of a heavy chain amino acid residue deamidated at asparagine 299, a heavy chain amino acid residue deamidated at asparagine 317, a heavy chain amino acid residue deamidated at asparagine 386 and a light chain amino acid residue deamidated at asparagine 31; and c) oxidized forms of the antibody comprising at least one selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and light chain amino acid residue oxidized at cysteine 220.

Another aspect of the disclosure is a composition comprising a) an anti-IL-5 antibody comprising a heavy chain variable region having the CDRH1 amino acid sequence shown in SEQ ID NO: 5, the CDRH2 amino acid sequence shown in SEQ ID NO: 6, and the CDRH3 amino acid sequence shown in SEQ ID NO: 7; and a light chain variable region having the CDRL1 amino acid sequence shown in SEQ ID NO: 8, the CDRL2 amino acid sequence shown in SEQ ID NO: 9, and the CDRL3 amino acid sequence shown in SEQ ID NO: 10; and b) deamidated forms of the antibody comprising a light chain amino acid residue deamidated at asparagine 31.

Another aspect of the disclosure is a composition comprising a) an anti-IL-5 antibody comprising a heavy chain variable region having the CDRH1 amino acid sequence shown in SEQ ID NO: 5, the CDRH2 amino acid sequence shown in SEQ ID NO: 6, and the CDRH3 amino acid sequence shown in SEQ ID NO: 7; and a light chain variable region having the CDRL1 amino acid sequence shown in SEQ ID NO: 8, the CDRL2 amino acid sequence shown in SEQ ID NO: 9, and the CDRL3 amino acid sequence shown in SEQ ID NO: 10; and b) oxidized forms of the antibody comprising a heavy chain amino acid residue oxidized at methionine 64.

Another aspect of the disclosure is a composition comprising a) an anti-IL-5 antibody comprising a heavy chain variable region having the CDRH1 amino acid sequence shown in SEQ ID NO: 5, the CDRH2 amino acid sequence shown in SEQ ID NO: 6, and the CDRH3 amino acid sequence shown in SEQ ID NO: 7; and a light chain variable region having the CDRL1 amino acid sequence shown in SEQ ID NO: 8, the CDRL2 amino acid sequence shown in SEQ ID NO: 9, and the CDRL3 amino acid sequence shown in SEQ ID NO: 10; and b) oxidized forms of the antibody comprising a heavy chain amino acid residue oxidized at methionine 64; and c) deamidated forms of the antibody comprising a light chain amino acid residue deamidated at asparagine 31.

Another aspect of the disclosure is a composition comprising a) an anti-IL-5 antibody comprising a heavy chain variable region sequence having the amino acid sequence shown in SEQ ID NO: 3 and a light chain variable region sequence having the amino acid sequence shown in SEQ ID NO: 4; and b) deamidated forms of the antibody comprising a light chain amino acid residue deamidated at asparagine 31.

Another aspect of the disclosure is a composition comprising a) an anti-IL-5 antibody comprising a heavy chain variable region sequence having the amino acid sequence shown in SEQ ID NO: 3 and a light chain variable region sequence having the amino acid sequence shown in SEQ ID NO: 4; and b) oxidized forms of the antibody comprising at least one selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85 and a light chain amino acid residue oxidized at methionine 4.

Another aspect of the disclosure is a composition comprising a) an anti-IL-5 antibody comprising a heavy chain variable region sequence having the amino acid sequence shown in SEQ ID NO: 3 and a light chain variable region sequence having the amino acid sequence shown in SEQ ID NO: 4; b) deamidated forms of the antibody comprising a light chain amino acid residue deamidated at asparagine 31; and c) oxidized forms of the antibody comprising at least one selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85 and a light chain amino acid residue oxidized at methionine 4.

Another aspect of the disclosure is a composition comprising a population of anti-IL-5 antibodies having a) a modified form of the antibody heavy chain amino acid sequence shown in SEQ ID NO: 1 comprising at least one amino acid residue modification selected from the group consisting of an amino terminal pyroglutamate residue at amino acid residue 1, a carboxy terminal glycine amino acid residue at amino acid residue 448, a deamidated asparagine residue at position 299, a deamidated asparagine residue at position 317, a deamidated asparagine residue at position 386, a oxidized tryptophan residue at position 52, an oxidized methionine residue at position 64, an oxidized methionine residue at position 82, an oxidized methionine residue at position 85, an oxidized cysteine at position 222, an oxidized methionine at position 254, an oxidized methionine at position 360 and an oxidized methionine residue at position 430; and b) a modified form of the antibody light chain amino acid sequence shown in SEQ ID NO: 2 comprising at least one amino acid residue modification selected from the group consisting of a deamidated asparagine residue at amino acid residue 31, an oxidized methionine residue at position 4 and an oxidized cysteine at position 220.

Another aspect of the disclosure is a composition comprising a population of anti-IL-5 antibodies having a) a modified form of the antibody heavy chain amino acid sequence shown in SEQ ID NO: 1 comprising at least one amino acid residue modification selected from the group consisting of a deamidated asparagine residue at position 299, a deamidated asparagine residue at position 317, a deamidated asparagine residue at position 386, an oxidized tryptophan residue at position 52, an oxidized methionine residue at position 64, an oxidized methionine residue at position 82, an oxidized methionine residue at position 85, an oxidized cysteine at position 222, an oxidized methionine at position 254, an oxidized methionine at position 360, and an oxidized methionine residue at position 430; and b) a modified form of the antibody light chain amino acid sequence shown in SEQ ID NO: 2 comprising at least one amino acid residue modification selected from the group consisting of a deamidated asparagine residue at amino acid residue 31, an oxidized methionine residue at position 4 and an oxidized cysteine at position 220.

Another aspect of the disclosure is a composition comprising a population of anti-IL-5 antibodies having a) a modified form of the antibody heavy chain amino acid sequence shown in SEQ ID NO: 1 comprising at least one amino acid residue modification selected from the group consisting of a deamidated asparagine residue at position 299, a deamidated asparagine residue at position 317 and a deamidated asparagine residue at position 386; and b) a modified form of the antibody light chain amino acid sequence shown in SEQ ID NO: 2 comprising a deamidated asparagine residue at amino acid residue 31.

Another aspect of the disclosure is a composition comprising a population of anti-IL-5 antibodies having a) a modified form of the antibody heavy chain amino acid sequence shown in SEQ ID NO: 1 comprising at least one amino acid residue modification selected from the group consisting of an oxidized tryptophan residue at position 52, an oxidized methionine residue at position 64, an oxidized methionine residue at position 82, an oxidized methionine residue at position 85, an oxidized cysteine at position 222, an oxidized methionine at position 254, an oxidized methionine at position 360, and an oxidized methionine residue at position 430; and b) a modified form of the antibody light chain amino acid sequence shown in SEQ ID NO: 2 comprising at least one selected from the group consisting of an oxidized methionine residue at position 4 and an oxidized cysteine at position 220.

Another aspect of the disclosure is a composition comprising a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2; and b) a main form of the antibody comprising greater than, or equal to, 20% of the protein in the composition as measured using capillary isoelectric focusing of the composition.

Another aspect of the disclosure is a composition comprising a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2; b) a main form of the antibody comprising greater than, or equal to, 20% of the protein in the composition as measured using capillary isoelectric focusing of the composition; and c) acidic forms of the antibody comprising up to about 80% of the protein in the composition as measured using capillary isoelectric focusing of the composition.

DETAILED DESCRIPTION OF THE DISCLOSURE

Figure 1:
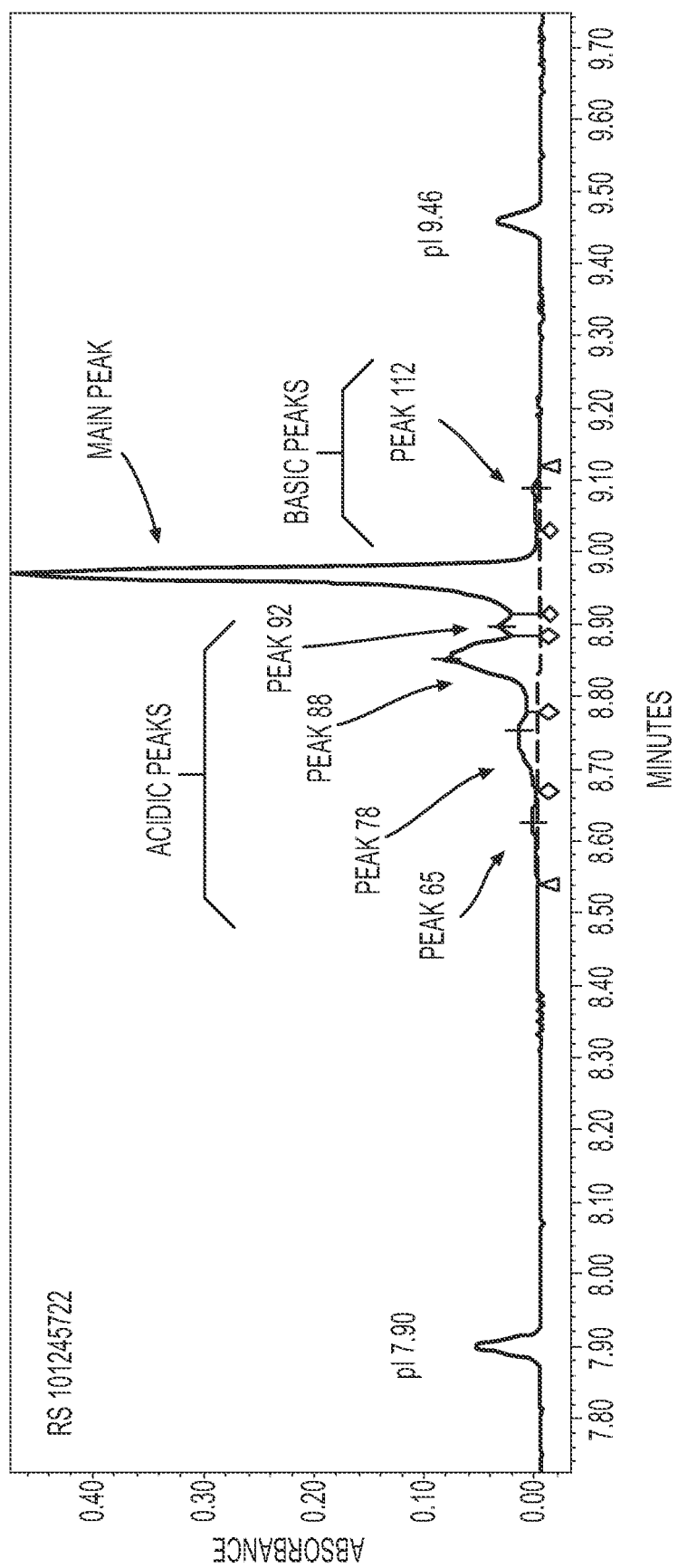
FIG. 1. Representative capillary isoelectric focusing (cIEF) electropherogram of a reference standard (RS) composition comprising mepolizumab.
Figure 2:
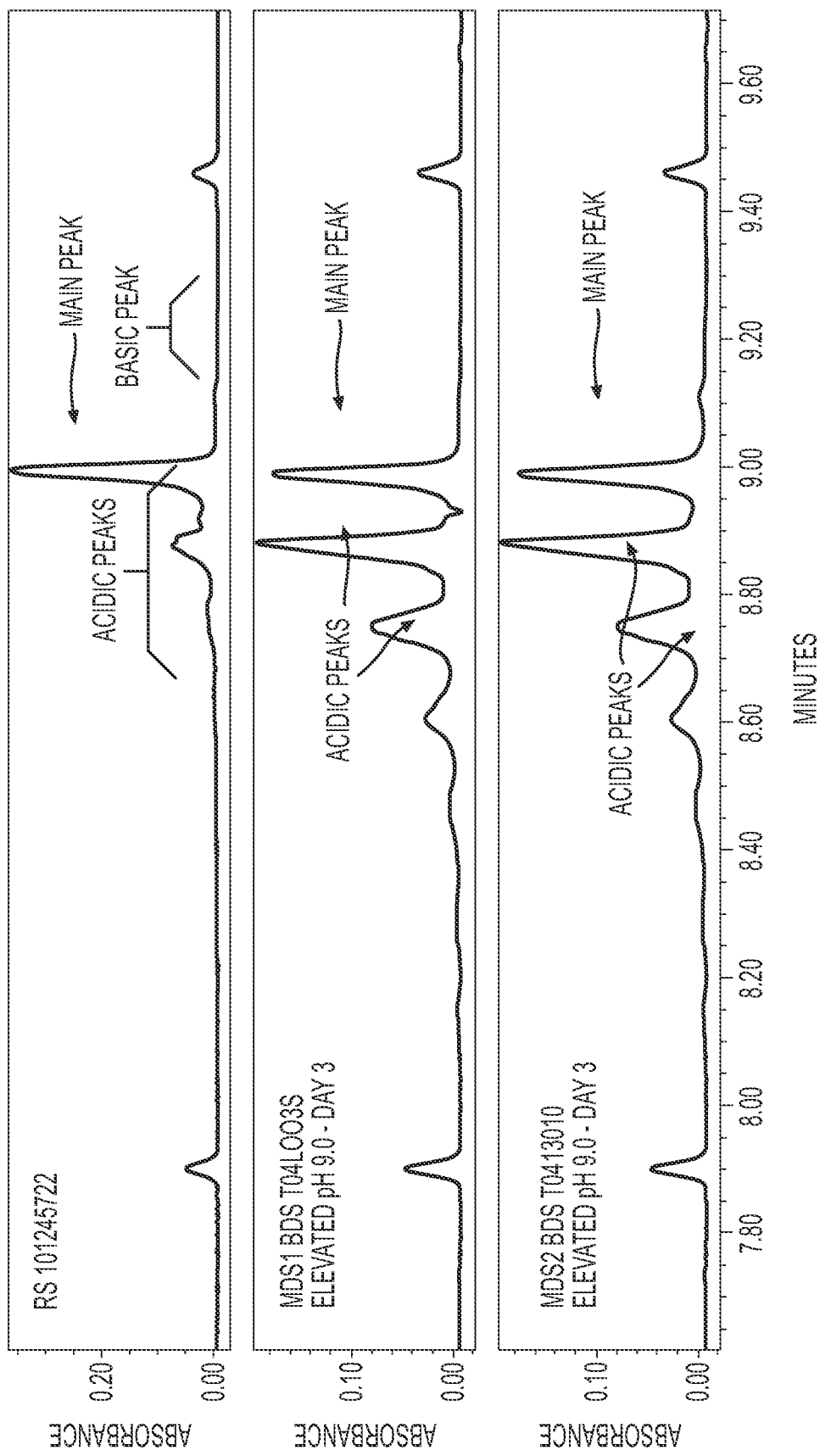
FIG. 2. Representative cIEF electropherograms of a reference standard composition comprising mepolizumab (control) and different batches of the compositions comprising mepolizumab subjected to three days of pH 9.0 forced degradation.

The present disclosure provides compositions, for treating interleukin 5 (IL-5) mediated diseases, and related subject matter.

The term "asthma" as used herein means an inflammatory disease of the airways characterized by reversible airflow obstruction and bronchospasm. Common symptoms include wheezing, coughing, chest tightness, and shortness of breath.

In the methods of the disclosure "asthma" may be "severe eosinophilic asthma." Subjects with severe eosinophilic asthma may have asthma and blood eosinophils greater than or equal to 300 eosinophils per µL of blood in the past 12 months. Subjects with severe eosinophilic asthma may meet, one or more of, the criteria described in Table 1.

TABLE 1

A subject has severe eosinophilic asthma if they meet the following criteria:

| | |
|---|---|
| 1) | The subject has clinical features of severe refractory asthma similar to those indicated in the American Thoracic Society Workshop on Refractory Asthma (162 *Am. J. Respir. Crit. Care Med.* 2341 (2000) for ≥12 months. |
| 2) | The subject has a well-documented requirement for regular treatment with high dose ICS (inhaled corticosteroids) (i.e., ≥880 µg/day fluticasone propionate or equivalent daily), with or without maintenance OCS (oral corticosteroids), in the past 12 months. |
| 3) | The subject has a well-documented requirement for controller medication, e.g., long-acting beta-2-agonist, leukotriene receptor antagonist or theophylline in the past 12 months. |

TABLE 1-continued

A subject has severe eosinophilic asthma if they meet the following criteria:

| | |
|---|---|
| 4) | The subject has persistent airflow obstruction as indicated by a pre-bronchodilator $FEV_1$ <80% predicted recorded or peak flow diurnal variability of >20% on 3 or more days. |
| 5) | The subject has airway inflammation which is likely to be eosinophilic in nature as indicated by one of the following characteristics at present or documented in the previous 12 months:<br>An elevated peripheral blood eosinophil level of ≥300/µL that is related to asthma or<br>Sputum eosinophils ≥3% or<br>Exhaled nitric oxide ≥50 ppb or<br>Prompt deterioration of asthma control (based on documented clinical history or objective measures) following a ≤25% reduction in regular maintenance dose of inhaled or oral corticosteroid dose in the previous 12 months |
| 8) | The subject has a previously confirmed history of two or more asthma exacerbations requiring treatment with oral or systemic corticosteroids in the prior 12 months prior, despite the use of high-dose ICS and additional controller medication. For subjects receiving maintenance OCS with high-dose ICS plus controller, the OCS treatment for exacerbations had to be a two-fold or greater increase in the dose of OCS. |
| 9) | The subject has asthma as documented by either:<br>Airway reversibility ($FEV_1$ ≥12% and 200 mL) at present or documented in the previous 12 months or<br>Airway hyper-responsiveness (provocative concentration causing a 20% fall in $FEV_1$ of methacholine <8 mg/mL or provocative dose causing a 20% fall in $FEV_1$ of histamine <7.8 µmol) documented in the prior 12 months or<br>Airflow variability in clinic $FEV_1$ ≥20% between two examinations documented in the prior 12 months ($FEV_1$ recorded during an exacerbation is not valid) or<br>Airflow variability as indicated by >20% diurnal variability in peak flow observed on 3 or more days. |

Importantly, subjects with severe eosinophilic asthma according to these criteria may have less than 150 eosinophils per µL of blood at the initiation of treatment. Mepolizumab is a monoclonal antibody comprising the heavy chain amino acid sequence shown in SEQ ID NO: 1 and the light chain amino acid sequence shown in SEQ ID NO: 2. Mepolizumab, and antigen binding proteins, in particular antibody molecules, comprising the heavy chain CDRs and light chain CDRs of mepolizumab, may be used to treat severe eosinophilic asthma according to the methods of the disclosure. For example, mepolizumab, or related antigen binding proteins, may be indicated for add-on maintenance treatment of severe eosinophilic asthma, as identified by blood eosinophils greater than or equal to 300 cells/µL in the past 12 months and/or blood eosinophils greater than or equal to 150 cells/µL at initiation of treatment and/or blood eosinophils less than 150 cells/µL at initiation of treatment, in patients. Alternatively, mepolizumab, or related antigen binding proteins, may be indicated for add-on maintenance treatment of severe eosinophilic asthma, as identified by blood eosinophils greater than or equal to 300 cells/µL in the past 12 months and/or blood eosinophils greater than or equal to 150 cells/µL at initiation of treatment, in patients. Mepolizumab, or related antigen binding proteins, may be indicated for add-on maintenance treatment of severe eosinophilic asthma, as identified by blood eosinophils greater than or equal to 300 cells/µL in the past 12 months and/or blood eosinophils less than 150 cells/µL at initiation of treatment, in patients. Such patients may be aged 12 years and older. Mepolizumab treatment may reduce exacerbations of asthma in patients (e.g., patients with an exacerbation history). The methods of the disclosure may be used when mepolizumab treatment is indicated (i.e., such treatment with mepolizumab may be combined with the methods of the disclosure). Treatment with mepolizumab can:

a) Produce a reduction in exacerbation frequency. Compared with placebo, treatment with mepolizumab, such as 100 mg per subject administered subcutaneously or 75 mg per subject administered intravenously, can reduce the rate of 1) clinically significant exacerbations, 2) exacerbations requiring hospitalization or ED visits, and 3) exacerbations requiring hospitalization. This benefit may potentially lead to reductions in morbidity and fatal events due to asthma.

b) Produce a reduction in daily OCS dose: Treatment with mepolizumab, such as 100 mg per subject administered subcutaneously or 75 mg per subject administered intravenously, may allow subjects to reduce their daily dose of concomitant corticosteroid without experiencing loss of asthma control. Subjects treated with mepolizumab may achieve a median percentage reduction of 50% from baseline in daily oral corticosteroid (OCS) dose versus 0% for those treated with placebo. In addition, 54% of subjects treated with mepolizumab may achieve a reduction of OCS dose to 5.0 mg compared with 32% of subjects treated with placebo (p=0.025).

c) Produce an improvement in lung function: Clinically relevant changes in pre- and post-bronchodilator $FEV_1$ may be demonstrated with mepolizumab treatment, such as 100 mg per subject administered subcutaneously or 75 mg per subject administered intravenously, compared with placebo. Any improvements in lung function are of particular clinical importance in this population of subjects as most are on maximal asthma therapy including high dose ICS (inhaled corticosteroids) and/or OCS plus a controller medication.

d) Produce an improvement in asthma control: Statistically significant and clinically relevant improvements may be observed in ACQ-5 with mepolizumab, such as 100 mg per subject administered subcutaneously or 75 mg per subject administered intravenously, compared with placebo, indicating subjects may achieve asthma control with the addition of mepolizumab to their existing asthma treatment.

e) Produce an improvement in quality of life: Statistically significant and clinically relevant changes in SGRQ scores may be demonstrated with mepolizumab, such as 100 mg per subject administered subcutaneously or 75 mg per subject administered intravenously, compared with placebo. Subjects may experience marked improvement in asthma symptoms and ability of perform daily activities.

f) Produce a persistence of efficacy and pharmacodynamic effect: Over a period of 32- and/or 52-week treatment durations, a sustained reduction in asthma exacerbations and blood eosinophils, and improvements in lung function, asthma control, and quality of life with no development of tolerance may be observed.

and g) Produce a reduction in blood eosinophils. Treatment with compositions comprising mepolizumab, such as 100 mg of mepolizumab per subject administered subcutaneously or 75 mg per subject administered intravenously, may result in rapid reduction of blood eosinophils (approximately 80% by the first assessment at Week 4 after initial treatment; e.g., from 250-290 cells/µL to 40-60 cells/µL etc.).

In the methods of the disclosure "asthma" may be "severe asthma." Subjects with severe asthma meet the definition of severe asthma described in the European Respiratory Society/American Thoracic Society (ERS/ATS) Guidelines for severe asthma. Thus, severe asthma is asthma which requires treatment with guideline suggested medications for Global Initiative for Asthma (GINA) steps 4-5 asthma (high dose inhaled corticosteroids [ICS] plus long acting beta2-agonist [LABA] or leukotriene modifier/theophylline) for the previous year, or systemic corticosteroids (CS) for >=50% of the previous year to maintain control of the subject's asthma. Treatment with compositions comprising mepolizumab may be used to treat severe asthma according to the methods of the disclosure.

In the methods of the disclosure "asthma" may be "uncontrolled eosinophilic asthma." Subjects with uncontrolled eosinophilic asthma meet the criteria described in Table 2.

TABLE 2

A subject has uncontrolled eosinophilic asthma if they meet the following criteria:

| | |
|---|---|
| 1) | The subject has a history of diagnosed asthma for at least the prior 12 months. |
| 2) | The subject has been prescribed daily use of medium-dose or high-dose ICS (inhaled corticosteroid) plus LABA (long-acting beta agonists) for a least the prior 12 months. |
| 3) | The subject's dose of other asthma controller medications must be stable for at least the prior 30 days. |
| 4) | The subject has at least 2 documented asthma exacerbations in the prior 12 months that required use of a systemic corticosteroid burst. |

Treatment with compositions comprising mepolizumab may be used to treat uncontrolled eosinophilic asthma according to the methods of the disclosure.

In the methods of the disclosure "asthma" may be "eosinophilic asthma." Subjects with uncontrolled eosinophilic asthma meet the criteria described in Table 3.

TABLE 3

A subject has eosinophilic asthma if they meet the following criteria:

| | |
|---|---|
| 1) | The patient has a previous diagnosis of asthma. |
| 2) | The patient has had at least 1 asthma exacerbation requiring oral, intramuscular (im), or intravenous (iv) corticosteroid use for at least 3 days in the prior 12 months. |
| 3) | The patient has a current blood eosinophil level of at least 400/µl. |
| 4) | The patient has airway reversibility of at least 12% to beta-agonist administration. |
| 5) | The patient has an ACQ score of at least 1.5. |
| 6) | The patient is taking inhaled fluticasone at a dosage of at least 440 µg, or equivalent, daily. Chronic oral corticosteroid use (no more than 10 mg/day prednisone or equivalent) is allowed. The patient's baseline asthma therapy regimen (including, but not limited to, inhaled corticosteroids, oral corticosteroids up to a maximum dose of 10 mg prednisone daily or equivalent, leukotriene antagonists, 5-lipoxygenase inhibitors, or cromolyn) must be stable for the prior 30 days. |

In the methods of the disclosure "asthma" may be "sub-eosinophilic asthma." Subjects with uncontrolled eosinophilic asthma meet the criteria described in Table 4.

TABLE 4

A subject has sub-eosinophilic asthma if they meet the following criteria:

| | |
|---|---|
| 1) | The patient has a previous diagnosis of asthma. |
| 2) | The patient has had at least 1 asthma exacerbation requiring oral, intramuscular (im), or intravenous (iv) corticosteroid use for at least 3 days in the prior 12 months. |
| 3) | The patient has a current blood eosinophil level of less than 400/µl. |
| 4) | The patient has airway reversibility of at least 12% to beta-agonist administration. |
| 5) | The patient has an ACQ score of at least 1.5. |
| 6) | The patient is taking inhaled fluticaseone at a dosage of at least 440 µg, or equivalent, daily. Chronic oral corticosteroid use (no more than 10 mg/day prednisone or equivalent) is allowed. The patient's baseline asthma therapy regimen (including, but not limited to, inhaled corticosteroids, oral corticosteroids up to a |

TABLE 4-continued

A subject has sub-eosinophilic asthma if they meet the following criteria:

maximum dose of 10 mg prednisone daily or equivalent, leukotriene antagonists, 5-lipoxygenase inhibitors, or cromolyn) must be stable for the prior 30 days.

Treatment with compositions comprising mepolizumab may be used to treat sub-eosinophilic asthma and may also be used to treat sub-eosinophilic asthma according to the methods of the disclosure.

The term "bullous pemphigoid" (BP) as used herein means an acute or chronic autoimmune skin disease, involving the formation of blisters, more appropriately known as bullae, at the space between the skin layers epidermis and dermis. BP is the most common autoimmune blistering skin disease. It characteristically affects the elderly (>70 years) with an annual incidence of 5 to 35 per million. The incidence of BP is dramatically increasing with an average of 17% per year. BP often starts with extremely pruritic skin lesions resembling eczema or urticaria before vesicles and blisters arise. In 10-30% of patients, BP also involves the oral mucosa. Disease severity can be determined by means of the autoimmune bullous skin disorder intensity score (ABSIS) that evaluates the involved area as well as the disease activity. The disease is due to an autoimmune response to structural components of junctional adhesion complexes leading to the damage of the dermal-epidermal junction with subepidermal blister formation. Specifically, autoreactive B and T cell responses against the hemidesmosomal antigens BP180 and BP230 have been identified. Serum levels of autoantibodies to BP180 reflect the disease severity and activity. The T cells are memory CD4+ cells producing both Th1 and Th2 cytokines, mostly IL-4, IL-5 and IL-13. IL-5 as well as eotaxin are abundantly found in blister fluids. The production of IL-5 is indeed associated with blood eosinophilia and significant eosinophil infiltration in the skin of BP patients. Eosinophils are thought to be critically implicated in blister formation by releasing toxic granule proteins (ESP, MBP) and proteolytic enzymes.

The term "eosinophilic esophagitis" (EoE) as used herein means an allergic inflammatory condition of the esophagus that involves eosinophils. Symptoms are swallowing difficulty, food impaction, and heartburn. EoE is characterised by a dense infiltrate with white blood cells of the eosinophil type into the epithelial lining of the esophagus. EoE is believed to be an allergic reaction against ingested food, based on the important role eosinophils play in allergic reactions. The EoE diagnostic panel can be used to diagnose EoE. EoE can also be diagnosed if gastroesophageal reflux does not respond to a 6 week trial of twice-a-day high-dose proton-pump inhibitors (PPIs) or if a negative ambulatory pH study ruled out gastroesophageal reflux disease (GERD). Endoscopically, ridges, furrows, or rings may be seen in the oesophageal wall. Sometimes, multiple rings may occur in the esophagus, leading to the term "corrugated esophagus" or "feline esophagus" due to similarity of the rings to the cat esophagus. The presence of white exudates in esophagus is also suggestive of the diagnosis. On biopsy taken at the time of endoscopy, numerous eosinophils can typically be seen in the superficial epithelium. A minimum of 15 eosinophils per high-power field are required to make the diagnosis. Eosinophilic inflammation is not limited to the oesophagus alone, and does extend though the whole gastrointestinal tract. Profoundly degranulated eosinophils may also be present, as may microabcesses and an expansion of the basal layer. Radiologically, the term "ringed esophagus" has been used for the appearance of eosinophilic esophagitis on barium swallow studies to contrast with the appearance of transient transverse folds sometimes seen with esophageal reflux (termed "feline esophagus").

Treatment with compositions comprising mepolizumab may be used to treat COPD according to the methods of the disclosure.

Subjects with "chronic obstructive pulmonary disease" (COPD) may meet one or more following criteria: a) a prior COPD diagnosis: subjects with a clinically documented history of COPD for at least 1 year in accordance with the definition by the American Thoracic Society/European Respiratory Society; b) severity of COPD: Subjects may present with the following: a measured pre and post-salbutamol Forced Expiratory Volume in one second/Forced vital capacity ($FEV_1/FVC$) ratio of <0.70 to confirm a diagnosis of COPD; a measured post-salbutamol $FEV_1$>20 percent and <=80 percent of predicted normal values calculated using National Health and Nutrition Examination Survey (NHANES) III reference equations; c) a history of exacerbations: a well documented history (like medical record verification) in the 12 months of: at least two moderate COPD exacerbations. Moderate is defined as the use of systemic corticosteroids (IM, intravenous, or oral) and/or treatment with antibiotics, or at least one severe COPD exacerbation. Severe is defined as having required hospitalization. Note: At least one exacerbation must have occurred while the subject was taking Inhaled corticosteroid (ICS) plus long acting beta2-agonist (LABA) plus long acting muscarinic antagonist (LAMA). Note: Prior use of antibiotics alone does not qualify as a moderate exacerbation unless the use was specifically for the treatment of worsening symptoms of COPD; and d) concomitant COPD therapy: a well documented requirement for optimized standard of care (SoC) background therapy that includes ICS plus 2 additional COPD medications (i.e., triple therapy) for the 12 months prior and meets the following criteria: Immediately prior to visit to the healthcare provider, a minimum of 3 months of use of an inhaled corticosteroid (at a dose >=500 micrograms (mcg)/day fluticasone propionate dose equivalent plus); or LABA and LAMA.

Treatment with compositions comprising mepolizumab may be used to treat COPD according to the methods of the disclosure.

The term "eosinophilic granulomatosis with polyangiitis" (EGPA) as used herein means an autoimmune condition that causes inflammation of small and medium-sized blood vessels (vasculitis) in persons with a history of airway allergic hypersensitivity (atopy). EGPA may also be referred to as Churg-Strauss Syndrome (CSS) or allergic granulomatosis. EGPA usually manifests in three stages. The early (prodromal) stage is marked by airway inflammation; almost all patients experience asthma and/or allergic rhinitis. The second stage is characterized by abnormally high numbers of eosinophils (hypereosinophilia), which causes tissue damage, most commonly to the lungs and the digestive tract. The third stage consists of vasculitis, which can eventually lead to cell death and can be life-threatening.

Subjects with EGPA may meet one or more following criteria: a) asthma; b) blood eosinophil levels greater than 10% of a differential white blood cell count; c) presence of mononeuropathy or polyneuropathy; d) unfixed pulmonary infiltrates; e) presence of paranasal sinus abnormalities; and e) histological evidence of extravascular eosinophils. For classification purposes, a patient shall be said to have EGPA if at least four of the preceding six criteria are positive.

Treatment with compositions comprising mepolizumab may be used to treat EGPA according to the methods of the disclosure. The compositions of the disclosure may be administered to an EGPA patient in an amount of 300 mg once every 4 weeks.

The term "hypereosinophilic syndrome" (HES) as used herein means a disease characterized by a persistently elevated eosinophil count (≥1500 eosinophils/mm³) in the blood for at least six months without any recognizable cause, with involvement of either the heart, nervous system, or bone marrow.

Subjects with hypereosinophilic syndrome may meet one or more following criteria: a) a documented history of hypereosinophilic syndrome; b) a blood eosinophil count greater than 1500 cells for 6 months; c) signs and symptoms of organ system involvement; and d) no evidence of parasitic, allergic or other causes of eosinophilia after comprehensive evaluation.

Treatment with compositions comprising mepolizumab may be used to treat hypereosinophilic syndrome according to the methods of the disclosure. The compositions of the disclosure may be administered to a hypereosinophilic syndrome patient in an amount of 300 mg once every 4 weeks.

The term "nasal polyposis" as used herein means a disease characterized by the presence of polyps nasal cavity. Such polyps may be in the upper nasal cavity and/or may originate from within the ostiomeatal complex.

Subjects with nasal polyposis may meet one or more following criteria: a) a documented history of nasal polyposis; or b) nasal polyps apparent on examination (e.g., endoscopic examination).

Treatment with compositions comprising mepolizumab may be used to treat nasal polyposis according to the methods of the disclosure. The compositions of the disclosure may be administered to a nasal polyposis patient in an amount of 750 mg once every 4 weeks.

The term "antibody" as used herein refers to molecules with an immunoglobulin-like domain (e.g., IgG, IgM, IgA, IgD or IgE) and includes monoclonal, recombinant, polyclonal, monoclonal, recombinant, polyclonal, chimeric, human, and humanized molecules of this type. Monoclonal antibodies may be produced by a eukaryotic cell clone expressing an antibody. Monoclonal antibodies may also be produced by a eukaryotic cell line which can recombinantly express the heavy chain and light chain of the antibody by virtue of having nucleic acid sequences encoding these introduced into the cell. Methods to produce antibodies from different eukaryotic cell lines such as Chinese Hamster Ovary cells, hybridomas or immortalized antibody cells derived from an animal (e.g., human) are well known.

The antibody may be derived from rat, mouse, primate (e.g., cynomolgus, Old World monkey or Great Ape), human or other sources such as nucleic acids generated using molecular biology techniques which encode an antibody molecule.

The antibody may comprise a constant region, which may be of any isotype or subclass. The constant region may be of the IgG isotype, for example, $IgG_1$, $IgG_2$, $IgG_3$, $IgG_4$ or variants thereof. The antigen binding protein constant region may be $IgG_1$.

The antigen binding protein may comprise one or more modifications selected from a mutated constant domain such that the antibody has enhanced effector functions/ADCC and/or complement activation.

An antibody may be capable of binding to a target antigen. Examples, of such target antigens include human IL-5 comprising the amino acid sequence shown in SEQ ID NO: 11.

Mepolizumab comprising the heavy chain amino acid sequence shown in SEQ ID NO: 1 and the light chain amino acid sequence shown in SEQ ID NO: 2 is an example of an antibody. Mepolizumab binds human IL-5 and antagonizes its activity.

Mepolizumab is a recombinant humanized monoclonal antibody ($IgG_1$, Kappa) Mepolizumab has two light and two heavy chains.

The mepolizumab heavy chain is encoded by the nucleic acid sequence shown in SEQ ID NO: 13. The mepolizumab heavy chain contains 449 amino acids with an estimated molecular mass of approximately 49 kDa. The predicted mature heavy chain amino acid sequence for mepolizumab is:

(SEQ ID NO: 1)
QVTLRESGPALVKPTQTLTLTCTVSGFSLTSYSVHWVRQPPGKGLEWLGV
IWASGGTDYNSALMSRLSISKDTSRNQVVLTMTNMDPVDTATYYCARDPP
SSLLRLDYWGRGTPVTVSSASTKGPSVFPLAPSSKSTSGGTAALGCLVKD
YFPEPVTVSWNSGALTSGVHTFPAVLQSSGLYSLSSVVTVPSSSLGTQTY
ICNVNHKPSNTKVDKRVEPKSCDKTHTCPPCPAPELLGGPSVFLFPPKPK
DTLMISRTPEVTCVVVDVSHEDPEVKFNWYVDGVEVHNAKTKPREEQYN*
STYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK

In the heavy chain amino acid sequence above, heavy chain frameworks and CDRs according to the Kabat definition are identified as zig-zag underlined framework1, solid underlined CDR1, zig-zag underlined framework2, solid underlined CDR2, zig-zag underlined framework3, solid underlined CDR3 and zig-zag framework4 in order from the amino proximal portion to the carboxy terminal portion of the sequence presented. In the heavy chain amino acid sequence above, an asterisk to the right of a character for a single letter amino acid code indicates the amino acid residue to the left can be a N-glycosylation site.

The mepolizumab light chain is encoded by the nucleic acid sequence shown in SEQ ID NO: 14. The mepolizumab light chain contains 220 amino acids residues with an estimated molecular mass of approximately 24 kDa. The mature light chain amino acid sequence is:

(SEQ ID NO: 2)
DIVMTQSPDSLAVSLGERATINCKSSQSLLNSGNQKNYLAWYQQKPGQPP
KLLIYGASTRESGVPDRFSGSGSGTDFTLTISSLQAEDVAVYYCQNVHSF
PFTFGGGTKLEIKRTVAAPSVFIFPPSDEQLKSGTASVVCLLNNFYPREA
KVQWKVDNALQSGNSQESVTEQDSKDSTYSLSSTLTLSKADYEKHKVYAC
EVTHQGLSSPVTKSFNRGEC

In the light chain amino acid sequence above, light chain frameworks and CDRs according to the Kabat definition are identified as zig-zag underlined framework1, solid underlined CDR1, zig-zag underlined framework2, solid underlined CDR2, zig-zag underlined framework3, solid underlined CDR3 and zig-zag framework4 in order from the amino proximal portion to the carboxy terminal portion of the sequence presented.

The mepolizumab heavy and light chains are covalently linked by a single disulfide bond and the heavy chains are linked to each other by two disulfide bonds resulting in a typical IgG molecule. Both heavy chains can be glycosylated at asparagine 299 with complex biantennary oligosaccharides. The predicted polypeptide molecular mass is about 146 kDa and the predicted carbohydrate molecular mass is approximately 3 kDa giving a total estimated molecular mass of 149.2 kDa for mepolizumab. Mepolizumab as encoded has 1338 amino acid residues (220 amino acid residues per light chain, 449 amino acid residues per heavy chain). The main pI of mepolizumab is about 8.7-9.1. The equilibrium dissociation constant ($K_D$) for the molecular interaction of mepolizumab and human IL-5 as measured using standard surface plasmon resonance assays is less than $2.29 \times 10^{-11}$ M.

Mepolizumab can be provided as a lyophilized powder containing the antibody and excipients which can be reconstituted with a pharmaceutically acceptable carrier (e.g., sterile water). This reconstituted pharmaceutical composition can then be administered either subcutaneously or intravenously (e.g., with further dilution). Mepolizumab can also be provided as a liquid formulation containing the antibody, excipients and a pharmaceutically acceptable carrier. This liquid pharmaceutical composition can then be administered either subcutaneously or intravenously (e.g., with further dilution).

The term "antibody variant" as used herein means an antibody that differs from a parent antibody by virtue of at least one amino acid modification (e.g., by having a different amino acid side chain), post-translational modification or other modification in at least one heavy chain, light chain, or combinations of these that results in a structural change (e.g., different amino acid side chain, different post-translational modification or other modification) relative to the parent antibody. Mepolizumab is an example of a such a parent antibody. Structural changes can be determined directly by a variety of methods well know in the art such as LC-MS, direct sequencing or indirectly via methods such as isoelectric focusing and the like. Such methods are well known to those of ordinary skill in the art.

The term "IL-5" as used herein means human IL-5 comprising the amino acid sequence shown in SEQ ID NO: 11.

The term "specifically binds", as used herein in relation to antigen binding proteins means that the antigen binding protein binds to a target antigen as well as a discrete domain, or discrete amino acid sequence, within a target antigen with no or insignificant binding to other (for example, unrelated) proteins. This term, however, does not exclude the fact that the antigen binding proteins may also be cross-reactive with closely related molecules (for example, those with a high degree of sequence identity or from another genera or species). The antigen binding proteins described herein may bind to human IL-5 or the human IL-5 receptor with at least 2, 5, 10, 50, 100, or 1000-fold greater affinity than they bind to closely related molecules.

The binding affinity ($K_D$) of the antigen binding protein-target antigen interaction may be 1 mM or less, 100 nM or less, 10 nM or less, 2 nM or less or 1 nM or less. Alternatively, the $K_D$ may be between 5 and 10 nM; or between 1 and 2 nM. The $K_D$ may be between 1 pM and 500 pM; or between 500 pM and 1 nM. The binding affinity of the antigen binding protein is determined by the association constant (Ka) and the dissociation constant (Kd) (KD=Kd/Ka). The binding affinity may be measured by BIACORE™, for example, by capture of the test antibody onto a protein-A coated sensor surface and flowing target antigen over this surface. Alternatively, the binding affinity can be measured by FORTEBIO, for example, with the test antibody receptor captured onto a protein-A coated needle and flowing target antigen over this surface.

The $K_d$ may be $1 \times 10^{-3}$ Ms$^{-1}$ or less, $1 \times 10^{-4}$ Ms$^{-1}$ or less, or $1 \times 10^{-5}$ Ms$^{-1}$ or less. The $K_d$ may be between $1 \times 10^{-5}$ Ms$^{-1}$ and $1 \times 10^{-4}$ Ms$^{-1}$; or between $1 \times 10^{-4}$ Ms$^{-1}$ and $1 \times 10^{-3}$ Ms$^{-1}$. A slow $K_d$ may result in a slow dissociation of the antigen binding protein-target antigen complex and improved neutralization of the target antigen.

The term "specific antigen binding activity" as used herein means antigen binding activity as measured by Surface Plasmon Resonance (SPR). IL-5 specific binding activity may be determined by SPR using a BIACORE™ instrument, for example performed in the binding mode. It is binding activity divided by total protein (e.g., mepolizumab) content in a sample.

The term "FcRn binding activity" as used herein means Neonatal Fc (FcRn) Receptor binding activity as measured by Surface Plasmon Resonance (SPR). FcRn binding may be determined using a BIACORE™ instrument. It is binding activity to the FcRn receptor, divided by the total protein concentration of the sample.

The SPR method for specific antigen binding and FcRn binding uses a reference standard of mepolizumab. The mepolizumab reference standard can be used in assays to obtain system suitability and sample comparability data, to ensure methods are performing appropriately. The reference standard can allow the establishment of a calibration curve and concentrations of the samples are interpolated from the curve.

For example, the reference standard is a composition comprising SEQ ID NO:1 and SEQ ID NO:2. In another embodiment, the reference standard is a composition comprising SEQ ID NO:1 and SEQ ID NO:2, and 98% or more HC C-terminal lysine deleted variant, and 95% or more HC N-terminal pyro-glutamate variant. In a further embodiment, the reference standard is a composition comprising SEQ ID NO:1 and SEQ ID NO:2, and 98% or more HC C-terminal lysine deleted variant, 95% or more HC N-terminal pyro-glutamate variant, and 6% or less deamidated variant. In another embodiment, the reference standard is a composition comprising SEQ ID NO:1 and SEQ ID NO:2, and 98% or more HC C-terminal lysine deleted variant, 95% or more HC N-terminal pyro-glutamate variant, 6% or less deamidated variant, 4% or less methionine or cysteine oxidated variant, and 0.1% tryptophan oxidated variant. In a further embodiment, the reference standard is a composition comprising SEQ ID NO:1 and SEQ ID NO:2, and 98% or more HC C-terminal lysine deleted variant, 95% or more HC N-terminal pyro-glutamate variant, 6% or less deamidated variant, 4% or less methionine or cysteine oxidated variant, 0.1% or less tryptophan oxidated variant, and 0.4% or less aggregated variant. In another embodiment, the reference standard is a composition comprising the isoforms represented by peak 65, peak 78, peak 88, peak 92, the main peak and peak 112 shown in FIG. 1. In one embodiment the reference standard is a composition comprising SEQ ID NO: 1 and SEQ ID NO:2, about 62.9% main peak, about 35.9% acidic peak, about 1.2% basic peak, about 99.6% monomer, about 0.4% aggregate, about 0% fragment, about 0.8% HC deamidated N317, about 5.5% HC deamidated N386, about 5.2% HC deamidated N31, about 0.2% HC deamidated N299, about 0.9% HC oxidised M64, about 3.5% HC oxidised M254, about 0.5% HC oxidised M360, about 0.5% HC oxidised M430, about 0.3% HC oxidised M82 and M85, about 0.2% LC oxidised M4, about 0.0% LC oxidised C220, about 0.1% HC oxidised W52, 98% or more HC C-terminal lysine deleted variant, and 95% or more HC N-terminal pyro-glutamate variant.

In one embodiment the composition has a specific IL-5 binding activity of ≥0.70; and a FcRn binding activity of ≥70%. For example, the specific antigen binding is in the range of from 0.70 to 1.30; and/or the FcRn binding is in the range of from 70% to 130%, as compared to the reference standard which is set as 1.0 specific IL-5 binding activity, and 100% FcRn binding activity.

IL-5 neutralization $ED_{50}$ ratio is the $ED_{50}$ of a reference antibody standard (e.g., a mepolizumab antibody standard comprising the amino acid sequences of SEQ ID NO: 1 and SEQ ID NO: 2) divided by the $ED_{50}$ of an antibody sample (e.g., a mepolizumab variant sample or a sample of a manufactured batch of composition comprising a mepolizumab antibody comprising the amino acid sequence of SEQ ID NO: 1 and SEQ ID NO: 2).

By "isolated", it is intended that the molecule, such as an antigen binding protein or nucleic acid, is removed from the environment in which it may be found in nature. For example, the molecule may be purified away from substances with which it would normally exist in nature. For example, the mass of the molecule in a sample may be 95% of the total mass.

The terms "$V_H$" and "$V_L$" are used herein to refer to the heavy chain variable region and light chain variable region respectively of an antigen binding protein.

"CDRs" are defined as the complementarity determining region amino acid sequences of an antigen binding protein. These are the hypervariable regions of immunoglobulin heavy and light chains. There are three heavy chain and three light chain CDRs (or CDR regions) in the variable portion of an immunoglobulin. Thus, "CDRs" as used herein refers to all three heavy chain CDRs, all three light chain CDRs, all heavy and light chain CDRs, or at least one CDR and wherein the at least one CDR is CDRH3. Framework regions follow each of these CDR regions. Acceptable heavy chain variable region and light chain variable region framework 1, framework 2 and framework 3 regions are readily recognized by those of ordinary skill in the art. Acceptable heavy chain constant regions (including hinge regions) and light chain constant regions are readily recognized by those of ordinary skill in the art as well. Acceptable antibody isotypes are similarly readily recognized by those of ordinary skill in the art.

Throughout this specification, amino acid residues in variable domain sequences and full length antibody sequences are numbered according to the Kabat numbering convention. Similarly, the terms "CDR", "CDRL1", "CDRL2", "CDRL3", "CDRH1", "CDRH2", "CDRH3" used in the specification follow the Kabat numbering convention.

It will be apparent to those skilled in the art that there are alternative numbering conventions for amino acid residues in variable domain sequences and full length antibody sequences. There are also alternative numbering conventions for CDR sequences, for example those set out according to the Chothia numbering convention. The structure and protein folding of the antibody may mean that other residues are considered part of the CDR sequence and would be understood to be so by a skilled person.

Other numbering conventions for CDR sequences available to a skilled person include "AbM" (University of Bath) and "contact" (University College London) methods. The minimum overlapping region using at least two of the Kabat, Chothia, AbM and contact methods can be determined to provide the "minimum binding unit". The minimum binding unit may be a sub-portion of a CDR.

Table 5 below represents one definition using each numbering convention for each CDR or binding unit. The Kabat numbering scheme is used in Table 5 to number the variable domain amino acid sequence. It should be noted that some of the CDR definitions may vary depending on the individual publication used.

TABLE 5

|    | Kabat CDR | Chothia CDR | AbM CDR | Contact CDR | Minimum binding unit |
|----|-----------|-------------|---------|-------------|----------------------|
| H1 | 31-35/35A/35B | 26-32/33-34 | 26-35/35A/35B | 30-35/35A/35B | 31-32 |
| H2 | 50-65 | 52-56 | 50-58 | 47-58 | 52-56 |
| H3 | 95-102 | 95-102 | 95-102 | 93-101 | 95-101 |
| L1 | 24-34 | 24-34 | 24-34 | 30-36 | 30-34 |
| L2 | 50-56 | 50-56 | 50-56 | 46-55 | 50-55 |
| L3 | 89-97 | 89-97 | 89-97 | 89-96 | 89-96 |

"Percent identity" between a query nucleic acid sequence and a subject nucleic acid sequence is the "Identities" value, expressed as a percentage, that is calculated by the BLASTN algorithm when a subject nucleic acid sequence has 100% query coverage with a query nucleic acid sequence after a pair-wise BLASTN alignment is performed. Such pair-wise BLASTN alignments between a query nucleic acid sequence and a subject nucleic acid sequence are performed by using the default settings of the BLASTN algorithm available on the National Center for Biotechnology Institute's website with the filter for low complexity regions turned off. Importantly, a query sequence may be described by a nucleic acid sequence identified in one or more claims herein.

Nucleic acid sequences which may be useful, and included, in the compositions and related methods of the disclosure may have between about 85% to about 100%, about 90% to about 100%, about 95% to about 100%, about 91%, about 92%, about 93%, about 94%, about 95%, about 96%, about 97%, about 98%, about 99% and about 100% identity to the nucleic acid sequences identified in the disclosure (e.g., nucleic acids encoding an antibody heavy chain or antibody light chain). In the disclosure, percent identity between the nucleic acid sequences described may include any discrete subrange of the percent identity ranges recited above (e.g., any range of integer values within a particular range or discrete subvalues within a particular range).

"Percent identity" between a query amino acid sequence and a subject amino acid sequence is the "Identities" value, expressed as a percentage, that is calculated by the BLASTP algorithm when a subject amino acid sequence has 100% query coverage with a query amino acid sequence after a pair-wise BLASTP alignment is performed. Such pair-wise BLASTP alignments between a query amino acid sequence and a subject amino acid sequence are performed by using the default settings of the BLASTP algorithm available on the National Center for Biotechnology Institute's website with the filter for low complexity regions turned off. Importantly, a query sequence may be described by an amino acid sequence identified in one or more claims herein.

The amino acid sequences which may be useful, and included, in compositions and related methods of the disclosure may have between about 85% to about 100%, about 90% to about 100%, about 95% to about 100%, about 91%, about 92%, about 93%, about 94%, about 95%, about 96%, about 97%, about 98%, about 99% and about 100% identity to the amino acid sequences identified in the disclosure (e.g., to an antibody heavy chain or antibody light chain). In the disclosure, percent identity between the amino acid sequences described may includes any discrete subrange of the percent identity ranges recited above (e.g., any range of integer values within a particular range or discrete subvalues within a particular range).

The terms "peptide", "polypeptide", "protein" and "peptide chain" each refer to a molecule comprising two or more amino acid residues. A peptide may be monomeric or polymeric.

It is well recognized in the art that certain amino acid substitutions are regarded as being "conservative" Amino acids are divided into groups based on common side-chain properties and substitutions within groups that maintain all or substantially all of the binding affinity of the antigen binding protein are regarded as conservative substitutions. See Table 6. The antigen binding proteins disclosed herein can comprise such "conservative" amino acid substitutions.

TABLE 6

| Side chain | Members |
| --- | --- |
| Hydrophobic | met, ala, val, leu, ile |
| Neutral hydrophilic | cys, ser, thr |
| Acidic | asp, glu |
| Basic | asn, gln, his, lys, arg |
| Residues that influence chain orientation | gly, pro |
| Aromatic | trp, tyr, phe |

The term "pharmaceutical composition" as used herein means a composition suitable for administration to a patient.

The pharmaceutical compositions described herein may comprise purified preparations of an antibody as described herein.

For example, the pharmaceutical preparation may comprise a purified preparation of an antibody as described herein in combination with a pharmaceutically acceptable carrier.

Typically, such pharmaceutical compositions comprise a pharmaceutically acceptable carrier as known and called for by acceptable pharmaceutical practice. Examples of such carriers include sterilized carriers, such as saline, Ringers solution, or dextrose solution, optionally buffered with suitable buffers to a pH within a range of 5 to 8.

Pharmaceutical compositions may be administered by injection or infusion (e.g., intravenous, intraperitoneal, intradermal, subcutaneous, intramuscular, or intraportal). Such compositions are suitably free of visible particulate matter. Pharmaceutical compositions may comprise between 1 mg to 10 g of antigen binding protein, for example, between 5 mg and 1 g of antigen binding protein. Alternatively, the composition may comprise between 5 mg and 500 mg of antigen binding protein, for example, between 5 mg and 50 mg.

Methods for the preparation of such pharmaceutical compositions are well known to those skilled in the art. Pharmaceutical compositions may comprise between 1 mg to 10 g of antigen binding protein in unit dosage form, optionally together with instructions for use. Pharmaceutical compositions may be lyophilized (freeze dried) for reconstitution prior to administration according to methods well known or apparent to those skilled in the art. Where antibodies have an IgG$_1$ isotype, a chelator of copper, such as citrate (e.g., sodium citrate) or EDTA or histidine, may be added to the pharmaceutical composition to reduce the degree of copper-mediated degradation of antibodies of this isotype. Pharmaceutical compositions may also comprise a solubilizer, such as arginine, a surfactant/anti-aggregation agent such as polysorbate 80, and an inert gas such as nitrogen to replace vial headspace oxygen.

The term "therapeutically effective amount" as used herein means an amount of an agent (such as an antibody or a pharmaceutical composition), which provides a therapeutic benefit in the treatment or management of one or more symptoms of a condition to be treated (such as asthma, severe eosinophilic asthma, uncontrolled eosinophilic asthma, eosinophilic asthma, sub-eosinophilic asthma, chronic obstructive pulmonary disease, eosinophilic granulomatosis with polyangiitis (EGPA), hypereosinophilic syndrome and nasal polyposis). Examples of such treatment or management of one or more symptoms of asthma—including severe eosinophilic asthma, uncontrolled eosinophilic asthma, eosinophilic asthma or sub-eosinophilic asthma— include 1) a reduction of the frequency of asthma exacerbations; 2) a reduction in the time to first clinically significant exacerbation requiring oral or systemic corticosteroids, hospitalisation, and/or emergency department (ED) visits; 3) a reduction in the frequency of exacerbations requiring hospitalization (including intubation and admittance to an intensive care unit) or ED visits; 4) a reduction in the time to first exacerbation requiring hospitalization or ED visit; 5) a change from baseline in clinic pre-bronchodilator FEV$_1$; 6) a change from baseline in clinic post-bronchodilator FEV$_1$; 7) a change from baseline in an Asthma Control Questionnaire (ACQ) score; 8) improved lung function as assessed by spirometry (e.g., vital capacity (VC), forced vital capacity (FVC), forced expiratory volume (FEV) at timed intervals of 0.5, 1.0 (FEV$_1$), 2.0, and 3.0 seconds, forced expiratory flow 25-75% (FEF 25-75) and maximal voluntary ventilation (MVV) total lung capacity, idal volume, residual volume, expiratory reserve volume, inspiratory reserve volume, inspiratory capacity, inspiratory vital capacity, vital capacity, functional residual capacity, residual volume expressed as percent of total lung capacity, alveolar gas volume, actual volume of the lung including the volume of the conducting airway, forced vital capacity, etc.); and 9) a reduction in asthma exacerbations requiring steroids for control (such as oral steroids or steroids—like prednisone, prednisolone etc.—administered by any route). Such a reduction in asthma exacerbations requiring steroids for control may be an approximately 50% reduction in exacerbations requiring steroids (e.g., oral steroids).

Therapeutically effective amounts and treatment regimes are generally determined empirically and may be dependent on factors, such as the age, weight, and health status of the patient and disease or disorder to be treated. Such factors are within the purview of the attending physician.

The dosage of antigen binding protein administered to a subject is generally between 1 μg/kg to 150 mg/kg, between 0.1 mg/kg and 100 mg/kg, between 0.5 mg/kg and 50 mg/kg, between 1 and 25 mg/kg, between about 0.3 mg/kg and about 3 mg/kg or between 1 and 10 mg/kg of the subject's body weight. For example, the dose may be 10 mg/kg, 30 mg/kg, or 60 mg/kg. The dose may also be from 10 mg/kg to 110 mg/mg 15 mg/kg to 25 mg/kg or 15 mg/kg to 100 mg/kg. The antigen binding protein may be administered, for example, parenterally, subcutaneously, intravenously, or intramuscularly. Doses may also be administered on a per subject basis such as about 20 mg per subject to about 750 mg per subject, about 75 mg per subject to about 750 mg per subject, about 20 mg per subject to about 200 mg per subject. The dose may be any discrete subrange with these dosage ranges. For example, the dose (such as a dose of mepolizumab or a pharmaceutical composition comprising mepolizumab) may also be administered subcutaneously on a per subject basis such as about 100 mg per subject (e.g., once every four weeks), or 300 mg per subject (or other doses administered may be subcutaneously with provided approximately the same, or comparable, bioavailability is achieved as with intravenous administration—e.g., three doses of 100 mg per subject to achieve a total dose administered subcutaneously of 300 mg per subject).

Ranges provided herein, of any type, include all values within a particular range described and values about an endpoint for a particular range.

If desired, the effective daily dose of a therapeutic composition may be administered as two, three, four, five, six or more doses administered separately at appropriate intervals throughout the day, optionally, in unit dosage forms.

The administration of a dose may be by slow continuous infusion over a period of from 2 to 24 hours, such as of from 2 to 12 hours, or from 2 to 6 hours. Such an administration may result in reduced side effects.

The administration of a dose may be repeated one or more times as necessary, for example, three times daily, once every day, once every 2 days, once a week, once a every 14 days, once a month, once every 3 months, once every 4 months, once every 6 months, or once every 12 months. The antigen binding proteins may be administered by maintenance therapy, for example once a week for a period of 6 months or more. The antigen binding proteins may be administered by intermittent therapy, for example, for a period of 3 to 6 months and then no dose for 3 to 6 months, followed by administration of antigen binding proteins again for 3 to 6 months, and so on, in a cycle.

For example, the dose may be administered subcutaneously, once every 14 or 28 days, in the form of multiple doses on each day of administration. In one embodiment, the dosage of the composition is 100 mg once every 4 weeks (28 days).

The antigen binding protein may be administered to the subject in such a way as to target therapy to a particular site.

The antigen binding protein in the methods of the disclosure may be used in combination with one or more other therapeutically active agents, such as antibodies or small molecule inhibitors By the term "treating" and grammatical variations thereof as used herein, is meant therapeutic therapy. In reference to a particular condition, treating means: (1) to ameliorate the condition of one or more of the biological manifestations of the condition, (2) to interfere with a) one or more points in the biological cascade that leads to or is responsible for the condition or b) one or more of the biological manifestations of the condition, (3) to alleviate one or more of the symptoms, effects or side effects associated with the condition or treatment thereof, (4) to slow the progression of the condition or one or more of the biological manifestations of the condition or (5) to prevent the onset of one or more of the biological manifestations of the condition. Prophylactic therapy is also contemplated thereby. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

The terms "individual", "subject" and "patient" are used herein interchangeably. The subject is typically a human. The subject may also be a mammal, such as a mouse, rat, or primate (e.g., a marmoset or monkey). The subject can be a non-human animal. The antigen binding proteins, compositions and methods of the disclosure also have veterinary use. The subject to be treated may be a farm animal, for example, a cow or bull, sheep, pig, ox, goat or horse, or may be a domestic animal such as a dog or cat. The animal may be any age, or a mature adult animal.

Treatment can be therapeutic, prophylactic or preventative. The subject will be one who is in need thereof. Those in need of treatment may include individuals already suffering from a particular medical disease, in addition to those who may develop the disease in the future.

Thus, the methods, antigen binding proteins and compositions of the disclosure described herein can be used for prophylactic treatment or preventative treatment if specified. In this case, methods, antigen binding proteins and compositions of the disclosure can be used to prevent or delay the onset of one or more aspects or symptoms of a disease. The subject can be asymptomatic. The subject may have a genetic predisposition to the disease. A prophylactically effective amount of the antigen binding protein is administered to such an individual. A prophylactically effective amount is an amount which prevents or delays the onset of one or more aspects or symptoms of a disease described herein.

The methods, antigen binding proteins and compositions of the disclosure need not affect a complete cure, or eradicate every symptom or manifestation of the disease to constitute a viable therapeutic treatment. As is recognised in the art, drugs employed as therapeutic agents in methods of treatment may reduce the severity of a given disease state, but need not abolish every manifestation of the disease to be regarded as useful therapeutic agents. Similarly, a prophylactically administered treatment need not be completely effective in preventing the onset of a disease in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur (for example by delaying the onset of the disease) or worsen in a subject, is sufficient.

One aspect of the disclosure is a composition comprising an antibody having a heavy chain amino acid sequence as shown in SEQ ID NO: 1 and a light chain amino acid sequence as shown in SEQ ID NO: 2, or an antibody variant having a heavy chain amino acid sequence at least 90% identical to the heavy chain amino acid sequence and/or a light chain amino acid sequence at least 90% identical to the light chain amino acid sequence, wherein the composition comprises: ≤80% acidic antibody variants.

In one embodiment the composition has: a) ≥0.70 IL-5 specific antigen binding; and/or b) ≥70% FcRn binding. IL-5 specific antigen binding, such as binding to human IL-5 comprising the amino acid sequence of SEQ ID NO: 11, can be measured using standard assays, such as surface plasmon resonance (e.g., BIACORE™), that are well known in the art. FcRn binding can similarly be measured using standard assays, such as surface plasmon resonance (e.g., BIACORE™), that are well known in the art.

In another embodiment a) the specific antigen binding is in the range of from 0.70 to 1.30; and/or b) the FcRn binding is in the range of from 70% to 130%. In some embodiments the specific antigen binding may be in the range of about 0.9 to 1.1, 0.75 to about 1, about 0.7 to about 0.8, about 0.7, about 0.91 to about 0.95, about 0.994 to about 0.997 or about 0.7 to about 0.9. In some embodiments the FcRn binding is in the range of from about 70% to about 100%, about 100% to about 130%, about 70%, about 80%, about 90%, about 100%, about 110%, about 120%, about 80% to about 90%, about 80% to about 100%, about 100% to about 110%, about 110% to about 120%, about 120% to about 130%, about 80% to about 120% and about 90% to about 110%.

In one embodiment, the composition comprises: ≤80% acidic antibody variants. For example, the composition may comprise ≤75%, ≤70%, ≤65%, ≤60%, ≤55%, ≤50%, or ≤45% acidic antibody variants.

In another embodiment the composition comprises: ≤35% deamidated antibody variants.

In another embodiment the composition comprises: ≤25% deamidated antibody variants at N31 of the light chain amino acid sequence. For example, the composition may comprise ≤22.5%, ≤20%, ≤17.5%, ≤15%, ≤12.5, ≤10%, or ≤7.5% deamidated antibody variants at N31 of the light chain amino acid sequence.

In another embodiment the composition comprises: ≤35% deamidated antibody variants at N386 of the heavy chain amino acid sequence. For example, the composition may comprise ≤32.5%, ≤30%, ≤25.5%, or ≤20%, ≤17.5%, ≤15%, ≤12.5%, ≤10%, or ≤7.5% deamidated antibody variants at N386 of the heavy chain amino acid sequence.

In another embodiment the composition comprises: ≤55% oxidised antibody variants.

In another embodiment the composition comprises: ≤55% oxidised antibody variant at any one or a combination of: a) M64 of the heavy chain amino acid sequence; b) M254 of the heavy chain amino acid sequence; and/or c) M430 of the heavy chain amino acid sequence. For example, the composition may comprise ≤50%, ≤45%, ≤40%, ≤35%, ≤30%, or ≤25%, ≤20%, ≤15%, ≤10%, or ≤5% oxidised antibody variants at M64, M254, and/or M430 of the heavy chain amino acid sequence.

In another embodiment the composition comprises: ≤3% oxidised antibody variants at W52 of the heavy chain amino acid sequence. For example, the composition may comprise ≤2.5%, ≤2%, ≤1.5%, ≤1%, ≤0.5%, ≤0.4%, ≤0.3%, ≤0.25%, ≤0.2%, ≤0.15%, or ≤0.1% oxidised antibody variants at W52 of the heavy chain amino acid sequence.

In another embodiment a deamidated antibody variant amount and/or an oxidised variant amount, is determined by peptide mapping LC-MS/MS.

In another embodiment the composition comprises: ≤20% aggregated antibody variants. For example, the composition may comprise ≤17.5%, ≤15%, ≤12.5, ≤10%, ≤7.5%, ≤5%, or ≤4%, aggregated variant. The compositions may comprise less than or equal to 3%, 2%, 1% or 0.5% aggregated antibody. The composition may comprise greater than or equal to 98% monomeric antibody.

In another embodiment the aggregated antibody variant comprises a dimer. Such an aggregated antibody can comprise two antibody molecules (e.g., two IgG$_1$ antibody molecules).

In another embodiment the aggregated antibody variant amount is determined by size exclusion chromatography (SEC). Methods for performing size exclusion chromatography and measuring protein molecule size are well known in the art.

In another embodiment the composition comprises: ≥50% heavy chain amino acid sequence C-terminal lysine K449 deleted antibody variants. For example, the composition may comprise ≥60%, ≥70%, ≥75, ≥80%, ≥85%, ≥90%, or ≥95% heavy chain amino acid sequence C-terminal lysine K449 deleted antibody variants.

In another embodiment the composition comprises: ≥50% heavy chain amino acid sequence pyro-glutamate N-terminal antibody variants. For example, the composition may comprise ≥60%, ≥70%, ≥75, ≥80%, ≥85%, ≥90%, or ≥95% heavy chain amino acid sequence pyro-glutamate N-terminal antibody variants.

In another embodiment the composition comprises Host Cell Protein (HCP). The HCP may be CHO cell derived. HCP is a process-related impurity in contrast to mepolizumab product-related substances (i.e. mepolizumab plus mepolizumab variants). Industry standard acceptable limits for HCP can be up to 100 ppm (equal to 100 ng/mg). HCP content in a composition described herein may be ≤50 ng/mg, ≤40 ng/mg, ≤30 ng/mg, or ≤20 ng/mg. For example, HCP content of the composition may be ≤10 ng/mg. In a particular embodiment, HCP content of the composition may be ≤5 ng/mg or ≤2 ng/mg.

Another aspect of the disclosure is a composition comprising an antibody having a heavy chain amino acid sequence as shown in SEQ ID NO: 1 and a light chain amino acid sequence as shown in SEQ ID NO: 2, or an antibody variant having a heavy chain amino acid sequence at least 90% identical to the heavy chain amino acid sequence and/or a light chain amino acid sequence at least 90% identical to the light chain amino acid sequence, wherein the composition comprises: ≤80% acidic antibody variants and ≤20% aggregated antibody variants.

Another aspect of the disclosure is a composition comprising an antibody having a heavy chain amino acid sequence as shown in SEQ ID NO: 1 and a light chain amino acid sequence as shown in SEQ ID NO: 2, or an antibody variant having a heavy chain amino acid sequence at least 90% identical to the heavy chain amino acid sequence and/or a light chain amino acid sequence at least 90% identical to the light chain amino acid sequence, wherein the composition comprises: ≤25% deamidated antibody variants at N31 of the light chain amino acid sequence; and ≤20% aggregated antibody variants.

Another aspect of the disclosure is a composition comprising an antibody having a heavy chain amino acid sequence as shown in SEQ ID NO: 1 and a light chain amino acid sequence as shown in SEQ ID NO: 2, or an antibody variant having a heavy chain amino acid sequence at least 90% identical to the heavy chain amino acid sequence and/or a light chain amino acid sequence at least 90% identical to the light chain amino acid sequence, wherein the composition comprises: ≤25% deamidated antibody variants at N31 of the light chain amino acid sequence; ≤55% oxidised antibody variants at M64 of the heavy chain amino acid sequence; ≤3% oxidised variants at W52 of the heavy chain amino acid sequence; and ≤20% aggregated antibody variants.

Another aspect of the disclosure is a composition comprising an antibody having a heavy chain amino acid sequence as shown in SEQ ID NO: 1 and a light chain amino acid sequence as shown in SEQ ID NO: 2, or an antibody variant having a heavy chain amino acid sequence at least 90% identical to the heavy chain amino acid sequence and/or a light chain amino acid sequence at least 90% identical to the light chain amino acid sequence, wherein the composition comprises: ≤25% deamidated antibody variants at N31 of the light chain amino acid sequence; ≤35% deamidated antibody variants at N386 of the heavy chain amino acid sequence; and ≤20% aggregated antibody variants.

Another aspect of the disclosure is a composition comprising an antibody having a heavy chain amino acid sequence as shown in SEQ ID NO: 1 and a light chain amino acid sequence as shown in SEQ ID NO: 2, or an antibody variant having a heavy chain amino acid sequence at least 90% identical to the heavy chain amino acid sequence and/or a light chain amino acid sequence at least 90% identical to the light chain amino acid sequence, wherein the composition comprises: ≤25% deamidated antibody variants at N31 of the light chain amino acid sequence; ≤35% deamidated antibody variants at N386 of the heavy chain amino acid sequence; ≤55% oxidised antibody variants at M64 of the heavy chain amino acid sequence, M254 of the heavy chain amino acid sequence, M430 of the heavy chain amino acid sequence; ≤3% oxidised antibody variants at W52 of the heavy chain amino acid sequence; and ≤20% aggregated antibody variants.

The compositions of the disclosure may further comprise a buffering agent selected from the group consisting of sodium phosphate dibasic heptahydrate, phosphate, citric acid, citrate, sodium phosphate, potassium phosphate, sodium citrate, and histidine, providing a pH of between 6.8 and 7.2 or a pH of from pH 6.2 to pH 6.6 with a pH value of 6.3 being preferred. The buffer in the compositions of the disclosure may be present in the range from about 10-30 mM, about 10-20 mM, about 20 mM or about 15.5 mM. For example, the buffer in the compositions of the disclosure is present at about 20 mM, or at about 15.5 mM sodium phosphate dibasic heptahydrate.

The compositions of the disclosure may comprise sodium phosphate dibasic heptahydrate and citric acid buffering agents providing a pH of from 6.2 to 6.6 inclusive with a pH value of 6.3 being preferred. The sodium phosphate dibasic heptahydrate buffering agent may be present in the range from about 15-16.4 mM and the citric acid buffering agent may be present in the range from about 3.8-4.9 mM. For example, the compositions of the disclosure may comprise about 15.5 mM sodium phosphate dibasic heptahydrate and about 4.5 mM citric acid monohydrate.

The compositions of the disclosure may further comprise a sugar. The compositions of the disclosure may further comprise sucrose. Sucrose may be present in the compositions of the disclosure in the range from about 5-20%; about 10-15%, about 11-13% or at about 12% weight by volume.

The compositions of the disclosure may further comprise polysorbate 80. Polysorbate 80 may be present in the range from about 0.01-0.1% weight by volume. For example, polysorbate 80 may be present in the compositions of the disclosure at about 0.02% weight by volume, or at about 0.05% weight by volume.

The compositions of the disclosure may further comprise EDTA. EDTA may be present in the range from about 0.01-0.1 mM. For example, EDTA may be present at about 0.05 mM.

In one embodiment, the compositions of the disclosure further comprise 20 mM sodium phosphate dibasic heptahydrate, 12% weight of sucrose to volume and 0.05% weight of polysorbate 80 to volume.

In another embodiment, the compositions of the disclosure further comprise 15.5 mM sodium phosphate dibasic, 3.9 mM citric acid monohydrate, 12% weight of sucrose to volume, 0.02% weight of polysorbate 80 to volume and 0.05 mM EDTA.

The compositions of the disclosure may comprise an aqueous liquid formulation at pH 6.2 containing 16.1 mM sodium phosphate dibasic heptahydrate, 3.9 mM citric acid monohydrate, 12% weight of sucrose to volume, 0.02% weight of polysorbate 80 to volume and 0.05 mM EDTA.

The compositions of the disclosure may comprise an aqueous liquid formulation at pH 6.2 containing 15.2 mM sodium phosphate dibasic heptahydrate, 4.8 mM citric acid monohydrate, 12% weight of sucrose to volume, 0.02% weight of polysorbate 80 to volume and 0.05 mM EDTA.

The compositions of the disclosure may comprise an aqueous liquid formulation at pH 6.4 containing 15.8 mM sodium phosphate dibasic heptahydrate, 4.2 mM citric acid monohydrate, 12% weight of sucrose to volume, 0.02% weight of polysorbate 80 to volume and 0.05 mM EDTA.

The compositions of the disclosure may comprise an aqueous liquid formulation at pH 6.6 containing 16.3 mM sodium phosphate dibasic heptahydrate, 3.7 mM citric acid monohydrate, 12% weight of sucrose to volume, 0.02% weight of polysorbate 80 to volume and 0.05 mM EDTA.

The compositions of the disclosure may comprise an aqueous liquid formulation at pH 6.3 containing 15.5 mM sodium phosphate dibasic heptahydrate, 4.5 mM citric acid monohydrate, 12% weight of sucrose to volume, 0.02% weight of polysorbate 80 to volume and 0.05 mM EDTA. Importantly, the tangential filtration and ultrafiltration exchange step of Example 1 below may be adjusted to produce the compositions of the disclosure, such as a composition of the disclosure comprising 15.5 mM sodium phosphate dibasic heptahydrate, 4.5 mM citric citric acid monohydrate, 12% weight to volume sucrose, 0.02% weight to volume polysorbate 80, 0.05 mM EDTA at a pH of 6.3—or other such liquid formulations.

Another aspect of the disclosure is a composition comprising a purified preparation of a monoclonal antibody and a buffering agent, wherein the composition is at a pH from 6.8 to 7.2, wherein the buffering agent is histidine, phosphate, citric acid, citrate or a salt thereof, wherein the purified preparation comprises the isoforms represented by peak 65, peak 78, peak 88, peak 92, the main peak and peak 112 shown in FIG. 1, wherein the antibody comprises a heavy chain amino acid sequence having at least 90% identity to the amino acid sequence of SEQ ID NO: 1 and a light chain amino acid sequence having at least 90% identity to the amino acid sequence of SEQ ID NO: 2, and wherein the antibody is produced by a Chinese Hamster Ovary cell. In the composition the heavy chain may comprise an amino acid sequence having at least 95%, 96%, 96.88%, 97%, 98% or 99% identity to the amino acid sequence of SEQ ID NO: 1. In the composition the light chain may comprise an amino acid sequence having at least 98%, 98.63 or 99% identity to the amino acid sequence of SEQ ID NO: 2.

In one embodiment the buffering agent is at least one selected from the group consisting of sodium phosphate dibasic heptahydrate, phosphate, citric acid and citrate.

In another embodiment the buffering agent is sodium phosphate, potassium phosphate, or sodium citrate.

In another embodiment the composition further comprises a sugar, a carbohydrate and/or a salt.

In another embodiment the composition comprises sucrose.

Another aspect of the disclosure is a composition comprising a purified preparation of a monoclonal antibody and a buffering agent, wherein the composition is at a pH from 6.8 to 7.2, wherein the buffering agent is phosphate or a salt thereof, wherein the purified preparation comprises the isoforms represented by peak 65, peak 78, peak 88, peak 92, the main peak and peak 112 shown in FIG. 1, wherein the antibody comprises a heavy chain amino acid sequence having at least 90% identity to the amino acid sequence of SEQ ID NO: 1 and a light chain amino acid sequence having at least 90% identity to the amino acid sequence of SEQ ID NO: 2, and wherein the antibody is produced by a Chinese Hamster Ovary cell.

In another embodiment the buffering agent is at least one selected from the group consisting of sodium phosphate dibasic heptahydrate, phosphate, citric acid and citrate.

In another embodiment the composition further comprises a sugar.

In another embodiment the sugar is sucrose.

In another embodiment the composition comprises polysorbate 80.

In another embodiment the composition comprises one selected from a first formulation of 20 mM sodium phosphate dibasic heptahydrate, 12% weight of sucrose to volume and 0.05% weight of polysorbate 80 to volume; and a second formulation of 15.5 mM sodium phosphate dibasic heptahydrate, 3.9 mM citric acid monohydrate, 12% weight of sucrose to volume, 0.02% weight of polysorbate 80 to volume and 0.05 mM EDTA; and a third formulation of 26 mM sodium phosphate dibasic heptahydrate, 15% weight of sucrose to volume and 0.065% weight of polysorbate 80 to volume. The composition may be at a pH between about 6.8 to about 7.2, about 6.1 to about 6.5 or about 6 to about 6.6.

In another embodiment the antibody has a dissociation constant equal to, or less than, about $3.5 \times 10^{-11}$ M for human interleukin-5 comprising the amino acid sequence shown in SEQ ID NO: 11.

Another aspect of the disclosure is a composition comprising a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2; and b) a main form of the antibody comprising greater than, or equal to, 50% of the protein in the composition as measured using capillary isoelectric focusing of the composition. The main form of the antibody may also comprise greater than, or equal to, 57.9%, 59.4%, and 60% of the protein in the composition as measured using capillary isoelectric focusing of the composition.

In another embodiment the main form of the antibody comprises at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220.

Another aspect of the disclosure is a composition comprising a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2; b) a main form of the antibody comprising greater than, or equal to, 50% of the protein in the composition as measured using capillary isoelectric focusing of the composition; and c) acidic forms of the antibody comprising about 20% to about 45% of the protein in the composition as measured using capillary isoelectric focusing of the composition. The acid forms of the antibody may also comprise greater than, or equal to, 37.6%, 37.8%, 38.4% and 39.8% of the protein in the composition as measured using capillary isoelectric focusing of the composition. The total acidic peak area determined by cIEF can be as high as 72% and still retain 0.74 IL-5 specific binding and 80% FcRn binding.

In another embodiment the acidic forms of the antibody comprise at least one selected from the group consisting of a peak 65 acidic form, a peak 78 acidic form, a peak 88 acidic form and a peak 92 acidic form.

In another embodiment the acidic forms of the antibody comprise at least one deamidated amino acid residue selected from the group consisting of a heavy chain amino acid residue deamidated at asparagine 299, a heavy chain amino acid residue deamidated at asparagine 317, a heavy chain amino acid residue deamidated at asparagine 386 and a light chain amino acid residue deamidated at asparagine 31. An acceptable level of deamidation on LC N31 is greater than or equal to 17%, or greater than or equal to 17.4% as measured by peptide mapping LC MS/MS). An acceptable level of deamidation on HC 386 is greater than or equal to 30% as measured by peptide mapping LC MS/MS). The acceptable upper level may be the level of a particular variant that allows the antibody molecules in the composition to retain antigen binding activity of about 0.70 to about 1.30 as measured by SPR and FcRn binding activity of about 70% to about 130% as measured by SPR or other antigen binding activity or FcRn binding activity values, or ranges, disclosed herein.

In another embodiment the acidic forms of the antibody comprise at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220. Acceptable levels of oxidation on the heavy chain residues of the antibody as measured by peptide mapping LC-MS/MS may be about 50% for HC M64, M254, and M430 and about 3% for HC W52. The acceptable upper level may be the level of a particular variant that allows the antibody molecules in the composition to retain antigen binding activity of about 0.70 to about 1.30 as measured by SPR and FcRn binding activity of about 70% to about 130% as measured by SPR or other antigen binding activity or FcRn binding activity values, or ranges, disclosed herein.

In another embodiment the main form of the antibody comprises at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220; and the acidic forms of the antibody comprise at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220.

Another aspect of the disclosure is a composition comprising a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2; b) a main form of the antibody comprising greater than, or equal to, 50% of the protein in the composition as measured using capillary isoelectric focusing of the composition; and c) a basic form of the antibody comprising about 1% to about 15% of the protein in the composition as measured using capillary isoelectric focusing of the composition. The basic form of the antibody may also comprise greater than, or equal to, 2.2% and 2.3% of the protein in the composition as measured using capillary isoelectric focusing of the composition.

In another embodiment the basic form of the antibody comprises a peak 112 basic form.

In another embodiment the basic form of the antibody comprises a heavy chain having a carboxy terminal residue that is glycine 448.

In another embodiment the basic forms of the antibody comprise at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220.

In another embodiment the main form of the antibody comprises at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220; and the basic forms of the antibody comprise at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a heavy chain amino acid residue oxidized at cysteine 222.

Another aspect of the disclosure is a composition comprising a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2; b) a main form of the antibody comprising greater than, or equal to, 50% of the protein in the composition as measured using capillary isoelectric focusing of the composition; c) acidic forms of the antibody comprising about 20% to about 45% of the protein in the composition as measured using capillary isoelectric focusing of the composition; and d) a basic form of the antibody comprising about 1% to about 15% of the protein in the composition as measured using capillary isoelectric focusing of the composition.

In another embodiment the acidic forms of the antibody comprise at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220; and the basic forms of the antibody comprise at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a heavy chain amino acid residue oxidized at cysteine 222.

In another embodiment the main form of the antibody comprises at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220; the acidic forms of the antibody comprise at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220; and wherein the basic forms of the antibody comprise at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220.

Another aspect of the disclosure is a composition comprising a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2; and b) deamidated forms of the antibody comprising at least one selected from the group consisting of a heavy chain amino acid residue deamidated at asparagine 299, a heavy chain amino acid residue deamidated at asparagine 317, a heavy chain amino acid residue deamidated at asparagine 386 and a light chain amino acid residue deamidated at asparagine 31.

Another aspect of the disclosure is a composition comprising a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2; and b) oxidized forms of the antibody comprising at least one selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220.

Another aspect of the disclosure is a composition comprising a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2; b) deamidated forms of the antibody comprising at least one selected from the group consisting of a heavy chain amino acid residue deamidated at asparagine 299, a heavy chain amino acid residue deamidated at asparagine 317, a heavy chain amino acid residue deamidated at asparagine 386 and a light chain amino acid residue deamidated at asparagine 31; and c) oxidized forms of the antibody comprising at least one selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220.

Another aspect of the disclosure is a composition comprising a) an anti-IL-5 antibody comprising a heavy chain variable region having the CDRH1 amino acid sequence shown in SEQ ID NO: 5, the CDRH2 amino acid sequence shown in SEQ ID NO: 6, and the CDRH3 amino acid sequence shown in SEQ ID NO: 7; and a light chain variable region having the CDRL1 amino acid sequence shown in SEQ ID NO: 8, the CDRL2 amino acid sequence shown in SEQ ID NO: 9, and the CDRL3 amino acid sequence shown in SEQ ID NO: 10; and b) deamidated forms of the antibody comprising a light chain amino acid residue deamidated at asparagine 31. In the composition CDRH2 may comprise an amino acid sequence having at least 85% or 87.5% identity to the amino acid sequence of SEQ ID NO: 6. In the composition CDRL1 may comprise an amino acid sequence having at 93%, 94% or 94.11% identity to the amino acid sequence of SEQ ID NO: 8.

Another aspect of the disclosure is a composition comprising a) an anti-IL-5 antibody comprising a heavy chain variable region having the CDRH1 amino acid sequence shown in SEQ ID NO: 5, the CDRH2 amino acid sequence shown in SEQ ID NO: 6, and the CDRH3 amino acid sequence shown in SEQ ID NO: 7; and a light chain variable region having the CDRL1 amino acid sequence shown in SEQ ID NO: 8, the CDRL2 amino acid sequence shown in SEQ ID NO: 9, and the CDRL3 amino acid sequence shown in SEQ ID NO: 10; and b) oxidized forms of the antibody comprising a heavy chain amino acid residue oxidized at methionine 64.

Another aspect of the disclosure is a composition comprising a) an anti-IL-5 antibody comprising a heavy chain variable region having the CDRH1 amino acid sequence shown in SEQ ID NO: 5, the CDRH2 amino acid sequence shown in SEQ ID NO: 6, and the CDRH3 amino acid sequence shown in SEQ ID NO: 7; and a light chain variable region having the CDRL1 amino acid sequence shown in SEQ ID NO: 8, the CDRL2 amino acid sequence shown in SEQ ID NO: 9, and the CDRL3 amino acid sequence shown in SEQ ID NO: 10; and b) oxidized forms of the antibody comprising a heavy chain amino acid residue oxidized at methionine 64; and c) deamidated forms of the antibody comprising a light chain amino acid residue deamidated at asparagine 31.

Another aspect of the disclosure is a composition comprising a) an anti-IL-5 antibody comprising a heavy chain variable region sequence having the amino acid sequence shown in SEQ ID NO: 3 and a light chain variable region sequence having the amino acid sequence shown in SEQ ID NO: 4; and b) deamidated forms of the antibody comprising a light chain amino acid residue deamidated at asparagine 31. In the composition the heavy chain variable region may comprise an amino acid sequence having at least 90%, 95% or 95.57% identity to the amino acid sequence of SEQ ID NO: 3. In the composition the light chain variable region may comprise an amino acid sequence having at least 90%, 98% or 98.31% identity to the amino acid sequence of SEQ ID NO: 3.

Another aspect of the disclosure is a composition comprising a) an anti-IL-5 antibody comprising a heavy chain variable region sequence having the amino acid sequence shown in SEQ ID NO: 3 and a light chain variable region sequence having the amino acid sequence shown in SEQ ID NO: 4; and b) oxidized forms of the antibody comprising at least one selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85 and a light chain amino acid residue oxidized at methionine 4.

Another aspect of the disclosure is a composition comprising a) an anti-IL-5 antibody comprising a heavy chain variable region sequence having the amino acid sequence shown in SEQ ID NO: 3 and a light chain variable region sequence having the amino acid sequence shown in SEQ ID NO: 4; b) deamidated forms of the antibody comprising a light chain amino acid residue deamidated at asparagine 31; and c) oxidized forms of the antibody comprising at least one selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85 and a light chain amino acid residue oxidized at methionine 4.

In another embodiment the total protein concentration is about 75 mg/mL. The total protein concentration may also be about any pair of values, or single value in the range of about 75 mg/mL to about 150 mg/mL such as about 75 mg/mL to about 100 mg/mL, about 67.3 to about 87.5 mg/mL, about 76 g protein/L to about 82 g protein/L, about 46 g protein/L to about 66 g protein/L or about 100 mg/mL. In the compositions the purity of the anti-human-IL-5 antibodies in the sample is greater than, or equal to, 97.0%, 96%, 95%, or 80%, 85%.

In another embodiment the composition further comprises a) a main form of the antibody comprising greater than, or equal to, 50% of the protein in the composition as measured using capillary isoelectric focusing of the composition.

In another embodiment the composition further comprises a) a main form of the antibody comprising greater than, or equal to, 50% of the protein in the composition as measured using capillary isoelectric focusing of the composition; and b) acidic forms of the antibody comprising about 20% to about 45% of the protein in the composition as measured using capillary isoelectric focusing of the composition.

In another embodiment the composition further comprises a) a main form of the antibody comprising greater than, or equal to, 50% of the protein in the composition as measured using capillary isoelectric focusing of the composition; and b) a basic form of the antibody comprising about 1% to about 15% of the protein in the composition as measured using capillary isoelectric focusing of the composition.

In another embodiment the composition of further comprises a) a main form of the antibody comprising greater than, or equal to, 50% of the protein in the composition as measured using capillary isoelectric focusing of the composition; b) acidic forms of the antibody comprising about 20% to about 45% of the protein in the composition as measured using capillary isoelectric focusing of the composition; and c) a basic form of the antibody comprising about 1% to about 15% of the protein in the composition as measured using capillary isoelectric focusing of the composition.

Another aspect of the disclosure is a composition comprising a population of anti-IL-5 antibodies having a) a modified form of the antibody heavy chain amino acid sequence shown in SEQ ID NO: 1 comprising at least one amino acid residue modification selected from the group consisting of an amino terminal pyroglutamate residue at amino acid residue 1, a carboxy terminal glycine amino acid residue at amino acid residue 448, a deamidated asparagine residue at position 299, a deamidated asparagine residue at position 317, a deamidated asparagine residue at position 386, an oxidized tryptophan residue at position 52, an oxidized methionine residue at position 64, an oxidized methionine residue at position 82, an oxidized methionine residue at position 85, an oxidized cysteine residue at position 222, an oxidized methionine at position 254, an oxidized methionine at position 360 and an oxidized methionine residue at position 430; and b) a modified form of the antibody light chain amino acid sequence shown in SEQ ID NO: 2 comprising at least one amino acid residue modification selected from the group consisting of a deamidated asparagine residue at amino acid residue 31, an oxidized methionine residue at position 4 and an oxidized cysteine residue at position 220.

In another embodiment the composition comprises a) about greater than or equal to 92% of the population comprises an amino terminal pyroglutamate residue at amino acid residue 1 of the antibody heavy chain, b) about greater than or equal to 90% of the population comprises a carboxy terminal glycine amino acid residue at amino acid residue 448 of the antibody heavy chain, c) less than or equal to 6.0% of the population comprises a deamidated asparagine residue at position 386 of the antibody heavy chain; d) about less than or equal to 1.5% of the population comprises an oxidized methionine residue at position 64 of the antibody heavy chain, e) about less than or equal to 4.5% of the population comprises an oxidized methionine at position 254 of the antibody heavy chain, f) about less than or equal to 0.8% of the population comprises an oxidized methionine residue at position 430 of the antibody heavy chain, and g) about less than or equal to 6.6% of the population comprises a deamidated asparagine residue at amino acid residue 31 of the antibody light chain.

In another embodiment the composition comprises a) about 92% to about 99% of the population comprises an amino terminal pyroglutamate residue at amino acid residue 1 of the antibody heavy chain, b) about 95% to about 99.5% of the population comprises a carboxy terminal glycine amino acid residue at amino acid residue 448 of the antibody heavy chain, c) about 0.3% to about 1.5% of the population comprises a deamidated asparagine residue at position 317 of the antibody heavy chain, d) about 1.5% to about 4.5% of the population comprises a deamidated asparagine residue at position 386 of the antibody heavy chain; e) about 0.5% to about 1.5% of the population comprises an oxidized methionine residue at position 64 of the antibody heavy chain, f) about 0.2% to about 1.5% of the population comprises an oxidized methionine residue at position 82 of the antibody heavy chain or an oxidized methionine residue at position 85 of the antibody heavy chain, g) about 2.5% to about 3.5% of the population comprises an oxidized methionine at position 254 of the antibody heavy chain, h) about 0.4% to about 0.8% of the population comprises an oxidized methionine residue at position 430 of the antibody heavy chain, i) about 3.3% to about 6.6% of the population comprises a deamidated asparagine residue at amino acid residue 31 of the antibody light chain, and j) about 0.1% to about 1% of the population comprises an oxidized methionine residue at position 4 of the antibody light chain.

In another embodiment the composition comprises: a) about 93.7% to about 98.6% of the population comprises an amino terminal pyroglutamate residue at amino acid residue 1 of the antibody heavy chain, b) about 97.6% to about 99.2% of the population comprises a carboxy terminal glycine amino acid residue at amino acid residue 448 of the antibody heavy chain, c) about 0.4% to about 1.2% of the population comprises a deamidated asparagine residue at position 317 of the antibody heavy chain, d) about 1.6% to about 4.2% of the population comprises a deamidated asparagine residue at position 386 of the antibody heavy chain; e) about 0.7% to about 0.9% of the population comprises an oxidized methionine residue at position 64 of the antibody heavy chain, f) about 0.3% to about 1.1% of the population comprises an oxidized methionine residue at position 82 of the antibody heavy chain or an oxidized methionine residue at position 85 of the antibody heavy chain, g) about 2.6% to about 3.3% of the population comprises an oxidized methionine at position 254 of the antibody heavy chain, h) about 0.5% to about 0.7% of the population comprises an oxidized methionine residue at position 430 of the antibody heavy chain, i) about 3.4% to about 6.5% of the population comprises a deamidated asparagine residue at amino acid residue 31 of the antibody light chain, and j) about 0.2% to about 0.8% of the population comprises an oxidized methionine residue at position 4 of the antibody light chain.

Another aspect of the disclosure is a composition comprising a population of anti-IL-5 antibodies having a) a modified form of the antibody heavy chain amino acid sequence shown in SEQ ID NO: 1 comprising at least one amino acid residue modification selected from the group consisting of a deamidated asparagine residue at position 299, a deamidated asparagine residue at position 317, a deamidated asparagine residue at position 386, an oxidized tryptophan residue at position 52, an oxidized methionine residue at position 64, an oxidized methionine residue at position 82, an oxidized methionine residue at position 85, an oxidized cysteine residue at position 222, an oxidized methionine at position 254, an oxidized methionine at position 360 and an oxidized methionine residue at position 430; and b) a modified form of the antibody light chain amino acid sequence shown in SEQ ID NO: 2 comprising at least one amino acid residue modification selected from the group consisting of a deamidated asparagine residue at amino acid residue 31, an oxidized methionine residue at position 4 and an oxidized cysteine residue at position 222.

In another embodiment the composition comprises: a) about 0.3% to about 1.5% of the population comprises a deamidated asparagine residue at position 317 of the antibody heavy chain, b) about 1.5% to about 4.5% of the population comprises a deamidated asparagine residue at position 386 of the antibody heavy chain; c) about 0.5% to about 1.5% of the population comprises an oxidized methionine residue at position 64 of the antibody heavy chain, d) about 0.2% to about 1.5% of the population comprises an oxidized methionine residue at position 82 of the antibody heavy chain or an oxidized methionine residue at position 85 of the antibody heavy chain, e) about 2.5% to about 3.5% of the population comprises an oxidized methionine at position 254 of the antibody heavy chain, f) about 0.4% to about 0.8% of the population comprises an oxidized methionine residue at position 430 of the antibody heavy chain, g) about 3.3% to about 6.6% of the population comprises a deamidated asparagine residue at amino acid residue 31 of the antibody light chain, and h) about 0.1% to about 1% of the population comprises an oxidized methionine residue at position 4 of the antibody light chain.

In another embodiment the composition comprises: a) about 0.4% to about 1.2% of the population comprises a deamidated asparagine residue at position 317 of the antibody heavy chain, b) about 1.6% to about 4.2% of the population comprises a deamidated asparagine residue at position 386 of the antibody heavy chain; c) about 0.7% to about 0.9% of the population comprises an oxidized methionine residue at position 64 of the antibody heavy chain, d) about 0.3% to about 1.1% of the population comprises an oxidized methionine residue at position 82 of the antibody heavy chain or an oxidized methionine residue at position 85 of the antibody heavy chain, e) about 2.6% to about 3.3% of the population comprises an oxidized methionine at position 254 of the antibody heavy chain, f) about 0.5% to about 0.7% of the population comprises an oxidized methionine residue at position 430 of the antibody heavy chain, g) about 3.4% to about 6.5% of the population comprises a deamidated asparagine residue at amino acid residue 31 of the antibody light chain, and h) about 0.2% to about 0.8% of the population comprises an oxidized methionine residue at position 4 of the antibody light chain.

Another aspect of the disclosure is a composition comprising a population of anti-IL-5 antibodies having a) a modified form of the antibody heavy chain amino acid sequence shown in SEQ ID NO: 1 comprising at least one amino acid residue modification selected from the group consisting of a deamidated at asparagine residue at position 299, a deamidated asparagine residue at position 317 and a deamidated asparagine residue at position 386; and b) a modified form of the antibody light chain amino acid sequence shown in SEQ ID NO: 2 comprising a deamidated asparagine residue at amino acid residue 31.

In another embodiment the composition comprises: a) about 0.3% to about 1.5% of the population comprises a deamidated asparagine residue at position 317 of the antibody heavy chain, b) about 1.5% to about 4.5% of the population comprises a deamidated asparagine residue at position 386 of the antibody heavy chain; and c) about 3.3% to about 6.6% of the population comprises a deamidated asparagine residue at amino acid residue 31 of the antibody light chain.

In another embodiment the composition comprises: a) about 0.4% to about 1.2% of the population comprises a deamidated asparagine residue at position 317 of the antibody heavy chain, b) about 1.6% to about 4.2% of the population comprises a deamidated asparagine residue at position 386 of the antibody heavy chain; and c) about 3.4% to about 6.5% of the population comprises a deamidated asparagine residue at amino acid residue 31 of the antibody light chain.

Another aspect of the disclosure is a composition comprising a population of anti-IL-5 antibodies having a) a modified form of the antibody heavy chain amino acid sequence shown in SEQ ID NO: 1 comprising at least one amino acid residue modification selected from the group consisting of an oxidized tryptophan residue at position 52, an oxidized methionine residue at position 64, an oxidized methionine residue at position 82, an oxidized methionine residue at position 85, an oxidized cysteine residue at position 222, an oxidized methionine at position 254, an oxidized methionine at position 360 and an oxidized methionine residue at position 430; and b) a modified form of the antibody light chain amino acid sequence shown in SEQ ID NO: 2 comprising at least one amino acid residue modification selected from the group consisting of an oxidized methionine residue at position 4 and an oxidized cysteine residue at position 220.

In another embodiment the composition comprises: a) about 0.5% to about 1.5% of the population comprises an oxidized methionine residue at position 64 of the antibody heavy chain, b) about 0.2% to about 1.5% of the population comprises an oxidized methionine residue at position 82 of the antibody heavy chain or an oxidized methionine residue at position 85 of the antibody heavy chain, c) about 2.5% to about 3.5% of the population comprises an oxidized methionine at position 254 of the antibody heavy chain, d) about 0.4% to about 0.8% of the population comprises an oxidized methionine residue at position 430 of the antibody heavy chain, and e) about 0.1% to about 1% of the population comprises an oxidized methionine residue at position 4 of the antibody light chain.

In another embodiment the composition comprises: a) about 0.7% to about 0.9% of the population comprises an oxidized methionine residue at position 64 of the antibody heavy chain, b) about 0.3% to about 1.1% of the population comprises an oxidized methionine residue at position 82 of the antibody heavy chain or an oxidized methionine residue at position 85 of the antibody heavy chain, c) about 2.6% to about 3.3% of the population comprises an oxidized methionine at position 254 of the antibody heavy chain, d) about 0.5% to about 0.7% of the population comprises an oxidized methionine residue at position 430 of the antibody heavy chain, and e) about 0.2% to about 0.8% of the population comprises an oxidized methionine residue at position 4 of the antibody light chain.

Another aspect of the disclosure is a composition comprising a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2; and b) a main form of the antibody comprising greater than, or equal to, 20% of the protein in the composition as measured using capillary isoelectric focusing of the composition.

Another aspect of the disclosure is a composition comprising a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2; b) a main form of the antibody comprising greater than, or equal to, 20% of the protein in the composition as measured using capillary isoelectric focusing of the composition; and c) acidic forms of the antibody comprising up to about 80% of the protein in the composition as measured using capillary isoelectric focusing of the composition.

In another embodiment the composition is for the treatment of a disease selected from the group consisting of asthma, severe eosinophilic asthma, severe asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid and eosinophilic esophagitis.

Another embodiment is a method of treating a disease in a subject comprising the steps of a) identifying a subject with a disease selected from the group consisting of asthma, severe eosinophilic asthma, severe asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid and eosinophilic esophagitis; and b) administering a therapeutically effective amount of a composition according to the disclosure to the subject; whereby the disease in the subject is treated.

Another embodiment is a method of producing a composition of the disclosure, comprising the steps of: a) expressing in a host cell an antibody having a heavy chain amino acid sequence as shown in SEQ ID NO: 1 and a light chain amino acid sequence as shown in SEQ ID NO: 2, or an antibody variant having a heavy chain amino acid sequence at least 90% identical to the heavy chain amino acid sequence and/or a light chain amino acid sequence at least 90% identical to the light chain amino acid sequence; b) growing the cells at a pH of about 6.75 to about 7.00; c) harvesting a cell culture supernatant; d) placing the cell culture supernatant in contact with a protein A resin or protein G resin to bind antibody molecules; e) eluting the antibody molecules from the resin to produce an first eluate; f) treating the first eluate at a pH of about 3.3 to about 3.7 for about 15 to about 240 minutes to produce a treated first eluate; g) placing the treated first eluate in contact with a anion exchange resin at a load pH of about 8.3 to about 8.7; h) collecting a second eluate (a flow through eluate) from the anion exchange resin and holding this for about 96 hours or less; i) treating the second eluate with guanidine and ammonium sulphate to produce a solution; j) placing the solution in contact with a hydrophobic interaction chromatographic resin bed at a load ratio of about 12 g protein/L resin to about 27 g protein/L of resin load ratio; k) eluting a third eluate comprising the antibody molecules from the hydrophobic interaction chromatographic resin with an elution gradient volume of about 9 resin bed volumes to about 11 resin bed volumes and an elution peak cut stop of about 17% of the maximum peak height to about 23% of the maximum peak height; and 1) formulating the third eluate; whereby a composition of the disclosure is produced. In the methods of the disclosure any nucleic acid sequence suitable for expression of an antibody having a heavy chain amino acid sequence as shown in SEQ ID NO: 1 and a light chain amino acid sequence as shown in SEQ ID NO: 2, or an antibody variant having a heavy chain amino acid sequence at least 90% identical to the heavy chain amino acid sequence and/or a light chain amino acid sequence at least 90% identical to the light chain amino acid sequence. For example, the nucleic acid sequence of SEQ ID NO: 13 or SEQ ID NO: 14 may be used to express an antibody in a eukaryotic cell. Alternatively, other nucleic acid sequences with different sequences which encode (e.g., due to the use of alternative codons) the antibody heavy chain amino acid sequence as shown in SEQ ID NO: 1 or the antibody light chain amino acid sequence as shown in SEQ ID NO: 2 may be used. In the methods of the disclosure deamidation can be controlled by growing cells at a pH of about 6.75 to about 7.00. In the methods of the disclosure deamidation can be controlled by growing cells for about 12 to about 18 days for an in vitro cell age of less than or equal to 166 days. In the methods of the disclosure deamidation can be controlled by placing the treated first eluate in contact with an anion exchange resin at a load pH of about 8.3 to about 8.7 and collecting the second eluate from the anion exchange resin and holding this for about 96 hours or less. In the methods of the disclosure aggregation j can be controlled during phenyl SEPHAROSE™ fast flow chromatography by placing the solution in contact with the hydrophobic interaction chromatographic resin bed at a load ratio of about 12 g protein/L resin to about 27 g protein/L of resin load ratio; eluting a third eluate comprising the antibody molecules from the hydrophobic interaction chromatographic resin with an elution gradient volume of about 9 resin bed volumes to about 11 resin bed volumes and an elution peak cut stop of about 17% of the maximum peak height to about 23% of the maximum peak height. Aggregation can also be limited after final filtration, filling and freezing of the pharmaceutical compositions of the disclosure to less than or equal to about 6 hours. Importantly, any of the steps of the disclosed methods may be omitted, or combined to produce the compositions of the disclosure.

Upon production of the antibody, post-translational modifications may occur. This may include the cleavage of certain leader sequences, the addition of various sugar moieties in various glycosylation patterns, deamidation (for example at an asparagine or glutamine residue), oxidation (for example at a methionine, tryptophan or free cysteine residue), disulfide bond scrambling, isomerisation (for example at an aspartic acid residue), C-terminal lysine clipping (for example from one or both heavy chains), and N-terminal glutamine cyclisation (for example in the heavy and/or light chain).

The antibody composition may comprise (i) the antibody (i.e., an antibody having a heavy chain amino acid sequence as shown in SEQ ID NO: 1 and a light chain amino acid sequence as shown in SEQ ID NO: 2); and (ii) antibody variants that include one or more or a combination of: charge variants (e.g., acidic and basic variants), amino acid sequence variants, and antibody structural variants (e.g., aggregated and fragmented variants).

Acidic or basic antibody variants can be characterised and distinguished from the antibody based on their overall acidic or basic charge. For example, the charge distribution of the antibody composition can be detected using capillary isoelectric focusing (cIEF) or ion exchange chromatography. Acidic variants may comprise deamidated antibody variants, glycated antibody variants, sialylated antibody variants, and oxidised antibody variants. Cysteine and tryptophan oxidation in the antibody variant result in a pI shift (i.e., a charge difference) and are detected with other acidic antibody variants. Methionine oxidation in the antibody variant can be monitored by a change in antigen binding, or by peptide mapping, for example by LC-MS/MS.

Deamidation is an enzymatic reaction primarily converting asparagine (N) to iso-aspartic acid (iso-aspartate) (iso-D) and aspartic acid (aspartate) (D) at approximately 3:1 ratio. This deamidation reaction is therefore related to isomerization of aspartate (D) to iso-aspartate. The deamidation of asparagine and the isomerisation of aspartate, both involve the intermediate succinimide. To a much lesser degree, deamidation can occur with glutamine residues in a similar manner. Deamidation can occur in a CDR, in a Fab (non-CDR region), or in the Fc region.

Deamidation causes a change in the charge of the antibody, such that deamidated antibody variants are acidic compared to the antibody. The antibody composition may comprise ≤35% deamidated antibody variant. For example, N31 of the light chain may be deamidated to Iso-D, D or succinimide. The antibody composition may comprise ≤25% deamidated antibody variant at position 31 of the light chain. This can result in one amino acid change in the sequence of the light chain of the antibody, for example in ≤25% of the antibody composition.

For example, N386 of the heavy chain may be deamidated to Iso-D, D or succinimide. The antibody composition may comprise ≤35% deamidated antibody variant at position 386 of the heavy chain. This can result in one amino acid change in the sequence of the heavy chain of the antibody, for example in ≤35% of the antibody composition. The composition may comprise a mixture of antibody variants. Deamidation events can be cumulative, so that two or more asparagines residues are deamidated. Therefore, the antibody composition may comprise at least one amino acid change in the sequence of the heavy chain of the antibody and/or at least one amino acid change in the sequence of the heavy chain of the antibody. For example, the antibody composition may comprise deamidated antibody variant at position 31 of the light chain and deamidated antibody variant at position 386 of the heavy chain.

Oxidation can occur during production and storage (i.e., in the presence of oxidizing conditions) and results in a covalent modification of a protein, induced either directly by reactive oxygen species or indirectly by reaction with secondary by-products of oxidative stress. Oxidation happens primarily with methionine residues, but may occur at tryptophan and free cysteine residues. Oxidation can occur in a CDR, in a Fab (non-CDR) region, or in the Fc region.

Oxidation can cause a change in the charge of the antibody, such that oxidised antibody variants are acidic compared to the antibody. Some oxidised antibody variants have the same charge as the antibody. The antibody composition may comprise ≤55% oxidised antibody variant. For example, any one or a combination of M64, M254, and/or M430 of the heavy chain may be oxidised. The antibody composition may comprise ≤55% oxidised antibody variant at any one or a combination of M64, M254, and/or M430 of the heavy chain. For example, W52 of the heavy chain may be oxidised. The antibody composition may comprise ≤3% oxidised antibody variant at W52 of the heavy chain.

The composition may comprise a mixture of antibody variants. Therefore, the antibody composition may comprise at least one amino acid change in the sequence of the heavy chain of the antibody and/or at least one amino acid change in the sequence of the heavy chain of the antibody. For example, the antibody composition may comprise deamidated antibody variant at position 31 of the light chain; and/or deamidated antibody variant at position 386 of the heavy chain; and/or oxidation at any one or a combination of M64, M254, and/or M430 and/or W52 of the heavy chain.

Disulfide bond scrambling can occur during production and basic storage conditions. Under certain circumstances, disulfide bonds can break or form incorrectly, resulting in unpaired cysteine residues (—SH). These free (unpaired) sulfhydryls (—SH) can promote shuffling.

N-terminal glutamine (Q) and glutamate (glutamic acid) (E) in the heavy chain and/or light chain is likely to form pyroglutamate (pGlu) via cyclization. It is thought that most pGlu formation happens in the production bioreactor, but it can also be formed non-enzymatically, depending on pH and temperature of processing and storage conditions. Cyclization of N-terminal Q or E is commonly observed in natural human antibodies. The antibody composition described herein may comprise ≥50% pGlu at the N-terminus of the antibody. pGlu may be present in the heavy chain. This can result in one amino acid change in the sequence of the heavy or light chain of the antibody, for example in ≥50% of the antibody composition.

The composition may comprise a mixture of antibody variants. Sequence changes can be cumulative, so that the composition comprises two or more sequence changes in the heavy and/or light chain. Therefore, the antibody composition may comprise at least one amino acid change in the sequence of the heavy chain of the antibody and/or at least one amino acid change in the sequence of the heavy chain of the antibody. For example, the antibody composition may comprise deamidated antibody variant at position 31 of the light chain; and/or deamidated antibody variant at position 386 of the heavy chain; and/or oxidation at any one or a combination of M64, M254, and/or M430 and/or W52 of the heavy chain; and/or pGlu at the N-terminus of the heavy and/or light chain.

C-terminal lysine clipping is an enzymatic reaction catalyzed by carboxypeptidases, and is commonly observed in recombinant and natural human antibodies. Variants of this process include removal of lysine from one or both heavy chains due to cellular enzymes from the recombinant host cell. Upon administration to the human subject/patient is likely to result in the removal of any remaining C-terminal lysines. The antibody composition described herein may comprise ≥50% C-terminal lysine deleted at the C-terminus of the antibody. K449 may be deleted in one or both of the heavy chains of the antibody. Thus there are two antibody variants: lysine single deletion in the heavy chain, and lysine double deletion in the heavy chain. The antibody (i.e., an antibody having a heavy chain amino acid sequence as shown in SEQ ID NO: 1 and a light chain amino acid sequence as shown in SEQ ID NO: 2) has both lysines intact/present. This can result in one amino acid change in the sequence of the heavy chain of the antibody, for example in ≥50% of the antibody composition.

The composition may comprise a mixture of antibody variants. For example, the antibody composition may comprise deamidated antibody variant at position 31 of the light chain; and/or deamidated antibody variant at position 386 of the heavy chain; and/or oxidation at any one or a combination of M64, M254, and/or M430 and/or W52 of the heavy chain; and/or pGlu at the N-terminus of the heavy and/or light chain; and/or C-terminal lysine deleted at the C-terminus.

Aggregated or fragmented antibody variants can be characterised and distinguished from the antibody based on their size. For example, the size distribution of the antibody composition can be detected using size exclusion chromatography (SEC).

The antibody composition may comprise ≤20% aggregated antibody variant. The aggregated antibody variant may comprise dimer. The composition may comprise a mixture of antibody variants. For example, the antibody composition may comprise deamidated antibody variant at position 31 of the light chain; and/or deamidated antibody variant at position 386 of the heavy chain; and/or oxidation at any one or a combination of M64, M254, and/or M430 and/or W52 of the heavy chain; and/or pGlu at the N-terminus of the heavy and/or light chain; and/or C-terminal lysine deleted at the C-terminus; and/or aggregated antibody variant.

The compositions described may have been subjected to, or have undergone, one or more post-translational modifications. The modification may occur in a CDR, the variable framework region, or the constant region. The modification may result in a change in charge of the molecule. The post-translational modifications and changes in primary amino acid sequence described above, do not result in significant changes in antigen binding affinity, biological activity, PK/PD, aggregation, immunogenicity, or binding to the Fc receptor, of the compositions. The compositions are substantially free of contaminating materials.

The antibody composition comprising the antibody and antibody variants described above retain specific antigen binding and/or FcRn binding. For example, the antibody composition comprising the antibody and antibody variants described above has ≥0.70 IL-5 specific antigen binding; and/or ≥70% FcRn binding. Thus these levels (%) of variants can be tolerated in the antibody composition without impacting function.

The compositions described herein may be produced by any number of conventional techniques. For example, the compositions may be expressed in and purified from recombinant expression systems. In one embodiment, the composition is produced by a method of culturing a host cell under conditions suitable for expression of a polypeptide comprising SEQ ID NO: 1 and SEQ ID NO:2, wherein the composition is expressed, and optionally purified, and optionally formulated within a pharmaceutical composition.

A number of different expression systems and purification regimes can be used to produce the compositions. Generally, host cells are transformed with a recombinant expression vector encoding the antibody. A wide range of host cells can be employed, including Eukaryotic cell lines of mammalian origin (e.g., CHO, Perc6, HEK293, HeLa, NS0). Suitable host cells include mammalian cells such as CHO (e.g., CHOK1 and CHO-DG44).

The host cell may be an isolated host cell. The host cell is usually not part of a multicellular organism (e.g., plant or animal). The host cell may be a non-human host cell.

Appropriate cloning and expression vectors for use with eukaryotic or mammalian cellular hosts and methods of cloning are known in the art.

The cells may be cultured under conditions that promote expression of the antibody. For example, a production bioreactor is used to culture the cells. The production bioreactor volume may be: (i) about 20,000 litres, about 10,000 litres; about 5,000 litres; about 2,000 litres; about 1,000 litres; or about 500 litres; or (ii) between 500 and 20,000 litres; between 500 and 10,000 litres; between 500 and 5,000 litres; between 1,000 and 10,000 litres, or between 2,000 and 10,000 litres. For example, the cells may be cultured in a production bioreactor at a pH of about 6.75 to pH 7.00. Alternatively, the cells may be cultured in a production bioreactor for about 12 to about 18 days. Alternatively, the cells may be cultured in a production bioreactor at a pH of about 6.75 to pH 7.00, for about 12 to about 18 days. This culture step may help to control the level of deamidated antibody variants, for example, to reduce the level of deamidated antibody variants.

The composition may be recovered and purified by conventional protein purification procedures. For example, the composition may be harvested directly from the culture medium. Harvest of the cell culture medium may be via clarification, for example by centrifugation and/or depth filtration. Recovery of the composition is followed by purification to ensure adequate purity.

One or more chromatography steps may be used in purification, for example one or more chromatography resins; and/or one or more filtration steps. For example affinity chromatography using resins, such as protein A, G, or L may be used to purify the composition. Alternatively, or in addition to, an ion-exchange resin such as a cation-exchange may be used to purify the composition. Alternatively, or in addition to, a hydrophobic interaction chromatographic resin may be used to purify the composition. Alternatively the purification steps comprise: an affinity chromatography resin step, followed by a cation-exchange resin step, followed by a hydrophobic interaction chromatographic resin step.

For example, the harvest is placed in contact with a protein A resin. The solution comprising the composition may be eluted from the protein A resin and treated at pH 3.3 to 3.7 for 15 to 240 minutes. This protein A resin step may help to control the level of aggregated antibody variants, for example, to reduce the level of aggregated antibody variants.

The solution comprising the composition may then be further clarified by depth filtration and/or dual layer filtration.

Alternatively, or in addition to, an anion exchange resin may be used. The solution comprising the composition may be placed in contact with an anion exchange resin (for example Q-SEPHAROSE™ Fast Flow anion exchange chromatography) at a load pH of 8.3 to 8.7. The solution comprising the composition may be eluted from the anion exchange resin and held for 96 hours or less. This anion exchange resin step may help to control the level of deamidated antibody variants, for example, to reduce the level of deamidated antibody variants.

Optionally, guanidine and/or ammonium sulphate may be added to the solution comprising the composition, and held for 15 to 240 minutes.

Alternatively, or in addition to, a hydrophobic interaction chromatographic resin may be used. The solution comprising the composition may be placed in contact with a hydrophobic interaction chromatographic resin (e.g., phenyl SEPHAROSE™ fast flow chromatography) at a load ratio of 12 to 27 g protein/L resin. For example, the solution comprising the composition may be eluted using an elution gradient volume (bed volumes; BV) of about 9 to about 11. An elution peak cut stop (% of maximum peak height) of about 17 to about 23 may be used during elution from the hydrophobic interaction chromatographic resin. This hydrophobic interaction chromatographic resin step may help to control the level of aggregated antibody variants, for example, to reduce the level of aggregated antibody variants.

The solution comprising the composition may then be filtered to remove virus. The solution comprising the composition may then be formulated at an antibody concentration of about 76 g protein/L to about 82 g protein/L, or to about 100 g protein/L. The solution comprising the composition may be filled into containers and frozen. Aliquots of the solution comprising the composition may be lyophilized Lyophilizate may be reconstituted by the addition of water to produce a composition comprising 75 mg/L of protein, the monoclonal anti-IL-5 mepolizumab antibody and 20 mM sodium phosphate dibasic heptahydrate, 12% weight of sucrose to volume and 0.05% weight of polysorbate 80 to volume at a pH of from about 6.8 to about 7.2.

In another embodiment the composition of the disclosure is produced using this method of producing a composition of the disclosure.

Another aspect of the disclosure is a composition comprising a purified preparation of a monoclonal antibody and a buffering agent, wherein the composition is at a pH from 6.2 to 6.6, wherein the buffering agent is histidine, phosphate, citric acid, citric acid monohydrate, citrate or a salt thereof, wherein the purified preparation comprises the isoforms represented by peak 65, peak 78, peak 88, peak 92, the main peak and peak 112 shown in FIG. 1, wherein the antibody comprises a heavy chain an amino acid sequence having at least 90% identity to the amino acid sequence of SEQ ID NO: 1 and a light chain amino acid sequence having at least 90% identity to the amino acid sequence of SEQ ID NO: 2, and wherein the antibody is produced by a Chinese Hamster Ovary cell.

Another aspect of the disclosure is a composition comprising a purified preparation of a monoclonal antibody and a buffering agent, wherein the composition is at a pH from 6.2 to 6.6, wherein the buffering agent is phosphate or a salt thereof, wherein the purified preparation comprises the isoforms represented by peak 65, peak 78, peak 88, peak 92, the main peak and peak 112 shown in FIG. 1, wherein the antibody comprises a heavy chain amino acid sequence having at least 90% identity to the amino acid sequence of SEQ ID NO: 1 and a light chain amino acid sequence having at least 90% identity to the amino acid sequence of SEQ ID NO: 2, and wherein the antibody is produced by a Chinese Hamster Ovary cell.

In another embodiment of the compositions of the disclosure the buffering agent is at least one selected from the group consisting of sodium phosphate dibasic heptahydrate, phosphate and citric acid.

In another embodiment of the compositions of the disclosure comprise one selected from a first formulation of 16.1 mM sodium phosphate dibasic heptahydrate, 3.9 mM citric acid, 12% weight of sucrose to volume, 0.02% weight of polysorbate 80 to volume and 0.05 mM EDTA; a second formulation of 15.2 mM sodium phosphate dibasic heptahydrate, 4.8 mM citric acid, 12% weight of sucrose to volume, 0.02% weight of polysorbate 80 to volume and 0.05 mM EDTA; a third formulation of 15.8 mM sodium phosphate dibasic heptahydrate, 4.2 mM citric acid, 12% weight of sucrose to volume, 0.02% weight of polysorbate 80 to volume and 0.05 mM EDTA; a fourth formulation of 16.3 mM sodium phosphate dibasic heptahydrate, 3.7 mM citric acid, 12% weight of sucrose to volume, 0.02% weight of polysorbate 80 to volume and 0.05 mM EDTA; and a fifth formulation of 15.5 mM sodium phosphate dibasic heptahydrate, 4.5 mM citric acid, 12% weight of sucrose to volume, 0.02% weight of polysorbate 80 to volume and 0.05 mM EDTA.

In summary, the disclosure includes:

1. A composition comprising an antibody having a heavy chain amino acid sequence as shown in SEQ ID NO: 1 and a light chain amino acid sequence as shown in SEQ ID NO: 2, or an antibody variant having a heavy chain amino acid sequence at least 90% identical to the heavy chain amino acid sequence and/or a light chain amino acid sequence at least 90% identical to the light chain amino acid sequence, wherein the composition comprises: ≤80% acidic antibody variants.

2. The composition according to 1, wherein the composition has:
   a) ≥0.70 IL-5 specific antigen binding; and/or
   b) ≥70% FcRn binding.

3. The composition according to 2, wherein a) the specific antigen binding is in the range of from 0.70 to 1.30; and/or b) the FcRn binding is in the range of from 70% to 130%.

4. The composition according to any one of the preceding, wherein the composition comprises: ≤35% deamidated antibody variants.

5. The composition according to according to any one of the preceding, wherein the composition comprises: ≤25% deamidated antibody variants at N31 of the light chain amino acid sequence.

6. The composition according to according to any one of the preceding, wherein the composition comprises: ≤35% deamidated antibody variants at N386 of the heavy chain amino acid sequence.

7. The composition according to any one of the preceding, wherein the composition comprises: ≤55% oxidised antibody variant at any one or a combination of:
   a) M64 of the heavy chain amino acid sequence;
   b) M254 of the heavy chain amino acid sequence; and/or
   c) M430 of the heavy chain amino acid sequence.

8. The composition according to any one of the preceding, wherein the composition comprises: ≤3% oxidised antibody variants at W52 of the heavy chain amino acid sequence.

9. The composition according to any one of 4 to 8, wherein a deamidated antibody variant amount and/or an oxidised variant amount, is determined by peptide mapping LC-MS/MS.

10. The composition according to any one of the preceding, wherein the composition comprises: ≤20% aggregated antibody variants.

11. The composition according to 10, wherein the aggregated antibody variant comprises a dimer.

12. The composition according to 10 or 11 wherein the aggregated antibody variant amount is determined by SEC.

13. The composition according to any one of the preceding, wherein the composition comprises: ≥50% heavy chain amino acid sequence C-terminal lysine K449 deleted antibody variants.

14. The composition according to any one of the preceding, wherein the composition comprises: ≥50% heavy chain amino acid sequence pyro-glutamate N-terminal antibody variants.

15. A composition comprising an antibody having a heavy chain amino acid sequence as shown in SEQ ID NO: 1 and a light chain amino acid sequence as shown in SEQ ID NO: 2, or an antibody variant having a heavy chain amino acid sequence at least 90% identical to the heavy chain amino acid sequence and/or a light chain amino acid sequence at least 90% identical to the light chain amino acid sequence, wherein the composition comprises: ≤80% acidic antibody variants and ≤20% aggregated antibody variants.

16. A composition comprising an antibody having a heavy chain amino acid sequence as shown in SEQ ID NO: 1 and a light chain amino acid sequence as shown in SEQ ID NO: 2, or an antibody variant having a heavy chain amino acid sequence at least 90% identical to the heavy chain amino acid sequence and/or a light chain amino acid sequence at least 90% identical to the light chain amino acid sequence, wherein the composition comprises: ≤25% deamidated antibody variants at N31 of the light chain amino acid sequence; and ≤20% aggregated antibody variants.

17. A composition comprising an antibody having a heavy chain amino acid sequence as shown in SEQ ID NO: 1 and a light chain amino acid sequence as shown in SEQ ID NO: 2, or an antibody variant having a heavy chain amino acid sequence at least 90% identical to the heavy chain amino acid sequence and/or a light chain amino acid sequence at least 90% identical to the light chain amino acid sequence, wherein the composition comprises: ≤25% deamidated antibody variants at N31 of the light chain amino acid sequence; ≤55% oxidised antibody variants at M64 of the heavy chain amino acid sequence; ≤3% oxidised antibody variants at W52 of the heavy chain amino acid sequence; and ≤20% aggregated antibody variants.

18. A composition comprising an antibody having a heavy chain amino acid sequence as shown in SEQ ID NO: 1 and a light chain amino acid sequence as shown in SEQ ID NO: 2, or an antibody variant having a heavy chain amino acid sequence at least 90% identical to the heavy chain amino acid sequence and/or a light chain amino acid sequence at least 90% identical to the light chain amino acid sequence, wherein the composition comprises: ≤25% deamidated antibody variants at N31 of the light chain amino acid sequence; ≤35% deamidated antibody variants at N386 of the heavy chain amino acid sequence; and ≤20% aggregated antibody variants.

19. A composition comprising an antibody having a heavy chain amino acid sequence as shown in SEQ ID NO: 1 and a light chain amino acid sequence as shown in SEQ ID NO: 2, or an antibody variant having a heavy chain amino acid sequence at least 90% identical to the heavy chain amino acid sequence and/or a light chain amino acid sequence at least 90% identical to the light chain amino acid sequence, wherein the composition comprises: ≤25% deamidated antibody variants at N31 of the light chain amino acid sequence; ≤35% deamidated antibody variants at N386 of the heavy chain amino acid sequence; ≤55% oxidised antibody variants at M64 of the heavy chain amino acid sequence, M254 of the heavy chain amino acid sequence, M430 of the heavy chain amino acid sequence; ≤3% oxidised antibody variants at W52 of the heavy chain amino acid sequence; and ≤20% aggregated antibody variants.

20. A composition comprising a purified preparation of a monoclonal antibody and a buffering agent,
wherein the composition is at a pH from 6.8 to 7.2,
wherein the buffering agent is histidine, phosphate, citric acid, citrate or a salt thereof,
wherein the purified preparation comprises the isoforms represented by peak 65, peak 78, peak 88, peak 92, the main peak and peak 112 shown in FIG. 1,
wherein the antibody comprises a heavy chain an amino acid sequence having at least 90% identity to the amino acid sequence of SEQ ID NO: 1 and a light chain amino acid sequence having at least 90% identity to the amino acid sequence of SEQ ID NO: 2, and
wherein the antibody is produced by a Chinese Hamster Ovary cell.

21. The composition of 20, wherein the buffering agent is at least one selected from the group consisting of sodium phosphate dibasic heptahydrate, phosphate, citric acid and citrate.

22. The composition of 20, wherein the buffering agent is sodium phosphate, potassium phosphate, or sodium citrate.

23. The composition of 20, wherein the composition further comprises a sugar, a carbohydrate and/or a salt.

24. The composition of 23, wherein the composition comprises sucrose.

25. A composition comprising a purified preparation of a monoclonal antibody and a buffering agent,
wherein the composition is at a pH from 6.8 to 7.2,
wherein the buffering agent is phosphate or a salt thereof,
wherein the purified preparation comprises the isoforms represented by peak 65, peak 78, peak 88, peak 92, the main peak and peak 112 shown in FIG. 1,
wherein the antibody comprises a heavy chain amino acid sequence having at least 90% identity to the amino acid sequence of SEQ ID NO: 1 and a light chain amino acid sequence having at least 90% identity to the amino acid sequence of SEQ ID NO: 2, and
wherein the antibody is produced by a Chinese Hamster Ovary cell.

26. The composition of 25, wherein the buffering agent is at least one selected from the group consisting of sodium phosphate dibasic heptahydrate, phosphate, citric acid and citrate.

27. The composition of 26, wherein the composition further comprises a sugar.

28. The composition of 27, wherein the sugar is sucrose.

29. The composition of 28, comprising polysorbate 80.

30. The composition of 29, comprising one selected from a first formulation of 20 mM sodium phosphate dibasic heptahydrate, 12% weight of sucrose to volume and 0.05% weight of polysorbate 80 to volume; a second formulation of 15.5 mM sodium phosphate dibasic heptahydrate, 3.9 mM citric acid monohydrate, 12% weight of sucrose to volume, 0.02% weight of polysorbate 80 to volume and 0.05 mM EDTA; and a third formulation of 26 mM sodium phosphate dibasic heptahydrate, 15% weight of sucrose to volume and 0.065% weight of polysorbate 80 to volume.

31. The composition of 29, wherein the antibody has a dissociation constant equal to, or less than, about $3.5 \times 10^{-11}$ M for human interleukin-5 comprising the amino acid sequence shown in SEQ ID NO: 11.

32. The composition of 31, wherein the monoclonal antibody concentration is about 75 mg/mL or about 100 mg/mL.
33. The composition of 30, wherein the antibody has a dissociation constant equal to, or less than, about $3.5\times10^{-11}$ M for human interleukin-5 comprising the amino acid sequence shown in SEQ ID NO: 11.
34. The composition of 33, wherein the monoclonal antibody concentration is about 75 mg/mL or about 100 mg/mL.
35. A composition comprising
  a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2; and
  b) a main form of the antibody comprising greater than, or equal to, 50% of the protein in the composition as measured using capillary isoelectric focusing of the composition.
36. The composition of 35 wherein the main form of the antibody comprises at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220.
37. A composition comprising
  a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2;
  b) a main form of the antibody comprising greater than, or equal to, 50% of the protein in the composition as measured using capillary isoelectric focusing of the composition; and
  c) acidic forms of the antibody comprising about 20% to about 45% of the protein in the composition as measured using capillary isoelectric focusing of the composition.
38. The composition of 37 wherein the acidic forms of the antibody comprise at least one selected from the group consisting of a peak 65 acidic form, a peak 78 acidic form, a peak 88 acidic form and a peak 92 acidic form.
39. The composition of 38 wherein the acidic forms of the antibody comprise at least one deamidated amino acid residue selected from the group consisting of a heavy chain amino acid residue deamidated at asparagine 299, a heavy chain amino acid residue deamidated at asparagine 317, a heavy chain amino acid residue deamidated at asparagine 386 and a light chain amino acid residue deamidated at asparagine 31.
40. The composition of 39 wherein the main form of the antibody comprises at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220.
41. The composition of 39 wherein the acidic forms of the antibody comprise at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220.
42. The composition of 39 wherein the main form of the antibody comprises at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220; and wherein the acidic forms of the antibody comprise at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220.
43. A composition comprising
  a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2;
  b) a main form of the antibody comprising greater than, or equal to, 50% of the protein in the composition as measured using capillary isoelectric focusing of the composition; and
  c) a basic form of the antibody comprising about 1% to about 15% of the protein in the composition as measured using capillary isoelectric focusing of the composition.
44. The composition of 43 wherein the basic form of the antibody comprises a peak 112 basic form.
45. The composition of 44 wherein the basic form of the antibody comprises a heavy chain having a carboxy terminal residue that is glycine 448.
46. The composition of 45 wherein the main form of the antibody comprises at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220.

47. The composition of 45 wherein the basic forms of the antibody comprise at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a heavy chain amino acid residue oxidized at cysteine 220.

48. The composition of 45 wherein the main form of the antibody comprises at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a heavy chain amino acid residue oxidized at cysteine 220; and
wherein the basic forms of the antibody comprise at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220.

49. A composition comprising
  a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2;
  b) a main form of the antibody comprising greater than, or equal to, 50% of the protein in the composition as measured using capillary isoelectric focusing of the composition;
  c) acidic forms of the antibody comprising about 20% to about 45% of the protein in the composition as measured using capillary isoelectric focusing of the composition; and
  d) a basic form of the antibody comprising about 1% to about 15% of the protein in the composition as measured using capillary isoelectric focusing of the composition.

50. The composition of 49 wherein the acidic forms of the antibody comprise at least one selected from the group consisting of a peak 65 acidic form, a peak 78 acidic form, a peak 88 acidic form and a peak 92 acidic form.

51. The composition of 50 wherein the acidic forms of the antibody comprise at least one deamidated amino acid residue selected from the group consisting of a heavy chain amino acid residue deamidated at asparagine 299, a heavy chain amino acid residue deamidated at asparagine 317, a heavy chain amino acid residue deamidated at asparagine 386 and a light chain amino acid residue deamidated at asparagine 31.

52. The composition of 49 wherein the basic form of the antibody comprises a peak 112 basic form.

53. The composition of 52 wherein the basic form of the antibody comprises a heavy chain having a carboxy terminal residue that is glycine 448.

54. The composition of 49 wherein the main form of the antibody comprises at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220.

55. The composition of 49 wherein the acidic forms of the antibody comprise at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a heavy chain amino acid residue oxidized at cysteine 220.

56. The composition of 49 wherein the basic forms of the antibody comprise at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220.

57. The composition of 49 wherein the main form of the antibody comprises at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a heavy chain amino acid residue oxidized at cysteine 222;

and wherein the acidic forms of the antibody comprise at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220.

58. The composition of 49 wherein the acidic forms of the antibody comprise at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220; and wherein the basic forms of the antibody comprise at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220.

59. The composition of 49 wherein the main form of the antibody comprise at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220; and wherein the basic forms of the antibody comprise at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220.

60. The composition of 49 wherein the main form of the antibody comprises at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220;
wherein the acidic forms of the antibody comprise at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 220, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220; and
wherein the basic forms of the antibody comprise at least one oxidized amino acid residue selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220.

61. A composition comprising
  a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2; and
  b) deamidated forms of the antibody comprising at least one selected from the group consisting of a heavy chain amino acid residue deamidated at asparagine 299, a heavy chain amino acid residue deamidated at asparagine 317, a heavy chain amino acid residue deamidated at asparagine 386 and a light chain amino acid residue deamidated at asparagine 31.

62. A composition comprising
  a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2; and
  b) oxidized forms of the antibody comprising at least one selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220.

63. A composition comprising
   a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2;
   b) deamidated forms of the antibody comprising at least one selected from the group consisting of a heavy chain amino acid residue deamidated at asparagine 299, a heavy chain amino acid residue deamidated at asparagine 317, a heavy chain amino acid residue deamidated at asparagine 386 and a light chain amino acid residue deamidated at asparagine 31; and
   c) oxidized forms of the antibody comprising at least one selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85, a heavy chain amino acid residue oxidized at cysteine 222, a heavy chain amino acid residue oxidized at methionine 254, a heavy chain amino acid residue oxidized at methionine 360, a heavy chain amino acid residue oxidized at methionine 430, a light chain amino acid residue oxidized at methionine 4 and a light chain amino acid residue oxidized at cysteine 220.

64. A composition comprising
   a) an anti-IL-5 antibody comprising a heavy chain variable region having the CDRH1 amino acid sequence shown in SEQ ID NO: 5, the CDRH2 amino acid sequence shown in SEQ ID NO: 6, and the CDRH3 amino acid sequence shown in SEQ ID NO: 7; and a light chain variable region having the CDRL1 amino acid sequence shown in SEQ ID NO: 8, the CDRL2 amino acid sequence shown in SEQ ID NO: 9, and the CDRL3 amino acid sequence shown in SEQ ID NO: 10; and
   b) deamidated forms of the antibody comprising a light chain amino acid residue deamidated at asparagine 31.

65. A composition comprising
   a) an anti-IL-5 antibody comprising a heavy chain variable region having the CDRH1 amino acid sequence shown in SEQ ID NO: 5, the CDRH2 amino acid sequence shown in SEQ ID NO: 6, and the CDRH3 amino acid sequence shown in SEQ ID NO: 7; and a light chain variable region having the CDRL1 amino acid sequence shown in SEQ ID NO: 8, the CDRL2 amino acid sequence shown in SEQ ID NO: 9, and the CDRL3 amino acid sequence shown in SEQ ID NO: 10; and
   b) oxidized forms of the antibody comprising at least one selected from the group consisting of a heavy chain amino acid residue oxidized at tryptophan 52 and a heavy chain amino acid residue oxidized at methionine 64.

66. A composition comprising
   a) an anti-IL-5 antibody comprising a heavy chain variable region having the CDRH1 amino acid sequence shown in SEQ ID NO: 5, the CDRH2 amino acid sequence shown in SEQ ID NO: 6, and the CDRH3 amino acid sequence shown in SEQ ID NO: 7; and a light chain variable region having the CDRL1 amino acid sequence shown in SEQ ID NO: 8, the CDRL2 amino acid sequence shown in SEQ ID NO: 9, and the CDRL3 amino acid sequence shown in SEQ ID NO: 10;
   b) oxidized forms of the antibody comprising at least one selected from the group consisting of a heavy chain amino acid residue oxidized at tryptophan 52 and a heavy chain amino acid residue oxidized at methionine 64; and
   c) deamidated forms of the antibody comprising a light chain amino acid residue deamidated at asparagine 31.

67. A composition comprising
   a) an anti-IL-5 antibody comprising a heavy chain variable region sequence having the amino acid sequence shown in SEQ ID NO: 3 and a light chain variable region sequence having the amino acid sequence shown in SEQ ID NO: 4; and
   b) deamidated forms of the antibody comprising a light chain amino acid residue deamidated at asparagine 31.

68. A composition comprising
   a) an anti-IL-5 antibody comprising a heavy chain variable region sequence having the amino acid sequence shown in SEQ ID NO: 3 and a light chain variable region sequence having the amino acid sequence shown in SEQ ID NO: 4; and
   b) oxidized forms of the antibody comprising at least one selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85 and a light chain amino acid residue oxidized at methionine 4.

69. A composition comprising
   a) an anti-IL-5 antibody comprising a heavy chain variable region sequence having the amino acid sequence shown in SEQ ID NO: 3 and a light chain variable region sequence having the amino acid sequence shown in SEQ ID NO: 4;
   b) deamidated forms of the antibody comprising a light chain amino acid residue deamidated at asparagine 31; and
   c) oxidized forms of the antibody comprising at least one selected from the group consisting of a heavy chain amino acid residue oxidized at tryptophan 52, a heavy chain amino acid residue oxidized at methionine 64, a heavy chain amino acid residue oxidized at methionine 82, a heavy chain amino acid residue oxidized at methionine 85 and a light chain amino acid residue oxidized at methionine 4.

70. A composition comprising a population of anti-IL-5 antibodies having
   a) a modified form of the antibody heavy chain amino acid sequence shown in SEQ ID NO: 1 comprising at least one amino acid residue modification selected from the group consisting of an amino terminal pyroglutamate residue at amino acid residue 1, a carboxy terminal glycine amino acid residue at amino acid residue 448, a deamidated asparagine residue at position 299, a deamidated asparagine residue at position 317, a deamidated asparagine residue at position 386, an oxidized tryptophan residue at position 52, an oxidized methionine residue at position 64, an oxidized methionine residue at position 82, an oxidized methionine residue at position 85, an oxidized cysteine at position 222, an oxidized methionine at position 254, an oxidized methionine at position 360 and an oxidized methionine residue at position 430; and b) a modified form of the antibody light chain amino acid sequence shown in SEQ ID NO: 2 comprising at least one amino acid residue modification selected from the group consisting of a deamidated asparagine residue at amino acid residue 31, an oxidized methionine residue at position 4 and an oxidized cysteine at position 220.

71. The composition of 70 wherein:
   a) about greater than or equal to 92% of the population comprises an amino terminal pyroglutamate residue at amino acid residue 1 of the antibody heavy chain,
   b) about greater than or equal to 90% of the population comprises a carboxy terminal glycine amino acid residue at amino acid residue 448 of the antibody heavy chain,
   c) less than or equal to 6.0% of the population comprises a deamidated asparagine residue at position 386 of the antibody heavy chain;
   d) about less than or equal to 1.5% of the population comprises an oxidized methionine residue at position 64 of the antibody heavy chain,
   e) about less than or equal to 4.5% of the population comprises an oxidized methionine at position 254 of the antibody heavy chain,
   f) about less than or equal to 0.8% of the population comprises an oxidized methionine residue at position 430 of the antibody heavy chain, and
   g) about less than or equal to 6.6% of the population comprises a deamidated asparagine residue at amino acid residue 31 of the antibody light chain.

72. The composition of 71 wherein:
   a) about 93.7% to about 98.6% of the population comprises an amino terminal pyroglutamate residue at amino acid residue 1 of the antibody heavy chain,
   b) about 97.6% to about 99.2% of the population comprises a carboxy terminal glycine amino acid residue at amino acid residue 448 of the antibody heavy chain,
   c) about 0.4% to about 1.2% of the population comprises a deamidated asparagine residue at position 317 of the antibody heavy chain,
   d) about 1.6% to about 4.2% of the population comprises a deamidated asparagine residue at position 386 of the antibody heavy chain;
   e) about 0.7% to about 0.9% of the population comprises an oxidized methionine residue at position 64 of the antibody heavy chain,
   f) about 0.3% to about 1.1% of the population comprises an oxidized methionine residue at position 82 of the antibody heavy chain or an oxidized methionine residue at position 85 of the antibody heavy chain,
   g) about 2.6% to about 3.3% of the population comprises an oxidized methionine at position 254 of the antibody heavy chain,
   h) about 0.5% to about 0.7% of the population comprises an oxidized methionine residue at position 430 of the antibody heavy chain,
   i) about 3.4% to about 6.5% of the population comprises a deamidated asparagine residue at amino acid residue 31 of the antibody light chain, and
   j) about 0.2% to about 0.8% of the population comprises an oxidized methionine residue at position 4 of the antibody light chain.

73. A composition comprising a population of anti-IL-5 antibodies having
   a) a modified form of the antibody heavy chain amino acid sequence shown in SEQ ID NO: 1 comprising at least one amino acid residue modification selected from the group consisting of a deamidated asparagine residue at position 299, a deamidated asparagine residue at position 317, a deamidated asparagine residue at position 386, an oxidized tryptophan residue at position 52, an oxidized methionine residue at position 64, an oxidized methionine residue at position 82, an oxidized methionine residue at position 85, an oxidized cysteine at position 222, an oxidized methionine at position 254, an oxidized methionine at position 254, an oxidized methionine at position 360 and an oxidized methionine residue at position 430; and
   b) a modified form of the antibody light chain amino acid sequence shown in SEQ ID NO: 2 comprising at least one amino acid residue modification selected from the group consisting of a deamidated asparagine residue at amino acid residue 31, an oxidized methionine residue at position 4 and an oxidized cysteine at position 220.

74. The composition of 73 wherein:
   a) about 0.3% to about 1.5% of the population comprises a deamidated asparagine residue at position 317 of the antibody heavy chain,
   b) about 1.5% to about 4.5% of the population comprises a deamidated asparagine residue at position 386 of the antibody heavy chain;
   c) about 0.5% to about 1.5% of the population comprises an oxidized methionine residue at position 64 of the antibody heavy chain,
   d) about 0.2% to about 1.5% of the population comprises an oxidized methionine residue at position 82 of the antibody heavy chain or an oxidized methionine residue at position 85 of the antibody heavy chain,
   e) about 2.5% to about 3.5% of the population comprises an oxidized methionine at position 254 of the antibody heavy chain,
   f) about 0.4% to about 0.8% of the population comprises an oxidized methionine residue at position 430 of the antibody heavy chain,
   g) about 3.3% to about 6.6% of the population comprises a deamidated asparagine residue at amino acid residue 31 of the antibody light chain, and
   h) about 0.1% to about 1% of the population comprises an oxidized methionine residue at position 4 of the antibody light chain.

75. The composition of 74 wherein:
   a) about 0.4% to about 1.2% of the population comprises a deamidated asparagine residue at position 317 of the antibody heavy chain,
   b) about 1.6% to about 4.2% of the population comprises a deamidated asparagine residue at position 386 of the antibody heavy chain;
   c) about 0.7% to about 0.9% of the population comprises an oxidized methionine residue at position 64 of the antibody heavy chain,
   d) about 0.3% to about 1.1% of the population comprises an oxidized methionine residue at position 82 of the antibody heavy chain or an oxidized methionine residue at position 85 of the antibody heavy chain,
   e) about 2.6% to about 3.3% of the population comprises an oxidized methionine at position 254 of the antibody heavy chain,
   f) about 0.5% to about 0.7% of the population comprises an oxidized methionine residue at position 430 of the antibody heavy chain,
   g) about 3.4% to about 6.5% of the population comprises a deamidated asparagine residue at amino acid residue 31 of the antibody light chain, and h) about 0.2% to about 0.8% of the population comprises an oxidized methionine residue at position 4 of the antibody light chain.

76. A composition comprising a population of anti-IL-5 antibodies having
   a) a modified form of the antibody heavy chain amino acid sequence shown in SEQ ID NO: 1 comprising at least one amino acid residue modification selected from the group consisting of a deamidated asparagine residue at position 299, a deamidated asparagine residue at position 317 and a deamidated asparagine residue at position 386; and
   b) a modified form of the antibody light chain amino acid sequence shown in SEQ ID NO: 2 comprising a deamidated asparagine residue at amino acid residue 31.

77. The composition of 76 wherein:
   a) about 0.3% to about 1.5% of the population comprises a deamidated asparagine residue at position 317 of the antibody heavy chain,
   b) about 1.5% to about 4.5% of the population comprises a deamidated asparagine residue at position 386 of the antibody heavy chain; and
   c) about 3.3% to about 6.6% of the population comprises a deamidated asparagine residue at amino acid residue 31 of the antibody light chain.

78. The composition of 77 wherein:
   a) about 0.4% to about 1.2% of the population comprises a deamidated asparagine residue at position 317 of the antibody heavy chain,
   b) about 1.6% to about 4.2% of the population comprises a deamidated asparagine residue at position 386 of the antibody heavy chain; and
   c) about 3.4% to about 6.5% of the population comprises a deamidated asparagine residue at amino acid residue 31 of the antibody light chain.

79. A composition comprising a population of anti-IL-5 antibodies having
   a) a modified form of the antibody heavy chain amino acid sequence shown in SEQ ID NO: 1 comprising at least one amino acid residue modification selected from the group consisting of an oxidized tryptophan residue at position 52, an oxidized methionine residue at position 64, an oxidized methionine residue at position 82, an oxidized methionine residue at position 85, an oxidized cysteine at position 222, an oxidized methionine at position 254, an oxidized methionine at position 360 and an oxidized methionine residue at position 430; and
   b) a modified form of the antibody light chain amino acid sequence shown in SEQ ID NO: 2 comprising at least one amino acid residue modification selected from the group consisting of an oxidized methionine residue at position 4 and an oxidized cysteine at position 220.

80. The composition of 79 wherein:
   c) about 0.5% to about 1.5% of the population comprises an oxidized methionine residue at position 64 of the antibody heavy chain,
   d) about 0.2% to about 1.5% of the population comprises an oxidized methionine residue at position 82 of the antibody heavy chain or an oxidized methionine residue at position 85 of the antibody heavy chain,
   e) about 2.5% to about 3.5% of the population comprises an oxidized methionine at position 254 of the antibody heavy chain,
   f) about 0.4% to about 0.8% of the population comprises an oxidized methionine residue at position 430 of the antibody heavy chain, and
   g) about 0.1% to about 1% of the population comprises an oxidized methionine residue at position 4 of the antibody light chain.

81. The composition of 80 wherein:
   a) about 0.7% to about 0.9% of the population comprises an oxidized methionine residue at position 64 of the antibody heavy chain,
   b) about 0.3% to about 1.1% of the population comprises an oxidized methionine residue at position 82 of the antibody heavy chain or an oxidized methionine residue at position 85 of the antibody heavy chain,
   c) about 2.6% to about 3.3% of the population comprises an oxidized methionine at position 254 of the antibody heavy chain,
   d) about 0.5% to about 0.7% of the population comprises an oxidized methionine residue at position 430 of the antibody heavy chain, and
   e) about 0.2% to about 0.8% of the population comprises an oxidized methionine residue at position 4 of the antibody light chain.

82. A composition comprising
   a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2; and
   b) a main form of the antibody comprising greater than, or equal to, 20% of the protein in the composition as measured using capillary isoelectric focusing of the composition.

83. A composition comprising
   a) an anti-IL-5 antibody comprising a heavy chain sequence having at least 90% identity to the amino acid sequence shown in SEQ ID NO: 1 and a light chain sequence having at least 90% identity to the amino acid sequence shown in SEQ ID NO: 2;
   b) a main form of the antibody comprising greater than, or equal to, 20% of the protein in the composition as measured using capillary isoelectric focusing of the composition; and
   c) acidic forms of the antibody comprising up to about 80% of the protein in the composition as measured using capillary isoelectric focusing of the composition.

84. A composition according to any of the preceding for the treatment of a disease selected from the group consisting of asthma, severe eosinophilic asthma, severe asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid and eosinophilic esophagitis.

85. A method of treating a disease in a subject comprising the steps of
   a) identifying a subject with a disease selected from the group consisting of asthma, severe eosinophilic asthma, severe asthma, uncontrolled eosinophilic asthma, eosinophilic asthma, sub-eosinophilic asthma, chronic obstructive pulmonary disease, eosinophilic granulomatosis with polyangiitis, hypereosinophilic syndrome, nasal polyposis, bullous pemphigoid and eosinophilic esophagitis; and
   b) administering a therapeutically effective amount of a composition according to any of the preceding to the subject;
   whereby the disease in the subject is treated.

86. The composition of 20 to 83, wherein the composition has:
   a) ≥0.70 IL-5 specific antigen binding; and/or
   b) ≥70% FcRn binding.
87. The composition of 20 to 83, wherein a) the specific antigen binding is in the range of from 0.70 to 1.30; and/or b) the FcRn binding is in the range of from 70% to 130%.
88. The composition of 20 to 83, wherein the composition comprises: ≤20% aggregated antibody variants.
89. The composition of 20 to 83, wherein the aggregated antibody variant comprises a dimer.
90. A method of producing a composition of 1-83, comprising the steps of:
   a) expressing in a host cell an antibody having a heavy chain amino acid sequence as shown in SEQ ID NO: 1 and a light chain amino acid sequence as shown in SEQ ID NO: 2, or an antibody variant having a heavy chain amino acid sequence at least 90% identical to the heavy chain amino acid sequence and/or a light chain amino acid sequence at least 90% identical to the light chain amino acid sequence;
   b) growing the cells at a pH of about 6.75 to about 7.00 for about 12 to about 18 days for an in vitro cell age of less than or equal to 166 days;
   c) harvesting a cell culture supernatant;
   d) placing the cell culture supernatant in contact with a protein A resin or protein G resin to bind antibody molecules;
   e) eluting the antibody molecules from the resin to produce an first eluate;
   f) treating the first eluate at a pH of about 3.3 to about 3.7 for about 15 to about 240 minutes to produce a treated first eluate;
   g) placing the treated first eluate in contact with a anion exchange resin at a load pH of about 8.3 to about 8.7;
   h) collecting a second eluate from the anion exchange resin and holding this for about 96 hours or less;
   i) treating the second eluate with guanidine and ammonium sulphate to produce a solution;
   j) placing the solution in contact with a hydrophobic interaction chromatographic resin bed at a load ratio of about 12 g protein/L resin to about 27 g protein/L of resin load ratio;
   k) eluting a third eluate comprising the antibody molecules from the hydrophobic interaction chromatographic resin with an elution gradient volume of about 9 resin bed volumes to about 11 resin bed volumes and an elution peak cut stop of about 17% of the maximum peak height to about 23% of the maximum peak height; and
   l) formulating the third eluate;
   whereby the composition of 1-83 is produced.
91. The composition of 1-83 produced by the method of 90.
92. A composition comprising a purified preparation of a monoclonal antibody and a buffering agent,
   wherein the composition is at a pH from 6.2 to 6.6,
   wherein the buffering agent is histidine, phosphate, citric acid, citric acid monohydrate, citrate or a salt thereof,
   wherein the purified preparation comprises the isoforms represented by peak 65, peak 78, peak 88, peak 92, the main peak and peak 112 shown in FIG. 1,
   wherein the antibody comprises a heavy chain an amino acid sequence having at least 90% identity to the amino acid sequence of SEQ ID NO: 1 and a light chain amino acid sequence having at least 90% identity to the amino acid sequence of SEQ ID NO: 2, and
   wherein the antibody is produced by a Chinese Hamster Ovary cell.
93. The composition of 92, wherein the buffering agent is at least one selected from the group consisting of sodium phosphate dibasic heptahydrate, phosphate, citric acid and citric acid monohydrate.
94. The composition of 92, wherein the buffering agent is sodium phosphate, potassium phosphate, citric acid, citric acid monohydrate or sodium citrate.
95. The composition of 92, wherein the composition further comprises a sugar, a carbohydrate and/or a salt.
96. The composition of 95, wherein the composition comprises sucrose.
97. A composition comprising a purified preparation of a monoclonal antibody and a buffering agent,
   wherein the composition is at a pH from 6.2 to 6.6,
   wherein the buffering agent is phosphate or a salt thereof,
   wherein the purified preparation comprises the isoforms represented by peak 65, peak 78, peak 88, peak 92, the main peak and peak 112 shown in FIG. 1,
   wherein the antibody comprises a heavy chain amino acid sequence having at least 90% identity to the amino acid sequence of SEQ ID NO: 1 and a light chain amino acid sequence having at least 90% identity to the amino acid sequence of SEQ ID NO: 2, and
   wherein the antibody is produced by a Chinese Hamster Ovary cell.
98. The composition of 97, wherein the buffering agent is at least one selected from the group consisting of sodium phosphate dibasic heptahydrate, phosphate, citric acid, citric acid monohydrate and citrate.
99. The composition of 98, wherein the composition further comprises a sugar.
100. The composition of 99, wherein the sugar is sucrose.
101. The composition of 100, comprising polysorbate 80.
102. The composition of 101, comprising one selected from a first formulation of 16.1 mM sodium phosphate dibasic heptahydrate, 3.9 mM citric acid monohydrate, 12% weight of sucrose to volume, 0.02% weight of polysorbate 80 to volume and 0.05 mM EDTA; a second formulation of 15.2 mM sodium phosphate dibasic heptahydrate, 4.8 mM citric acid monohydrate, 12% weight of sucrose to volume, 0.02% weight of polysorbate 80 to volume and 0.05 mM EDTA; a third formulation of 15.8 mM sodium phosphate dibasic heptahydrate, 4.2 mM citric acid monohydrate, 12% weight of sucrose to volume, 0.02% weight of polysorbate 80 to volume and 0.05 mM EDTA; a fourth formulation of 16.3 mM sodium phosphate dibasic heptahydrate, 3.7 mM citric acid monohydrate, 12% weight of sucrose to volume, 0.02% weight of polysorbate 80 to volume and 0.05 mM EDTA; and a fifth formulation of 15.5 mM sodium phosphate dibasic heptahydrate, 4.5 mM citric acid monohydrate, 12% weight of sucrose to volume, 0.02% weight of polysorbate 80 to volume and 0.05 mM EDTA.
103. The composition of 101, wherein the antibody has a dissociation constant equal to, or less than, about $3.5 \times 10^{-11}$ M for human interleukin-5 comprising the amino acid sequence shown in SEQ ID NO: 11.
104. The composition of 101, wherein the monoclonal antibody concentration is about 75 mg/mL or about 100 mg/mL.
105. The composition of 102, wherein the antibody has a dissociation constant equal to, or less than, about $3.5 \times 10^{-11}$ M for human interleukin-5 comprising the amino acid sequence shown in SEQ ID NO: 11.
106. A composition according to any one of the preceding wherein the antibody is at a concentration of between about 75 mg/ml to about 100 mg/ml.

107. A composition according to any one of the preceding wherein the composition further comprises one or a combination of:
   a) a buffering agent selected from the group consisting of sodium phosphate dibasic heptahydrate, phosphate, citrate, sodium phosphate, potassium phosphate, sodium citrate, and histidine, providing a pH of between 6.8 and 7.2; and/or
   b) a sugar; and/or
   c) polysorbate 80; and/or d) EDTA.

108. A composition according to any one of the preceding claims wherein the composition further comprises one or a combination of:
   a) a buffering agent selected from the group consisting of sodium phosphate dibasic heptahydrate, phosphate, citrate, citric acid monohydrate, sodium phosphate, potassium phosphate, sodium citrate, and histidine, providing a pH of between 6.2 and 6.6; and/or
   b) a sugar; and/or
   c) polysorbate 80; and/or d) EDTA.

EXAMPLES

Example 1

Preparation of a Composition

Multiple batches of a composition comprising the monoclonal anti-IL-5 antibody mepolizumab were produced.

An inoculum of Chinese Hamster Ovary cells stably transfected with expression vector constructs comprising the nucleic acid sequences shown SEQ ID NO: 13 and SEQ ID NO: 14 was cultured in 5000 L bioreactors containing a liquid cell culture medium. The mature antibody encoded by these nucleic acids is mepolizumab and comprises the heavy chain amino acid sequence shown in SEQ ID NO: 1 and the light chain amino acid sequence shown in SEQ ID NO: 2.

Bioreactors were operated at a temperature of about 34.5° C. to about 35.5° C. Air and oxygen were sparged into the culture medium and a pH of about 6.75 to 7.00 was maintained. The culture duration was about 12 to 18 days. The in vitro cell age (culture days from initial thaw of master cell bank to harvest) was 166 days or less. After this, a clarified cell culture supernatant was harvested by centrifugation and depth filtration of the cell culture medium. This clarified supernatant was then subjected to protein A chromatography and impurities were allowed to flow off this chromatography column. Bound protein including antibody molecules was then eluted from the protein A column, treated at a pH of about 3.3 to 3.7 for about 15 to 240 minutes. This treated preparation was then adjusted to about pH 4.3 to 4.7 and held for about 20 to 1110 minutes. This treated preparation was then clarified through the filtration train of a depth filter and a 0.5/0.2 µm dual layer filter. The filtered preparation was then subjected to Q-SEPHAROSE™ Fast Flow anion exchange chromatography at a load pH of about 8.3 to 8.7 and eluted from the chromatography column. This eluate was then held for about 96 hours or less. Guanidine and ammonium sulfate were then added. Guanidine was added to a concentration of about 1.8 M to 2.2 M and held for about 15 to 240 minutes. This solution was then subjected to phenyl SEPHAROSE™ fast flow chromatography at a load ratio of about 12 g protein/L resin to about 27 g/L resin, an elution gradient volume (bed volumes; BV) of about 9 to about 11, and elution peak cut stop (% of maximum peak height) of about 17 to about 23. Virus filtration was then performed using a Planova 20N virus removal filter. This filtrate was then adjusted to a target concentration of about 46 g protein/L to about 66 g protein/L and the bulk drug substances (BDS) were formulated by tangential filtration and ultrafiltration exchange with a solution comprising about 20 mM sodium phosphate dibasic heptahydrate and 12% weight of sucrose to volume. This solution was then adjusted to a target concentration of 76 g protein/L to about 82 g protein/L and about 0.05% weight of polysorbate 80 to volume was added. This solution was then filtered through 0.5/0.2 µm PES filters and containers of the solution were filled and frozen. Drug product was manufactured using a sterile manufacturing process involving thawing and combining bulk containers followed by filtration of bulk into vials, lyophilization, stoppering and crimping by manufacturing processes well known in the art. The final drug product presentation is a lyophilized drug product in a single use vial.

Lyophilizate from each batch produced was reconstituted by the addition of water to produce a composition comprising 100 mg/mL of protein, the monoclonal anti-IL-5 mepolizumab antibody and 26 mM sodium phosphate dibasic heptahydrate, 15% weight of sucrose to volume and 0.065% weight of polysorbate 80 to volume at a pH of from about 6.8 to about 7.2.

Example 2

Characterization of the Composition

Samples from the batches of composition comprising a monoclonal anti-IL-5 antibody produced as described above were characterized.

Capillary isoelectric focusing (cIEF) consistently showed the presence of six antibody isoforms in the composition (e.g., composition reference standard (RS) 101245722). See FIG. 1. These isoforms are the peak 65, peak 78, peak 88, peak 92, main peak and peak 112 isoforms shown in FIG. 1. Samples of the composition were subjected to cIEF using standard methods. pI 7.9 and pI 9.46 standards were included in samples to be analyzed by cIEF. The cIEF electropherogram shown in FIG. 1 is representative of those for the composition from multiple batches.

The electropherogram shows the composition comprises a main form, acidic forms and basic forms of the antibody. The main form can be seen in FIG. 1 and is also identified as peak 100 in some instances. The acidic forms of the antibody correspond to the peak 65, peak 78, peak 88 and peak 92 forms of FIG. 1. The basic forms of the antibody correspond to the peak 112 forms of FIG. 1.

The formula used for assignment of peaks is as follows: peakname=int{(pIPeak−8)/(pIMain−8)*100} where: int=integer and pIPeak=pI of the peak to be named. Table 7 shows the peak naming convention for cIEF electropherograms of the composition comprising a monoclonal anti-IL-5 antibody. The name of the peaks determined as described here should be verified based on the observed electrophoretic/chromatographic pattern. Peaks that do not fall within the ranges described here should be processed according to the formula above.

TABLE 7

Identification of cIEF peaks

| | Peak | Peak | Peak | Peak | Peak | Peak | Peak | Peak |
|---|---|---|---|---|---|---|---|---|
| Peaks with Retention times greater than | 62 | 75 | 85 | 89 | 100 | 103 | 109 | 120 |

TABLE 7-continued

Identification of cIEF peaks

| | Peak | Peak | Peak | Peak | Peak | Peak | Peak | Peak |
|---|---|---|---|---|---|---|---|---|
| Rention times less than | 68 | 81 | 91 | 95 | 100 | 109 | 115 | 126 |
| Report as Peak | Peak 65 | Peak 78 | Peak 88 | Peak 92 | Peak 100 | Peak 106 | Peak 112 | Peak 123 |

Integral analysis of the electropherogram peaks was performed. See Table 8.

TABLE 8

Total peak area in Select cIEF Electropherograms of Different Composition Batches.

| MDS1 Batch | | | MDS2 Batch | | |
|---|---|---|---|---|---|
| T04L009 | T04M001 | T04N002 | T0414001 (PPQ¹1) | T0414002 (PPQ¹2) | T0414003 (PPQ¹3) |
| Charge Isoforms by cIEF | | | | | |
| Peak area | Peak area | Peak area | Peak area | Peak area | Peak area |
| 61.2% for main; 37.5% for total acidic; 1.2% for total basic | 63.9% for main; 34.4% for total acidic; 1.6% for total basic | 60.6% for main; 38.0% for total acidic; 1.3% for total basic | 58.1% for main; 37.1% for total acidic; 4.9% for total basic | 61.8% for main; 34.1% for total acidic; 4.0% for total basic | 62.3% for main; 33.0% for total acidic; 4.7% for total basic |

This showed the main form represented greater than or equal to 50.0% of the total peak area in the samples (with values between from about 58.1% and 62.3% being observed as well). This also showed the acidic forms represented less than or equal to 45.0% of the total peak area in the samples (with values of between from about 20% to about 45% such as 32.2% and 40.7% being observed as well). The basic forms represented from about 1% to about 15% of the total peak area in the samples (with values of between from about 1.2% to about 4.9% being observed as well).

The main form, acidic forms and basic forms peak fractions produced by cIEF were then further analyzed by weak cation exchange (WCX), trypsin peptide mapping and Liquid Chromatography-Mass Spectroscopy/Mass Spectroscopy (LC-MS/MS) analyses. Standard methods were used for these analyses.

These WCX, trypsin peptide mapping and LC-MS/MS results showed that the main form peak fraction contained two IgG₁ mAb modifications. Thus, in the antibody heavy chain amino acid sequence of SEQ ID NO: 99.6% of the N-terminal glutamine (Gln, Q) was cyclized to pyroglutamic acid (pGlu) and 99.9% of the heavy chain (HC) C-terminal lysine (Lys, K) 449 was cleaved. Typically, the pGlu levels in the batches tested were >95.0% and the level of HC without C-terminal K449 levels was >98.0%.

These WCX, trypsin peptide mapping and LC-MS/MS results also showed for the acid forms peaks that a one-Dalton mass shift characteristic of deamidation was observed. Peptide mapping LC-MS/MS demonstrated the acidic forms peaks contain a mixture of deamidated antibody species. Deamidation was predominantly observed at HC N386 of the amino acid sequence shown in SEQ ID NO: 1 and at LC N31 of the amino acid sequence shown in SEQ ID NO: 2. Lower levels of deamidation were also observed at HC N317 of the amino acid sequence shown in SEQ ID NO: 1.

In its entirety, this experimental data showed asparagine residues HC N317, HC N386, HC N299 of the amino acid sequence shown in SEQ ID NO: 1 and LC N31 of the amino acid sequence shown in SEQ ID NO: 2 were susceptible to deamidation.

These WCX, trypsin peptide mapping and LC-MS/MS showed for the basic forms peaks that the antibody forms in this peak had at least one heavy chain, carboxy terminal lysine amino acid residue intact. Antibody species with intact lysines, relative to other forms in which these are absent, will migrate in the basic region due to additional positive charges from these residues. Thus, the basic forms, such as peak 112, correspond to antibody forms in which one, or both, heavy chain amino acid sequences have the carboxy terminal lysine amino acid sequence shown in SEQ ID NO: 1 intact.

Primary sequencing of the composition comprising a monoclonal anti-IL-5 antibody was also performed by standard LC-MS/MS techniques. These analyses examined the primary struction and amino acid sequence of the antibody molecules in the composition. In particular, these analyses showed which amino acid residues were deamidated, oxidized, cyclized or absent in the anti-IL-5 antibody and the percentage of these in the population of anti-IL-5 antibodies (e.g., expressed from the nucleic acid sequence of SEQ ID NO: 13 and the nucleic acid sequence of SEQ ID NO: 14) present in the composition. See Table 9.

TABLE 9

Primary antibody sequence by peptide mapping LC-MS/MS.

| MDS1 Batch | | | MDS2 Batch | | |
|---|---|---|---|---|---|
| T04L009 | T04M001 | T04N002 | T0414001 (PPQ¹1) | T0414002 (PPQ¹2) | T0414003 (PPQ¹3) |
| Primary Sequence by Peptide Mapping LC-MS/MS | | | | | |
| Deamidation | Deamidation | Deamidation | Deamidation | Deamidation | Deamidation |
| 1.0% of heavy chain (HC or H) asparagine (N) 317; 1.9% of HC N386; 5.8% of light chain (LC or L) N31 | 1.1% of HC N317; 2.2% of HC N386; 6.5% of LC N31 | 1.1% of HC N317; 1.6% of HC N386; 6.2% of LC N31 | 1.1% of HC N317; 1.7% of HC N386; 5.6% of LC N31 | 1.2% of HC N317; 1.6% of HC N386; 6.5% of LC N31 | 1.1% of HC N317; 1.9% of HC N386; 6.2% of LC N31 |

TABLE 9-continued

Primary antibody sequence by peptide mapping LC-MS/MS.

| | MDS1 Batch | | | MDS2 Batch | |
| --- | --- | --- | --- | --- | --- |
| T04L009 | T04M001 | T04N002 | T0414001 (PPQ$^1$1) | T0414002 (PPQ$^1$2) | T0414003 (PPQ$^1$3) |
| HC 1-5 pGlu | HC 1-5 pGlu | HC 1-5 pGlu | HC 1-5 pGlu | HC 1-5 pGlu | HC 1-5 pGlu |
| 93.7%; | 94.6%; | 94.0%; | 93.7%; | 94.6%; | 95.3%; |
| HC 449 Lys Clipped | HC 449 Lys Clipped | HC 449 Lys Clipped | HC 449 Lys Clipped | HC 449 Lys Clipped | HC 449 Lys Clipped |
| 99.2% | 98.4% | 97.6% | 99.2% | 98.9% | 98.5% |
| Oxidation | Oxidation= | Oxidation= | Oxidation= | Oxidation= | Oxidation= |
| 0.9% of HC methionine (M) 64; 1.1% of HC M82/85; 3.0% of HC M254; 0.7% of HC M360; 0.6% of HC M430; 0.8% of LC M4 | 1.0% of HC M64; 0.7% of HC M82/85; 2.9% of HC M254; 0.5% of HC M360; 0.6% of HC M430; 0.4% of LC M4 | 0.8% of HC M64; 0.8% of HC M82/85; 3.1% of HC M254; 0.5% of HC M360; 0.6% of HC M430; 0.5% of LC M4 | 0.7% of HC M64; 0.7% of HC M82/85; 2.6% of HC M254; 0.4% of HC M360; 0.5% of HC M430; 0.3% of LC M4 | 0.8% of HC M64; 0.7% of HC M82/85; 2.7% of HC M254; 0.4% of HC M360; 0.5% of HC M430; 0.4% of LC M4 | 0.7% of HC M64; 0.7% of HC M82/85; 2.7% of HC M254; 0.5% of HC M360; 0.6% of HC M430; 0.5% of LC M4 |

Antibody Variants

Mepolizumab binds to soluble IL-5 and blocks the soluble IL-5 from binding to its receptor. The structure of IL-5 is indicative of a secreted protein and there is no evidence of any membrane-bound forms of IL-5 on any cell types. Thus, the Fc effector functions are not part of the mepolizumab Mechanism Of Action (MOA). Based on the MOA and PK properties of mepolizumab, there are two functions involved in the biological activity of this antibody: binding to IL-5 via the CDRs, and binding to FcRn receptor via the Fc region.

Through the extensive characterization studies performed above and as set out below, it was determined that at least deamidaton, oxidation, and aggregation can lead to antibody variants in the composition of mepolizumab, and that these variants can impact the function of mepolizumab. Specific levels of these variants should be maintained to ensure appropriate biological function. Function is herein described within the acceptable range of 0.70-1.30 specific antigen binding activity (IL5-binding) and 70%-130% FcRn binding. Thus the steps to identify antibody variants that impact function include: (i) is the antibody variant formed, (ii) does the variant have an impact on function, and (iii) what level of variant can result in a functional composition.

Function

IL-5 binding: A statistical analysis was performed to calculate the acceptable antigen binding functional activity range using all drug substance (DS) and drug product (DP) release and stability data generated to date. The calculated statistical range was compared to clinical experience and evaluated based on the known impact of product related variants on potency. Based on this analysis, the acceptable antigen binding functional activity range at time of release and at the end of the shelf-life is specific antigen binding of 0.70-1.30.

The IL-5 specific binding was determined by Surface Plasmon Resonance (SPR) using a BIACORE™ instrument, performed in the binding mode. This SPR assay is able to detect decreases in antigen binding that result from changes in mepolizumab and mepolizumab variants linked to potency.

SPR is used to determine the specific antigen binding activity of mepolizumab. First, mepolizumab reference standard is injected over the surface of a CM5 sensor chip containing immobilized Protein A and then diluted IL-5 protein at a fixed concentration is injected, enabling the IL-5 to bind to the captured mepolizumab sample. The concentration of mepolizumab bound to IL-5, reported as functional binding of mepolizumab to IL-5, is determined from a corresponding mepolizumab reference standard calibration curve. The SPR result was reported as the functional binding concentration of mepolizumab to IL-5, divided by the total protein concentration.

FcRn binding: The Neonatal Fc (FcRn) Receptor Binding activity of mepolizumab was also measured by Surface Plasmon Resonance (SPR) using a BIACORE™ instrument. The acceptable FcRn binding functional activity range was determined to be 70-130%, based on results generated to date during mepolizumab product development, known assay variables, and results generated for similar mAb products.

The Fc region of mepolizumab binds to FcRn, and this interaction reflects the long serum half-life of mepolizumab (mean terminal half-life=20 days). In the SPR assay, a nitrilotriacetic acid (NTA) sensor chip containing immobilized FcRn receptors was used to capture a fixed concentration of mepolizumab. First, $Ni^{2+}$ was injected at a fixed concentration and captured on a NTA sensor chip by chelation of $Ni^{2+}$ through NTA. Second, FcRn receptor was injected at a fixed concentration and the 6× histidine tag at the C-terminus of the alpha chain of the FcRn receptor binds to the $Ni^{2+}$ that had been previously captured. Mepolizumab that had been diluted within the standard curve concentration range was then injected over the surface of the NTA sensor chip containing captured FcRn receptor. The concentration of mepolizumab bound to the FcRn receptor was extrapolated from a corresponding mepolizumab reference standard calibration curve. The SPR result was reported as the functional binding concentration of mepolizumab to the FcRn receptor, divided by the total protein concentration.

The SPR method for specific antigen binding and FcRn binding uses a reference standard of mepolizumab. The mepolizumab reference standard is simply used in assays to obtain system suitability and sample comparability data, to ensure methods are performing appropriately. The reference standard allows the establishment of a calibration curve and concentrations of the samples are interpolated from the curve.

Acidic Variants

Forced degradation studies were then performed to determine the impact of increased levels of acidic variants, for example deamidation, on antibody function/efficacy, i.e., antigen binding and FcRn binding activities.

In pH 9.0 forced degradation studies the composition was adjusted to pH 9.0 with 6N sodium hydroxide and was incubated for 30 days at 40° C. Samples were collected at 0, 3, 7, 14 and 30 days and were compared with the unstressed composition, which was used as a control. The pH 9.0 stressed samples were then analyzed by cIEF. The results are shown in Table 10 and FIG. 1 (day 0 and day 3). The pH 9.0 stressed composition was degraded beyond the capabilities of the cIEF assay at Day 14; therefore, only results up to the day 7 time point are shown in Table 10. At a stressed condition of pH 9.0 for 3 days, the total acidic region was observed to be 74.4% and 71.9% for two different batches of the composition.

TABLE 10 cIEF data summary for pH 9.0 forced degradation studies.

| Condition | Primary Manufacturing Process/Batch | Day | Main Peak | Area (%) Total Acidic | Total Basic |
|---|---|---|---|---|---|
| Control | | | 62.9 | 35.9 | 1.2 |
| Elevated pH 9.0 | MDS1 T004L003S | 0 | 62.5 | 36.1 | 1.4 |
| | | 3 | 24.8 | 74.4 | 0.8 |
| | | 7 | 8.3 | 91.7 | 0.0 |
| | MDS2 T0413010 | 0 | 63.7 | 33.3 | 3.0 |
| | | 3 | 26.9 | 71.9 | 1.2 |
| | | 7 | 11.4 | 88.3 | 0.3 |

The pH 9.0 forced degradation study samples of the composition from different batches were then tested for specific antigen binding activity (Table 11) and FcRn binding activity (Table 12) using standard surface plasmon resonance (SPR) methods.

TABLE 11

Data summary of specific antigen binding activity (e.g., human IL-5 binding activity) measured by SPR in pH 9.0 forced degradation study samples of the composition from different batches.

| Condition | Primary Manufacturing Process/Batch | Day | Specific Antigen Binding Activity |
|---|---|---|---|
| Elevated pH 9.0 | MDS1 T04L003S | 0 | 0.96 |
| | | 3 | 0.74 |
| | | 7 | 0.60 |
| | MDS2 T0413010 | 0 | 0.94 |
| | | 3 | 0.74 |
| | | 7 | 0.62 |

TABLE 12

FcRn binding measured by SPR in pH 9.0 forced degradation study samples of the composition from different batches.

| Condition | Primary Manufacturing Process/Batch | Day | FcRn Binding (%) |
|---|---|---|---|
| Elevated pH 9.0 | MDS1 T04L003S | 0 | 91 |
| | | 3 | 84 |
| | | 7 | 82 |
| | MDS2 T0413010 | 0 | 86 |
| | | 3 | 82 |
| | | 7 | 80 |

The IL5 specific binding activity at Day 3 (i.e., about 72-74% acidic variant) was 0.74 for both batches of the composition subjected to pH 9.0 forced degradation. The FcRn binding activities were 82% and 80% respectively for both batches of the composition subjected to pH 9.0 forced degradation. These values were within the acceptance criteria for each assay. The acceptance criterion for specific antigen binding activity is 0.70-1.30 and the acceptance criterion for FcRn binding is 70%-130%. Thus, acidic variant can be as high as about 74% to maintain function of the mepolizumab composition.

Deamidation

Forced degradation studies can determine which residues that appear to be susceptible to deamidation actually deamidate, and whether the deamidated variant has an impact on function, and what levels of deamidation are acceptable within a composition to maintain function. The asparagine residues which were experimentally determined to be susceptible to deamidation are HC N317, HC N386, HC N299, and LC N31. Forced degradation studies were performed to determine the impact of increased levels of deamidation LC N31 in the antibody light chain amino acid sequence shown in SEQ ID NO: 2 on antigen binding activity. In these studies the composition from different batches was adjusted to pH 9.0 with 6N sodium hydroxide and was incubated for 30 days at 40° C. Samples were collected at 0, 3, 7, 14 and 30 days and were compared with unstressed composition (e.g., reference standard) which was used as a control. The pH 9.0 stressed samples were tested by peptide mapping LC-MS/MS. The results are shown in Table 13. When mepolizumab is held at pH 9.0 for 3 days the level of deamidated LC N31 in the antibody light chain amino acid sequence shown in SEQ ID NO: 2 is 17.4% and 16.8% for different batches of the composition. See Table 13. Antigen and FcRN binding data for mepolizumab held at pH 9.0 for 3 days are presented in Table 11 and Table 12.

TABLE 13

Percentage deamidation by peptide mapping LC-MS/MS in pH 9.0 forced degradation study samples of the composition from different batches at day 3.

| Condition | Primary Manufacturing Process/Batch | Deamidation (%) | | | |
|---|---|---|---|---|---|
| | | HC N317 | HC N386 | LC N31 | HC N299 |
| control | | 0.8 | 5.5 | 5.2 | 0.2 |
| Elevated pH 9.0 | MDS1 T04L003S | 0.9 | 28.2 | 17.4 | 1.3 |
| | MDS2 T0413010 | 1.0 | 27.8 | 16.8 | 1.3 |

Therefore at Day 3, the specific antigen binding activity of 0.74 (Table 11), and FcRn binding activity of 84% and 82% (Table 12), show that deamidation at N31 of up to around 17%, and deamidation at N386 of up to around 28% (Table 13), can maintain a functional composition within the acceptable range of 0.70-1.30 specific antigen binding activity and 70%-130% FcRn binding.

Oxidation

Forced degradation studies were performed to experimentally examine the susceptibility of methionine and other amino acid residues in the antibody heavy and light chains of the composition to oxidation. Forced degradation studies can determine which residues that appear to be susceptible to oxidation actually oxidize, and whether the oxidized variant has an impact on function, and what levels of oxidation are acceptable within a composition to maintain function/efficacy (antigen binding and/or FcRn binding).

Samples of the composition were incubated with 0.1% hydrogen peroxide ($H_2O_2$) for 48 hours at room temperature (RT) to induce oxidation. Samples were collected at 0, 6, 12, 24, and 48 hours. These were compared with unstressed composition (e.g., reference standard) which was used as a control. It was determined from these studies the methionine (M) residues most prone to oxidation include HC M64, HC M82, HC M85, HC M254, HC M360, HC M430 of the antibody heavy chain amino acid sequence shown in SEQ ID NO: 1 and LC M4 of the antibody light chain amino acid sequence shown in SEQ ID NO: 2. The methionine (M) residues most prone to oxidation include M64, which is located in the HC CDR2; M254 and M430, which are located in the FcRn and Protein A binding pocket in the Fc region; and M360 of the antibody heavy chain amino acid sequence shown in SEQ ID NO: 1. Methionine residues prone to oxidation to a lesser extent included HC M4, HC M82, and HC M85 of the antibody heavy chain amino acid sequence shown in SEQ ID NO: 1. In addition, LC C220 of the antibody light chain amino acid sequence shown in SEQ ID NO: 2 was determined to be prone to oxidation under chemically induced conditions. Importantly, LC C220 and HC C222 form the inter-chain disulfide bond that joins the heavy and light chains.

The levels of sulfoxide resulting from methionine oxidation and of sulfonic acid resulting from cysteine oxidation were measured using peptide mapping LC-MS/MS and is summarized in Table 14. HC M64, M254, M360, and M430 were more than 70% oxidized at 48 hours after incubation with 0.1% hydrogen peroxide ($H_2O_2$).

TABLE 14

Percentage oxidation determined by peptide mapping LC-MS/MS in study samples of the composition from different batches after treatment with $H_2O_2$ for 48 hours.

| Primary Manufacturing Process | BDS Batch | \multicolumn{7}{c}{Oxidation (%)} |
|---|---|---|---|---|---|---|---|---|
| | | HC M64 | HC M254 | HC M360 | HC M430 | HC M82 and 85 | LC M4 | LC C220 |
| Control | | 0.9 | 3.5 | 0.5 | 0.5 | 0.3 | 0.2 | 0.0 |
| MDS1 | T04L003S | 72.9 | 99.9 | 98.5 | 95.6 | 3.2 | 0.8 | 7.6 |
| MDS2 | T0413010 | 85.6 | 99.8 | 98.1 | 98.7 | 3.5 | 1.0 | 7.2 |

Specific antigen binding by the antibodies in the composition was measured by SPR. This demonstrated a greater decrease in specific antigen binding activity at 48 hours in different $H_2O_2$ stressed batches as summarized in Table 15. This decrease in antigen binding correlates with the relatively higher levels of M64 oxidation observed by peptide mapping LC-MS/MS. The specific antigen binding activities in the tested samples from the different batches of the composition decreased by approximately 15% and 32%, respectively. When mepolizumab was 85.6% oxidized specific antigen binding activity was still retained at 0.57. The linear relationship between the cumulative levels of oxidation in mepolizumab and specific antigen binding activity was used and it was determined, at worst case, that HC M64 could be approximately 50% oxidized and the antibodies in the composition would still retain the antigen binding activity in the range of 0.70-1.30.

TABLE 15

Specific antigen binding activity measured by SPR in different batches of the composition treated with $H_2O_2$ for 48 hours.

| Primary Manufacturing Process/Batch | Condition | Time (hours) | Specific Antigen Binding Activity |
|---|---|---|---|
| MDS1 T04L003S | Oxidation Control | 0 | 0.92 |
| | | 48 | 0.92 |
| | 0.1% $H_2O_2$ | 0 | 0.91 |
| | | 48 | 0.76 |
| MDS2 T0413010 | Oxidation Control | 0 | 0.96 |
| | | 48 | 0.96 |
| | 0.1% $H_2O_2$ | 0 | 0.89 |
| | | 48 | 0.57 |

The FcRn binding activity profiles of $H_2O_2$ stressed samples from different batches of the composition were highly similar with a substantial decrease in the FcRn binding activity at 48 hours compared with the controls (untreated reference standard) as shown in Table 16. HC M254 and HC M430 are located in the Fc region and when oxidized have been shown to result in a decrease in FcRn binding. Based on peptide mapping results generated during the forced degradation studies, when the composition is chemically oxidized with $H_2O_2$ for 48 hours, the levels of oxidized HC M254 and HC M430 observed in the different batches is ≥95%. The FcRn binding results showed approximately an 80% decrease in antigen FcRn binding in the $H_2O_2$ stressed samples from different batches of the composition. When mepolizumab was ≥90% oxidized FcRn binding activity was still retained at 22%. The linear relationship between the cumulative levels of oxidation in mepolizumab and FcRn binding activity was used and it was determined, at worst case, the HC M254 and HC M430 could be 50% oxidized and the antibodies in the composition would still retain the FcRn binding activity in the range of 70%-130%.

TABLE 16

FcRn binding activity measured by SPR in different batches of the composition treated with $H_2O_2$ for 48 hours.

| Primary Manufacturing Process/Batch | Condition | Time (hours) | FcRn Binding Activity (%) |
|---|---|---|---|
| MDS1 T04L003S | Oxidation Control | 0 | 97 |
| | | 48 | 94 |
| | 0.1% $H_2O_2$ | 0 | 79 |
| | | 48 | 22 |
| MDS2 T0413010 | Oxidation Control | 0 | 97 |
| | | 48 | 98 |
| | 0.1% $H_2O_2$ | 0 | 77 |
| | | 48 | 17 |

A photo stress study was conducted to determine the impact of light induced tryptophan oxidation on the antigen binding activity of the antibodies in different batches of the composition. This showed tryptophan W52 in the antibody heavy chain is prone to oxidation. For these studies the composition from different batches was exposed to 1.8 million lux-hr of visible light over approximately 60 hours at 25° C. to induce photo stress. Samples collected at 0, 3, 7, 14, and 30 hours were compared with an unstressed reference standard of the composition which was used as a control. The levels of di-oxidation/kynureninie resulting from tryptophan oxidation were highly similar in the different batches of light exposure stressed composition as summarized in Table 17. Increases in HC W52 oxidation were detected after 60 hours of light exposure.

TABLE 17

Percentage oxidation measured by peptide mapping LC-MS/MS in different batches of the composition after light exposure stress for 60 hours.

| Primary Manufacturing | Oxidation Level (%) | |
|---|---|---|
| Process/Batch | W52 (+32 Da) | W52 (+4 Da) |
| control | 0.1 | 0.0 |
| MDS1 T04L003S | 3.3 | 3.4 |
| MDS2 T0413010 | 3.5 | 4.6 |

Specific antigen binding activity profiles of the antibodies in the different batches of light exposure stressed composition showed a decrease in specific antigen binding activity over time. This is summarized in Table 18. When mepolizumab was approximately 7% oxidized specific antigen binding activity was still retained at 0.53. The linear relationship between the cumulative levels of tryptophan oxidation in mepolizumab and specific antigen binding activity was used and it was determined, at worst case, W52 could be 3% oxidized and the antibodies in the composition would still retain the antigen binding activity in the range of 0.70-1.30.

TABLE 18

Specific Antigen Binding Activity measured by SPR in different batches of the composition after light exposure stress for 60 hours.

| Primary Manufacturing Process/Batch | Condition | Day | Specific Antigen Binding Activity |
|---|---|---|---|
| MDS1 T04L003S | Light Exposure | 0 | 0.89 |
| | Control | 60 | 0.89 |
| | Light Exposed | 0 | 0.89 |
| | | 60 | 0.53 |
| MDS2 T0413010 | Light Exposure | 0 | 0.93 |
| | Control | 60 | 0.93 |
| | Light Exposed | 0 | 0.93 |
| | | 60 | 0.55 |

Thus, to maintain function (IL-5 binding, and/or FcRn binding), HC M64 could be up to 50% oxidized, HC M254 and HC M430 could be up to 50% oxidized, and W52 could be up to 3% oxidized.

Aggregation

Figure 3:
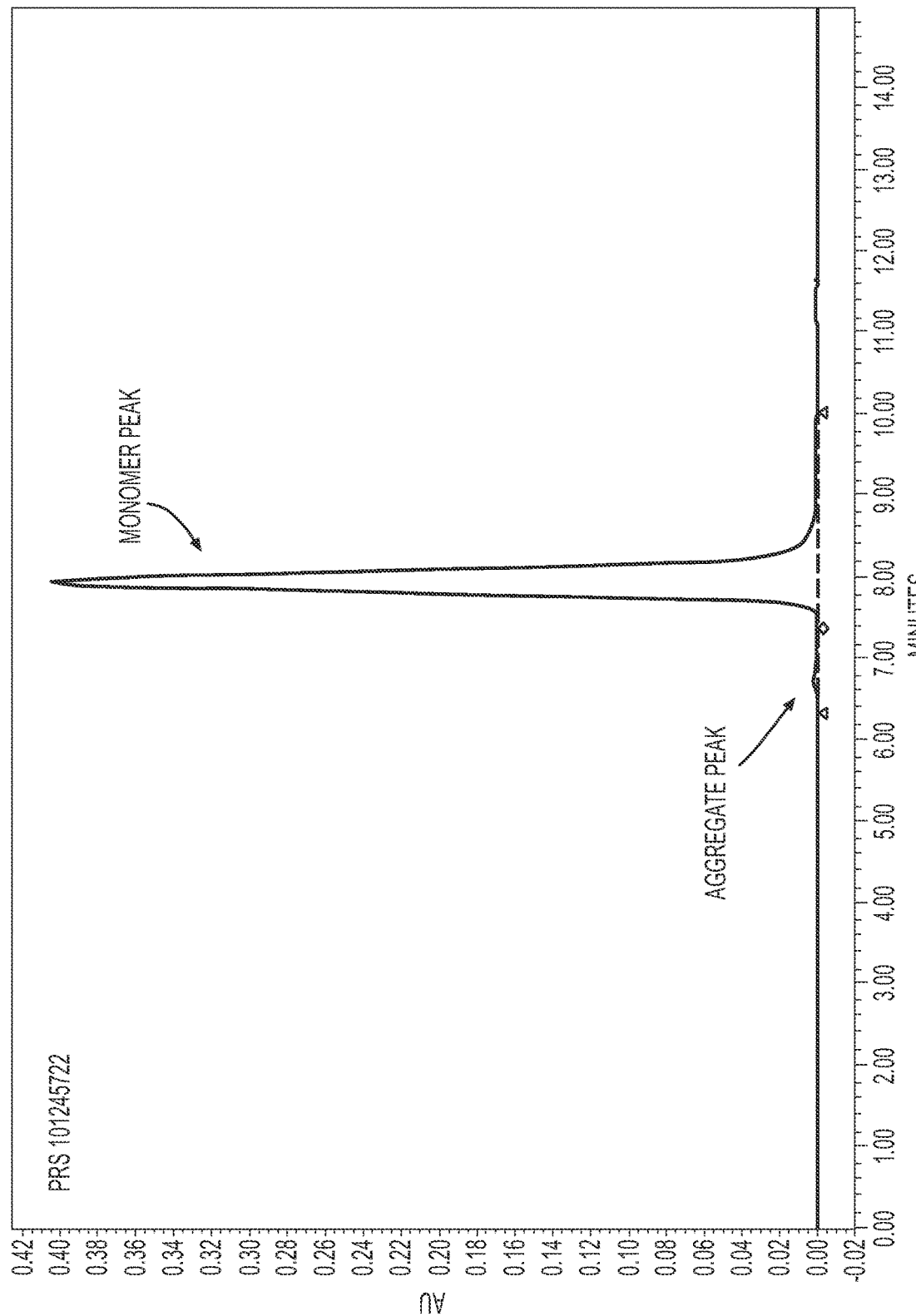
FIG. 3. Representative full view size exclusion chromatography (SEC) chromatogram of a RS composition comprising mepolizumab.
Figure 4:
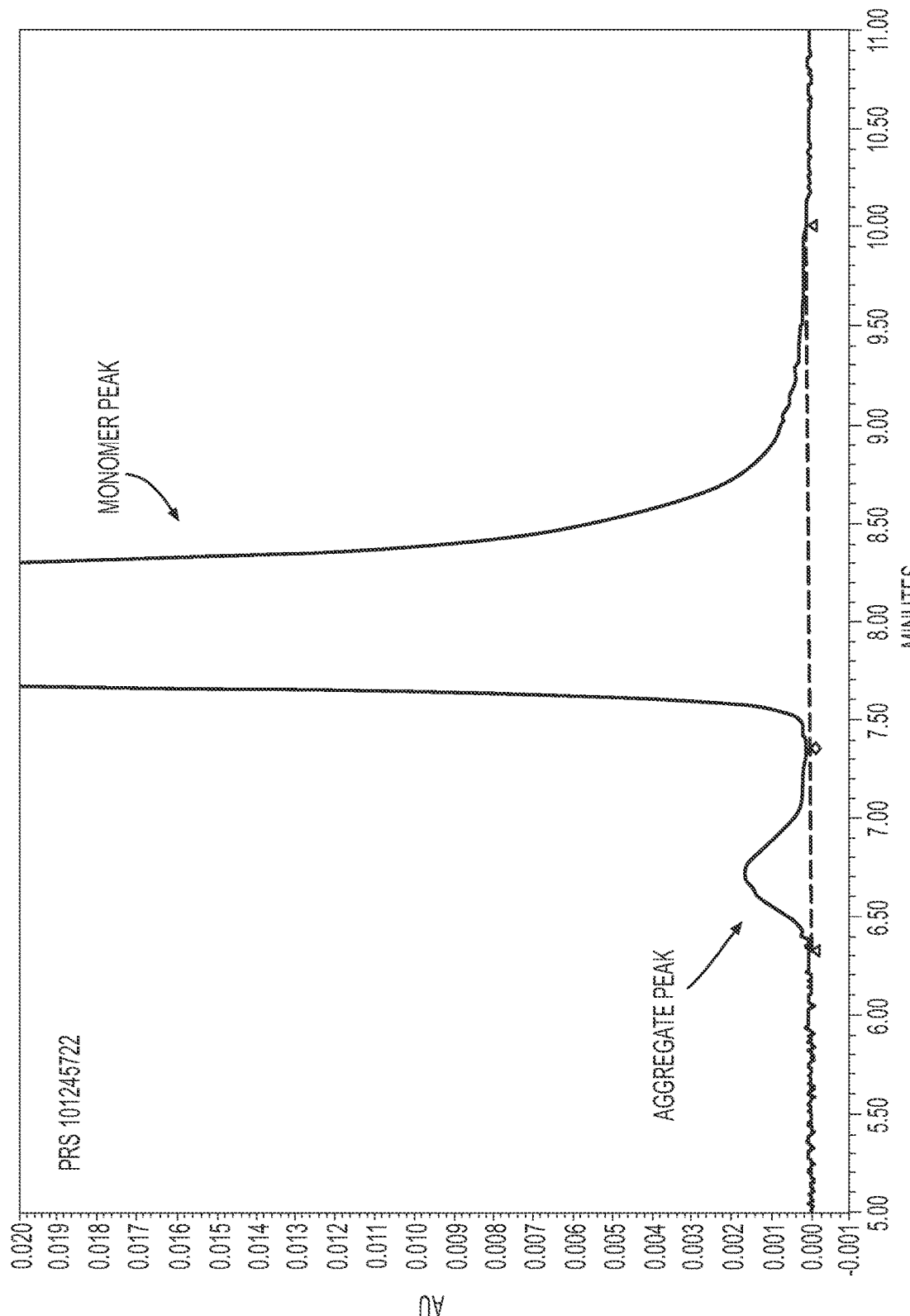
FIG. 4. Representative expanded view SEC chromatogram of a RS composition comprising mepolizumab.

The size distribution of the antibodies in the composition was monitored by using standard non-denaturing size exclusion chromatography (SEC) methods. Three peaks were detected in the RS composition SEC profile as shown in FIG. 3 and FIG. 4. A main peak at 7.9 minutes with a relative percentage area of 99.4% was identified as monomer; a minor peak at approximately 6.7 minutes with a relative percentage area of 0.5% was identified as aggregate. A second minor peak has been observed in some batches, eluting after the main peak which indicates the presence of fragment. Typically this peak is below the SEC assay QL of 0.1.

Figure 5:
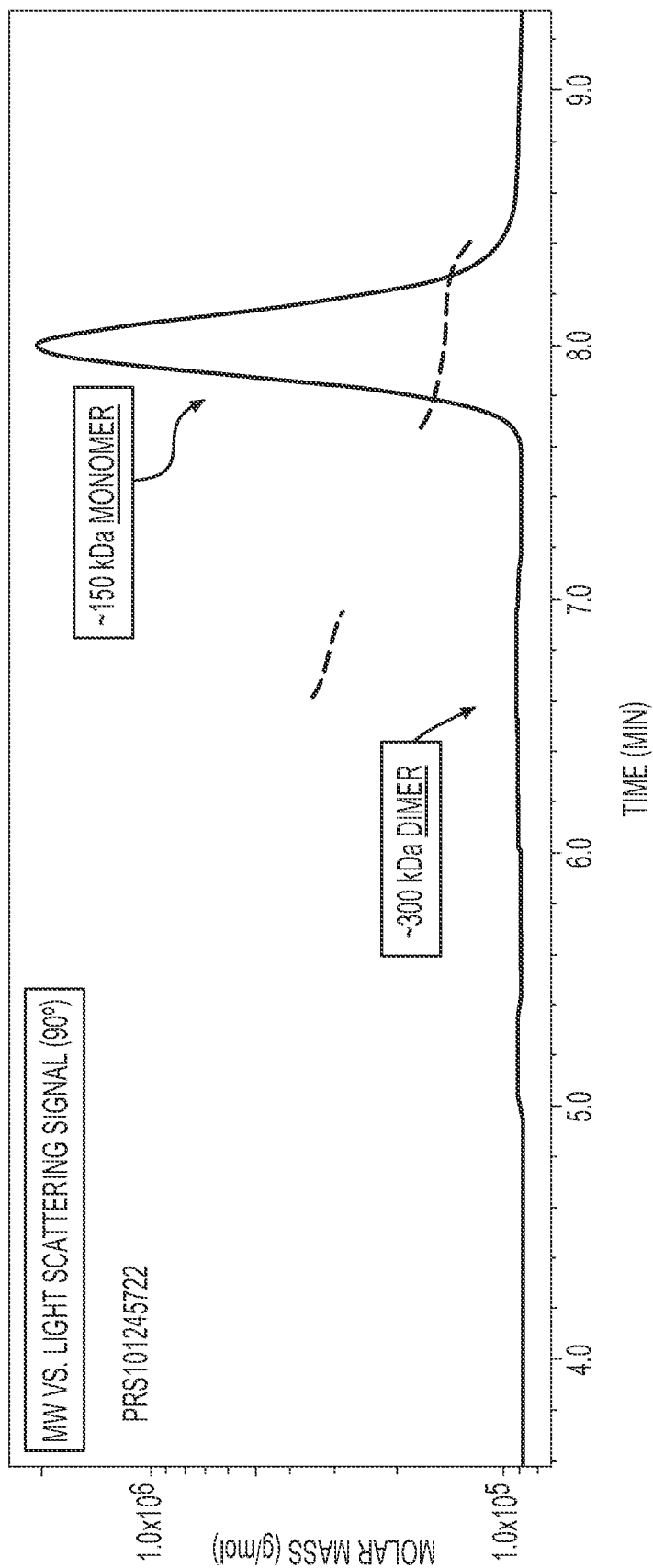
FIG. 5. Representative SEC-multi-angle light scattering (MALS) chromatogram of a RS composition comprising mepolizumab.
Figure 6:
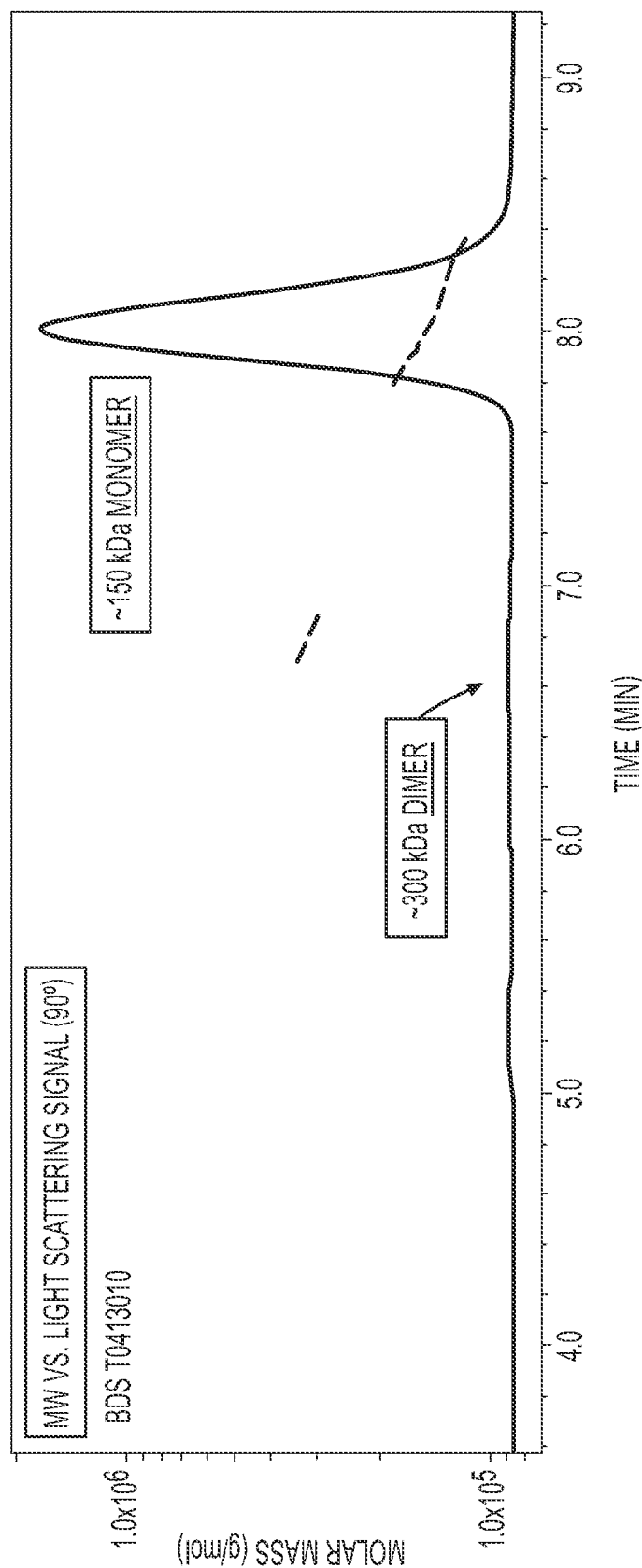
FIG. 6. Representative SEC-MALS chromatogram of a batch of the composition comprising mepolizumab.

The aggregate peak was further characterized using SEC with multi-angle light scattering (MALS) detection and analytical ultracentrifugation (AUC). Results show that the SEC-MALS profiles contain an early eluting peak (dimer) and a later eluting peak (monomer) as shown in FIG. 5 for the RS composition and FIG. 6 for a different batch of the composition. The line that cross-sects each peak represents the molar mass of the detected species and the position of the dimer peak, which is not readily visible in the chromatograms due to the low abundance of dimer in the samples.

The SEC-MALS data was used to calculate the molar mass of the antibody monomers and dimers. The resulting molar mass of the monomers in the RS composition and for a different batch of the composition was comparable to the mepolizumab monomer theoretical mass of 148,760 kDa as shown in Table 19. Variability was detected in the molecular weight observed for the dimer due to the low level of this species present in the sample.

TABLE 19

SEC-MALS analysis of the monomers in the RS composition and for a different batch of the composition.

| | Molar mass (kDa) | |
|---|---|---|
| Mepolizumab Sample | Monomer | Dimer |
| Reference Standard RS 101245722 | 147 | 304 |
| Batch T0413010 | 147 | 340 |

Sedimentation velocity area under the curve (AUC) integral analysis was used as a complementary technique to fraction based methods including SEC to confirm there is no perturbation of self association equilibrium or exclusion of higher order aggregate from the chromatographic separation. The results of AUC analysis demonstrated the c(s) distribution contains one dominant species (main peak), identified as monomer, with a sedimentation coefficient for both the RS batch of the composition and another batch of the composition of 2.81 S; and one aggregate peak, identified as dimer, with a sedimentation coefficient of 4.87 S for the RS batch of the composition and 5.10 S for another batch of the composition as shown in Table 20. The difference in sedimentation coefficient values between the PRS and BDS is not considered substantial and is attributed to the low abundance of dimer within the samples. The only high molecular weight species detected was dimer, which is consistent with SEC-UV and SEC-MALS results.

TABLE 20

AUC Analysis of different batches of the composition

| Mepolizumab Sample | Sedimentation Coefficient | | Molecular Weight kDa | | Abundance | |
|---|---|---|---|---|---|---|
| (n = 3) | Monomer | Dimer | Monomer | Dimer | Monomer | Dimer |
| PRS 101245722 | 2.81 | 4.87 | 137 | 336 | 99.1% | 0.9% |
| BDS T0413003 | 2.81 | 5.10 | 136 | 353 | 99.3% | 0.7% |

The sedimentation coefficients determined for monomer and dimer were lower than the traditionally observed values for $IgG_1$ monoclonal antibodies. The formulation of mepolizumab contains 12% (w/v) sucrose, resulting in a highly viscous sample which causes the lower sedimentation coefficients observed for these antibody molecules in the composition. The results of the SEC-UV, SEC-MALS, and AUC analysis show that the aggregate species in the composition is antibody dimer.

To investigate the impact of aggregate on antigen binding activity, a low pH study was conducted on the composition from different batches. Composition samples from the different batches were adjusted to pH 3.5 with 5N hydrochloric acid. The pH 3.5 adjusted samples were then incubated for 30 days at 40° C. to induce chemical modifications. Samples collected at 0, 3, 7, 14 and 30 days were compared with an unstressed RS sample of the composition, which was used as a control. This showed when the composition is chemically stressed at low pH 3.5, aggregation is one of the primary degradation pathways.

Figure 7:
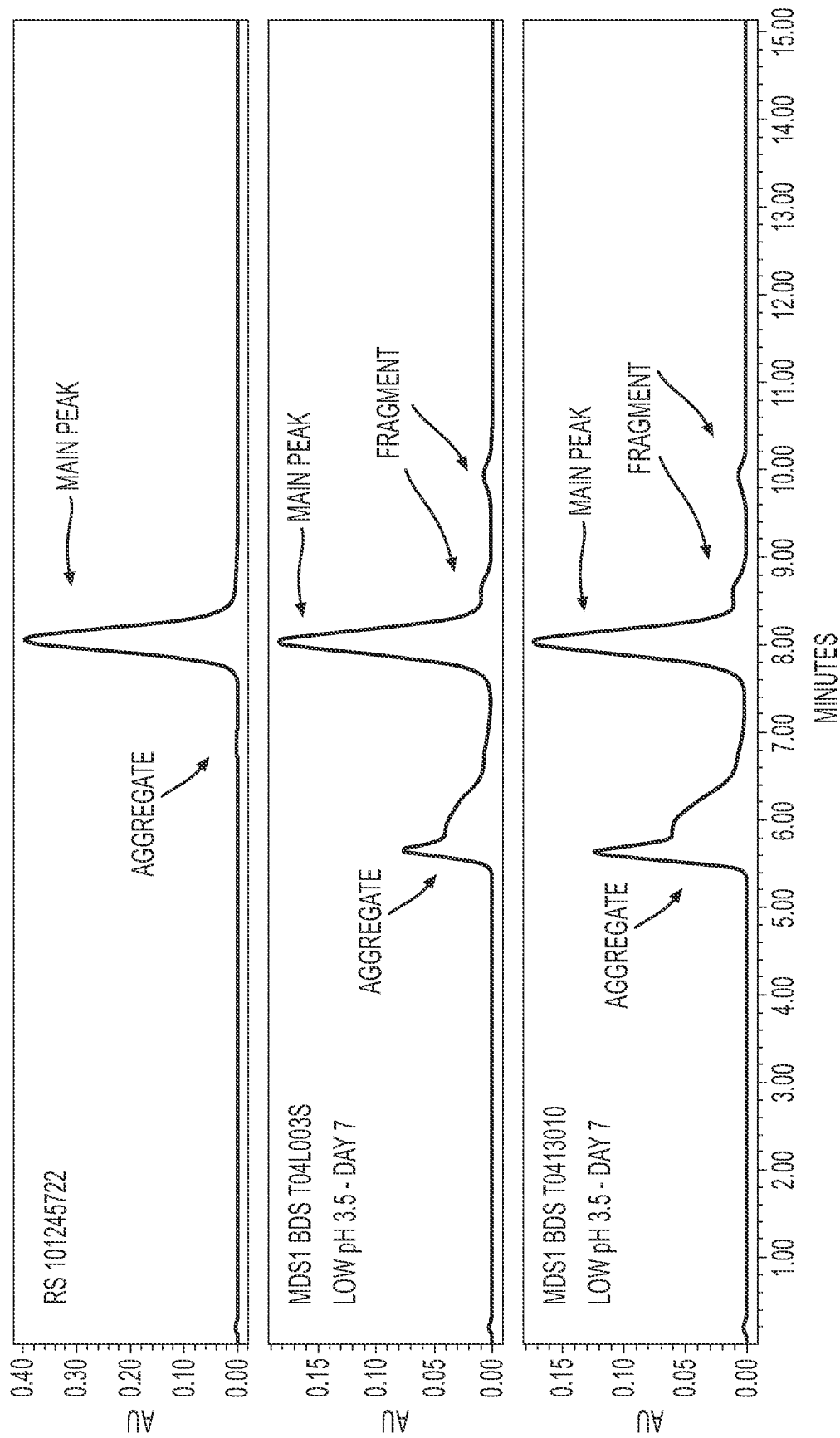
FIG. 7. Representative SEC Chromatograms of a RS composition comprising mepolizumab and for different batches of pH 3.5 stressed composition comprising mepolizumab at Day 7.

SEC degradation profiles of pH 3.5 stressed samples of the composition are shown in FIG. 7 and summarized in Table 21. Under low pH 3.5 stress conditions, different rates of aggregation where observed between the different batches of composition. However, by day 30 both batches of the composition reach equilibrium and exhibit similar levels of aggregation. This difference in aggregation rate between the different batches is attributed to the higher level of covalent dimer versus non-covalent dimer in the batches. The slower aggregation rate observed in the MDS1 batch of the composition is attributed to the higher proportion of non-covalent dimer relative to that of the MDS2 batch; non-covalent dimer associates and dissociates until equilibrium is reached, which may slow the overall rate of aggregate formation.

TABLE 21

SEC data summary for an untreated RS batch of the composition and pH stressed batches of the composition.

| Condition | Primary Manufacturing Process/Batch | Day | Area (%) | | |
|---|---|---|---|---|---|
| | | | Monomer | Aggregate | Fragment |
| control | | | 99.6 | 0.4 | 0.0 |
| Low pH 3.5 | MDS1 T004L003S | 0 | 99.0 | 1.0 | 0.0 |
| | | 3 | 81.4 | 14.3 | 4.2 |
| | | 7 | 59.3 | 35.4 | 5.2 |
| | | 14 | 47.9 | 44.4 | 7.7 |
| | | 30 | 36.8 | 51.2 | 12.0 |
| | MDS2 T0413010 | 0 | 98.4 | 1.6 | 0.1 |
| | | 3 | 56.5 | 40.5 | 3.1 |
| | | 7 | 48.3 | 46.9 | 4.8 |
| | | 14 | 41.9 | 50.7 | 7.4 |
| | | 30 | 34.0 | 54.4 | 11.5 |

Specific antigen binding activity profiles of samples of the pH 3.5 stressed batches of the composition showed a decrease in specific antigen binding activity over time as summarized in Table 22.

TABLE 22

Data summary of specific antigen binding activity measured by SPR in samples of pH stressed batches of the composition.

| Condition | Primary Manufacturing Process/Batch | Day | Specific Antigen Binding Activity (mg/mL) |
|---|---|---|---|
| Low pH 3.5 | MDS1 T04L003S | 0 | 0.92 |
| | | 3 | 0.56 |
| | | 7 | 0.43 |
| | MDS2 T0413010 | 0 | 0.95 |
| | | 3 | 0.57 |
| | | 7 | 0.43 |

The FcRn binding activity profiles of samples of the pH 3.5 stressed batches of the composition showed a decrease in FcRn binding activity over time as summarized in Table 23.

TABLE 23

Data summary of FcRn binding measured by SPR in pH stressed batches of the composition.

| Condition | Primary Manufacturing Process/Batch | Day | FcRn Binding (%) |
|---|---|---|---|
| Low pH 3.5 | MDS1 T04L003S | 0 | 90 |
| | | 3 | 54 |
| | | 7 | 46 |
| | MDS2 T0413010 | 0 | 86 |
| | | 3 | 51 |
| | | 7 | 43 |

In summary, Tables 21-23 show that there is approximately a 50% decrease in antigen binding and FcRn binding when there is approximately 40% aggregate present in the sample. When mepolizumab was approximately 40% aggregated, specific antigen binding activity was still retained at 0.57 and FcRn binding activity was retained at 51% (Table 22 MDS2 Day 3). There was a slightly different degradation profile for aggregate content between MDS1 and MDS2 at Day 3 (Table 21) because of the different ratios of covalent versus non-covalent dimer.

The linear relationship between the aggregation in mepolizumab and specific antigen and FcRn binding activities was used from MDS2 and it was determined, at worst case, mepolizumab could be 20% aggregate and the antibodies in the composition would still retain the antigen binding activity in the range of 0.70-1.30 and FcRn binding activity of 70-130%.

Therefore, it is possible for the antibodies in the composition comprising mepolizumab to be 20% aggregated and still retain IL-5 binding activity in the range of 0.70-1.30 and FcRn binding activity in the range of 70%-130%.

HCP

Residual CHO host cell protein levels in the mepolizumab composition are measured using an enzyme-linked immunosorbent assay (ELISA). This method uses antibodies produced against native antigens of the CHO cell line grown under conditions that mimic the production process conditions of mepolizumab.

It was determined that for the mepolizumab composition, an acceptable range for HCP content is ≤10 ng/mg. This range is derived from release data generated to date and represents the true analytical and process variability. 37 different batches of drug substance had the following HCP content: 1.1 ng/mg (2 batches), 1.0 ng/mg (5 batches), 0.9 ng/mg (1 batch), 0.8 ng/mg (3 batches), 0.7 ng/mg (1 batch), 0.6 (1 batch), 0.5 ng/mg (1 batch), ≤0.5 ng/mg (4 batches), ≤1 ng/mg (19 batches).

In summary, there are two predominant functions involved in the biological activity of mepolizumab: binding to IL-5 via the CDRs, and binding to FcRn receptor via the Fc region. Through the extensive characterization studies performed above, it was determined that particular deamidated antibody variants, particular oxidated antibody variants, and aggregated antibody variants, can impact the function of the composition of mepolizumab. Therefore, specific levels of these variants should be maintained to ensure appropriate function/efficacy.

Example 3

Informal Sequence Listing

Underlining below identifies CDR sequences, according to the Kabat definition of CDRs, in the variable heavy and variable light chain portions of the antibodies or the nucleic acid sequences encoding these CDR sequences. For example, in SEQ ID NO: 1 the frameworks and CDRs are presented as plaintext framework1, underlined CDR1, plaintext framework2, underlined CDR2, plaintext framework3, underlined CDR3 and plaintext framework4 in order from the amino proximal portion to the carboxy terminal portion of the sequences presented. Asterisks to the right of a character for a single letter amino acid code indicates the amino acid residue to the left is a N-glycosylation site. This scheme is used in SEQ ID NO:s 1-4, 11, 12 and 19-22, etc. for example Amino terminal methionine residues shown in these sequences can be cleaved. Thus, the sequences here showing an amino terminal methionine residue should also be considered to disclose the cleaved versions of these proteins lacking such an amino terminal methionine residue. Nucleic acids sequences are presented as DNA nucleic acid sequences and include "t" nucleic acid residues, the corresponding RNA sequence should also be considered as disclosed such that "t" nucleic acid residues may also be regarded as disclosing a "u" nucleic acid residue. Additionally, the 5' proximal "atg" start codon and the 3' proximal "taa," "tag," and "tga" stop codons have been omitted from the cDNA nucleic acid sequences below. This is the case for SEQ ID NO:s 31-34, etc. for example.

```
MEPOLIZUMAB FULL LENGTH HEAVY CHAIN
                                                                        SEQ ID NO: 1
QVTLRESGPALVKPTQTLTLTCTVSGFSLTSYSVHWVRQPPGKGLEWLGVIWASGGT

DYNSALMSRLSISKDTSRNQVVLTMTNMDPVDTATYYCARDPPSSLLRLDYWGRGT

PVTVSSASTKGPSVFPLAPSSKSTSGGTAALGCLVKDYFPEPVTVSWNSGALTSGVHT

FPAVLQSSGLYSLSSVVTVPSSSLGTQTYICNVNHKPSNTKVDKRVEPKSCDKTHTCP

PCPAPELLGGPSVFLFPPKPKDTLMISRTPEVTCVVVDVSHEDPEVKFNVVYVDGVEV

HNAKTKPREEQYN*STYRVVSVLTVLHQDWLNGKEYKCKVSNKALPAPIEKTISKAK

GQPREPQVYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPGK

MEPOLIZUMAB FULL LENGTH LIGHT CHAIN
                                                                        SEQ ID NO: 2
DIVMTQSPDSLAVSLGERATINCKSSSLLNSGNQKNYLAWYQQKPGQPPKLLIYGA

STRESGVPDRFSGSGSGTDFTLTISSLQAEDVAVYYCQNVHSFPFTFGGGTKLEIKRTV

AAPSVFIFPPSDEQLKSGTASVVCLLNNFYPREAKVQWKVDNALQSGNSQESVTEQD

SKDSTYSLSSTLTLSKADYEKHKVYACEVTHQGLSSPVTKSFNRGEC

MEPOLIZUMAB VH
                                                                        SEQ ID NO: 3
QVTLRESGPALVKPTQTLTLTCTVSGFSLTSYSVHWVRQPPGKGLEWLGVIWASGGT

DYNSALMSRLSISKDTSRNQVVLTMTNMDPVDTATYYCARDPPSSLLRLDYWGRGT

PVTVSS

MEPOLIZUMAB VL
                                                                        SEQ ID NO: 4
DIVMTQSPDSLAVSLGERATINCKSSQSLLNSGNQKNYLAWYQQKPGQPPKLLIYGA

STRESGVPDRFSGSGSGTDFTLTISSLQAEDVAVYYCQNVHSFPFTFGGGTKLEIK

MEPOLIZUMAB CDRH1
                                                                        SEQ ID NO: 5
SYSVH

MEPOLIZUMAB CDRH2
```

-continued

VIVVASGGTDYNSALMS

MEPOLIZUMAB CDRH3                                                          SEQ ID NO: 7

DPPSSLLRLDY

MEPOLIZUMAB CDRL1                                                          SEQ ID NO: 8

KSSQSLLNSGNQKNYLA

MEPOLIZUMAB CDRL2                                                          SEQ ID NO: 9

GASTRES

MEPOLIZUMAB CDRL3                                                          SEQ ID NO: 10

QNVHSFPFT

HUMAN IL-5 (MATURE PROTEIN)                                                SEQ ID NO: 11

IPTEIPTSALVKETLALLSTHRTLLIANETLRIPVPVHKNHQLCTEEIFQGIGTLESQTVQ

GGTVERLFKNLSLIKKYIDGQKKKCGEERRRVNQFLDYLQEFLGVMNTEWIIES

HUMAN IL-5 RECEPTOR SUBUNIT ALPHA ISOFORM 1 (MATURE PROTEIN)                SEQ ID NO: 12

DLLPDEKISLLPPVNFTIKVTGLAQVLLQWKPNPDQEQRNVNLEYQVKINAPKEDDY

ETRITESKCVTILHKGFSASVRTILQNDHSLLASSWASAELHAPPGSPGTSIVNLTCTTN

TTEDNYSRLRSYQVSLHCTWLVGTDAPEDTQYFLYYRYGSWTEECQEYSKDTLGRN

IACWFPRTFILSKGRDWLAVLVNGSSKHSAIRPFDQLFALHAIDQINPPLNVTAEIEGT

RLSIQWEKPVSAFPIHCFDYEVKIHNTRNGYLQIEKLMTNAFISIIDDLSKYDVQVRAA

VSSMCREAGLWSEWSQPIYVGNDEHKPLREWFVIVIMATICFILLILSLICKICHLWIK

LFPPIPAPKSNIKDLFVTTNYEKAGSSETEIEVICYIEKPGVETLEDSVF

DNA ENCODING MEPOLIZUMAB FULL LENGTH HEAVY CHAIN                            SEQ ID NO: 13 caggttaccctgcgtgaatccggtccggcactagttaaaccgacccagaccctgacgttaacctgcaccgtctccggtttctccctgacg agctatagtgtacactgggtccgtcagccgccgggtaaaggtctagaatggctggtgtaatatgggctagtggaggcacagattataa ttcggctctcatgtcccgtctgtcgatatccaaagacacctcccgtaaccaggttgttctgaccatgactaacatggaccggttgacacc gctacctactactgcgctcgagatcccccttcttccttactacggcttgactactggggtcgtggtaccccagttaccgtgagctcagcta gtaccaagggcccatcggtcttccccctggcaccctcctccaagagcacctctgggggcacagcggccctgggctgcctggtcaagg actacttccccgaaccggtgacggtgtcgtggaactcaggcgccctgaccagcggcgtgcacaccttcccggctgtcctacagtcctc aggactctactccctcagcagcgtggtgaccgtgccctccagcagcttgggcacccagacctacatctgcaacgtgaatcacaagccc agcaacaccaaggtggacaagagagttgagcccaaatcttgtgacaaaactcacacatgcccaccgtgcccagcacctgaactcctg gggggaccgtcagtcttcctcttccccccaaaacccaaggacaccctcatgatctcccggacccctgaggtcacatgcgtggtggtgg acgtgagccacgaagaccctgaggtcaagttcaactggtacgtggacggcgtggaggtgcataatgccaagacaaagccgcggga ggagcagtacaacagcacgtaccgtgtggtcagcgtcctcaccgtcctgcaccaggactggctgaatggcaaggagtacaagtgcaa ggtctccaacaaagccctcccagcccccatcgagaaaaccatctccaaagccaaagggcagccccgagaaccacaggtgtacaccc tgcccccatcccgggaggagatgaccaagaaccaggtcagcctgacctgcctggtcaaaggcttctatcccagcgacatcgccgtgg agtgggagagcaatgggcagccggagaacaactacaagaccacgcctcccgtgctggactccgacggctccttcttcctctatagca agctcaccgtggacaagagcaggtggcagcaggggaacgtcttctcatgctccgtgatgcatgaggctctgcacaaccactacacgc agaagagcctctccctgtctccgggtaag DNA ENCODING MEPOLIZUMAB FULL LENGTH LIGHT CHAIN                            SEQ ID NO: 14 gatatcgtgatgacccagtctccagactcgctagctgtgtctctgggcgagagggccaccatcaactgcaagagctctcagagtctgtt aaacagtggaaatcaaaagaactacttggcctggtatcagcagaaacccgggcagcctcctaagagctcatttacggggcgtcgacta -continued gggaatctggggtacctgaccgattcagtggcagcgggtctgggacagatttcactctcaccatcagcagcctgcaggctgaagatgt ggcagtatactactgtcagaatgttcatagattccattcacgttcggcggagggaccaagaggagatcaaacgtactgtggcggcgcc atctgtcttcatcacccgccatctgatgagcagttgaaatctggaactgcctctgagtgtgcctgctgataacttctatcccagagaggc caaagtacagtggaaggtggataacgccctccaatcgggtaactcccaggagagtgtcacagagcaggacagcaaggacagcacct acagcctcagcagcaccctgacgctgagcaaagcagactacgagaaacacaaagtctacgcctgcgaagtcacccatcagggcctg agctcgcccgtcacaaagagcttcaacaggggagagtgt The present invention now being fully described, it will be apparent to one of ordinary skill in the art that many changes and modifications can be made thereto without departing from the spirit or scope of the appended claims.

What is claimed is:

1. A formulation comprising:
   a) an anti-IL-5 antibody composition comprising: a first antibody comprising the heavy chain amino acid sequence of SEQ ID NO: 1 and the light chain amino acid sequence of SEQ ID NO: 2; and a second antibody comprising the heavy chain amino acid sequence of SEQ ID NO: 1 and the light chain amino acid sequence of SEQ ID NO: 2, except that residue 31 of SEQ ID NO: 2 is replaced with an aspartic acid or an iso-aspartic acid, wherein the composition comprises from 3.3% to 25% of the second antibody; and
   b) one or a combination of:
      i. a buffering agent selected from the group consisting of sodium phosphate dibasic heptahydrate, phosphate, citrate, sodium phosphate, potassium phosphate, sodium citrate, and histidine, providing a pH of between 6.8 and 7.2 or a pH of between 6.2 and 6.6;
      ii. a sugar;
      iii. polysorbate 80; or
      iv. EDTA.

2. The formulation of claim 1, wherein the composition comprises from 3.3% to 20%, 3.3% to 15%, 3.3% to 12.5%, or 3.3% to 10% of the second antibody.

3. The formulation of claim 1, wherein antibody in the composition is at a concentration of between 75 mg/mL to 100 mg/mL.

4. The formulation of claim 1, wherein greater than 50% of the heavy chain C-terminal lysine residue K449 of SEQ ID NO:1 of the composition is deleted.

5. The formulation of claim 1, wherein greater than 50% of the heavy chain N-terminal glutamate of SEQ ID NO:1 of the composition is converted to pyro-glutamate.

6. The formulation of claim 1, wherein from 0% to 55% of residue M64 of SEQ ID NO: 1 of the composition is oxidized and from 0% to 3% of residue W52 of SEQ ID NO: 1 of the composition is oxidized.

7. The formulation of claim 1, wherein from 0% to 55% of residue M64 of SEQ ID NO:1 of the composition is oxidized, from 0% to 55% of residue M254 of SEQ ID NO:1 of the composition is oxidized, from 0% to 55% of residue M360 of SEQ ID NO:1 of the composition is oxidized, from 0% to 55% of residue M430 of SEQ ID NO:1 of the composition is oxidized, and from 0% to 3% of residue W52 of SEQ ID NO:1 of the composition is oxidized.

8. The formulation of claim 1, wherein from 0% to 35% of residue 386 of SEQ ID NO: 1 of the composition is replaced with an aspartic acid or an iso-aspartic acid.

9. The formulation of claim 1, wherein the composition comprises upto 80% acidic antibody variants.

10. The formulation of claim 1, wherein the composition comprises upto 20% aggregated antibodies.

11. The formulation of claim 1, wherein the composition has at least 0.70 IL-5 specific antigen binding activity compared with a reference standard composition, the reference standard composition comprising:
    a) an antibody having a heavy chain amino acid sequence of SEQ ID NO: 1 and a light chain amino acid sequence of SEQ ID NO:2;
    b) 98% or more heavy chain C-terminal lysine deleted variant of the antibody;
    c) 95% or more heavy chain N-terminal pyroglutamate variant of the antibody;
    d) 6% or less of the antibody wherein residue 31 of SEQ ID NO:2 is replaced with an aspartic acid or an iso-aspartic acid;
    e) 4% or less methionine or cysteine oxidated variant;
    f) 0.1% or less tryptophan oxidated variant; and
    g) 0.4% or less aggregated antibody variant.

12. The formulation of claim 1, wherein the buffering agent is present in the range from 10-30 mM.

13. The formulation of claim 1, wherein the sugar is sucrose and is present at a concentration of 5-20% weight by volume.

14. The formulation of claim 1, wherein the polysorbate 80 is present at a concentration of 0.01% to 0.1% weight by volume.

15. The formulation of claim 1, wherein the formulation comprises:
    a) 100 mg/ml antibody;
    b) 15.5 mM sodium phosphate dibasic heptahydrate and 4.5 mM citric acid monohydrate at pH 6.3;
    c) 12% weight of sucrose to volume;
    d) 0.02% weight of polysorbate 80 to volume, and
    a) 0.05 mM EDTA.

16. The formulation of claim 1, wherein the formulation is lyophilized and comprises:
    a) 100 mg/mL antibody;
    b) 20 mM sodium phosphate dibasic heptahydrate at pH about 6.8 to about 7.2;
    c) 12% weight of sucrose to volume; and
    d) 0.05% weight of polysorbate 80 to volume.

17. The formulation of claim 1, wherein the EDTA is present at a concentration of 0.01 mM to 0.1 mM.

* * * * *

SEQUENCE LISTING

<160> NUMBER OF SEQ ID NOS: 14

<210> SEQ ID NO 1
<211> LENGTH: 449
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 1

```
Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Thr Ser Tyr
            20                  25                  30

Ser Val His Trp Val Arg Gln Pro Pro Gly Lys Gly Leu Glu Trp Leu
        35                  40                  45

Gly Val Ile Trp Ala Ser Gly Gly Thr Asp Tyr Asn Ser Ala Leu Met
    50                  55                  60

Ser Arg Leu Ser Ile Ser Lys Asp Thr Ser Arg Asn Gln Val Val Leu
65                  70                  75                  80

Thr Met Thr Asn Met Asp Pro Val Asp Thr Ala Thr Tyr Tyr Cys Ala
                85                  90                  95

Arg Asp Pro Pro Ser Ser Leu Leu Arg Leu Asp Tyr Trp Gly Arg Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
```

```
            245                 250                 255
Arg Thr Pro Glu Val Thr Cys Val Val Asp Val Ser His Glu Asp
            260                 265                 270

Pro Glu Val Lys Phe Asn Trp Tyr Val Asp Gly Val Glu Val His Asn
            275                 280             285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
        435                 440                 445

Lys

<210> SEQ ID NO 2
<211> LENGTH: 220
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 2

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Val His Ser Phe Pro Phe Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
```

```
                   145                 150                 155                 160
Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
        210                 215                 220

<210> SEQ ID NO 3
<211> LENGTH: 119
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 3

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Thr Ser Tyr
            20                  25                  30

Ser Val His Trp Val Arg Gln Pro Pro Gly Lys Gly Leu Glu Trp Leu
        35                  40                  45

Gly Val Ile Trp Ala Ser Gly Gly Thr Asp Tyr Asn Ser Ala Leu Met
    50                  55                  60

Ser Arg Leu Ser Ile Ser Lys Asp Thr Ser Arg Asn Gln Val Val Leu
65                  70                  75                  80

Thr Met Thr Asn Met Asp Pro Val Asp Thr Ala Thr Tyr Tyr Cys Ala
                85                  90                  95

Arg Asp Pro Pro Ser Ser Leu Leu Arg Leu Asp Tyr Trp Gly Arg Gly
            100                 105                 110

Thr Pro Val Thr Val Ser Ser
        115

<210> SEQ ID NO 4
<211> LENGTH: 113
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 4

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Val His Ser Phe Pro Phe Thr Phe Gly Gly Gly Thr Lys Leu Glu Ile
```

```
              100                 105                 110
Lys

<210> SEQ ID NO 5
<211> LENGTH: 5
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 5

Ser Tyr Ser Val His
1               5

<210> SEQ ID NO 6
<211> LENGTH: 16
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 6

Val Ile Trp Ala Ser Gly Gly Thr Asp Tyr Asn Ser Ala Leu Met Ser
1               5                  10                  15

<210> SEQ ID NO 7
<211> LENGTH: 11
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 7

Asp Pro Pro Ser Ser Leu Leu Arg Leu Asp Tyr
1               5                  10

<210> SEQ ID NO 8
<211> LENGTH: 17
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 8

Lys Ser Ser Gln Ser Leu Leu Asn Ser Gly Asn Gln Lys Asn Tyr Leu
1               5                  10                  15
Ala

<210> SEQ ID NO 9
<211> LENGTH: 7
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 9

Gly Ala Ser Thr Arg Glu Ser
1               5

<210> SEQ ID NO 10
<211> LENGTH: 9
```

```
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 10

Gln Asn Val His Ser Phe Pro Phe Thr
1               5

<210> SEQ ID NO 11
<211> LENGTH: 115
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 11

Ile Pro Thr Glu Ile Pro Thr Ser Ala Leu Val Lys Glu Thr Leu Ala
1               5                   10                  15

Leu Leu Ser Thr His Arg Thr Leu Leu Ile Ala Asn Glu Thr Leu Arg
            20                  25                  30

Ile Pro Val Pro Val His Lys Asn His Gln Leu Cys Thr Glu Glu Ile
        35                  40                  45

Phe Gln Gly Ile Gly Thr Leu Glu Ser Gln Thr Val Gln Gly Gly Thr
    50                  55                  60

Val Glu Arg Leu Phe Lys Asn Leu Ser Leu Ile Lys Lys Tyr Ile Asp
65                  70                  75                  80

Gly Gln Lys Lys Lys Cys Gly Glu Glu Arg Arg Arg Val Asn Gln Phe
                85                  90                  95

Leu Asp Tyr Leu Gln Glu Phe Leu Gly Val Met Asn Thr Glu Trp Ile
            100                 105                 110

Ile Glu Ser
        115

<210> SEQ ID NO 12
<211> LENGTH: 400
<212> TYPE: PRT
<213> ORGANISM: Artificial Sequence
<220> FEATURE:
<223> OTHER INFORMATION: Amino acid sequence identified using molecular
      biology techniques.

<400> SEQUENCE: 12

Asp Leu Leu Pro Asp Glu Lys Ile Ser Leu Leu Pro Pro Val Asn Phe
1               5                   10                  15

Thr Ile Lys Val Thr Gly Leu Ala Gln Val Leu Leu Gln Trp Lys Pro
            20                  25                  30

Asn Pro Asp Gln Glu Gln Arg Asn Val Asn Leu Glu Tyr Gln Val Lys
        35                  40                  45

Ile Asn Ala Pro Lys Glu Asp Asp Tyr Glu Thr Arg Ile Thr Glu Ser
    50                  55                  60

Lys Cys Val Thr Ile Leu His Lys Gly Phe Ser Ala Ser Val Arg Thr
65                  70                  75                  80

Ile Leu Gln Asn Asp His Ser Leu Leu Ala Ser Ser Trp Ala Ser Ala
                85                  90                  95

Glu Leu His Ala Pro Pro Gly Ser Pro Gly Thr Ser Ile Val Asn Leu
            100                 105                 110

Thr Cys Thr Thr Asn Thr Thr Glu Asp Asn Tyr Ser Arg Leu Arg Ser
```

```
            115                 120                 125
Tyr Gln Val Ser Leu His Cys Thr Trp Leu Val Gly Thr Asp Ala Pro
    130                 135                 140

Glu Asp Thr Gln Tyr Phe Leu Tyr Tyr Arg Tyr Gly Ser Trp Thr Glu
145                 150                 155                 160

Glu Cys Gln Glu Tyr Ser Lys Asp Thr Leu Gly Arg Asn Ile Ala Cys
                165                 170                 175

Trp Phe Pro Arg Thr Phe Ile Leu Ser Lys Gly Arg Asp Trp Leu Ala
            180                 185                 190

Val Leu Val Asn Gly Ser Ser Lys His Ser Ala Ile Arg Pro Phe Asp
        195                 200                 205

Gln Leu Phe Ala Leu His Ala Ile Asp Gln Ile Asn Pro Pro Leu Asn
    210                 215                 220

Val Thr Ala Glu Ile Glu Gly Thr Arg Leu Ser Ile Gln Trp Glu Lys
225                 230                 235                 240

Pro Val Ser Ala Phe Pro Ile His Cys Phe Asp Tyr Glu Val Lys Ile
                245                 250                 255

His Asn Thr Arg Asn Gly Tyr Leu Gln Ile Glu Lys Leu Met Thr Asn
            260                 265                 270

Ala Phe Ile Ser Ile Ile Asp Asp Leu Ser Lys Tyr Asp Val Gln Val
        275                 280                 285

Arg Ala Ala Val Ser Ser Met Cys Arg Glu Ala Gly Leu Trp Ser Glu
    290                 295                 300

Trp Ser Gln Pro Ile Tyr Val Gly Asn Asp Glu His Lys Pro Leu Arg
305                 310                 315                 320

Glu Trp Phe Val Ile Val Ile Met Ala Thr Ile Cys Phe Ile Leu Leu
                325                 330                 335

Ile Leu Ser Leu Ile Cys Lys Ile Cys His Leu Trp Ile Lys Leu Phe
            340                 345                 350

Pro Pro Ile Pro Ala Pro Lys Ser Asn Ile Lys Asp Leu Phe Val Thr
        355                 360                 365

Thr Asn Tyr Glu Lys Ala Gly Ser Ser Glu Thr Glu Ile Glu Val Ile
    370                 375                 380

Cys Tyr Ile Glu Lys Pro Gly Val Glu Thr Leu Glu Asp Ser Val Phe
385                 390                 395                 400

<210> SEQ ID NO 13
<211> LENGTH: 1347
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 13
caggttaccc tgcgtgaatc cggtccggca ctagttaaac cgacccagac cctgacgtta      60
acctgcaccg tctccggttt ctccctgacg agctatagtg tacactgggt ccgtcagccg     120
ccgggtaaag gtctagaatg gctgggtgta atatgggcta gtggaggcac agattataat     180
tcggctctca tgtcccgtct gtcgatatcc aaagacacct cccgtaacca ggttgttctg     240
accatgacta catggacccg gttgacaccg ctacctact actgcgctcg agatccccct      300
tcttccttac tacggcttga ctactggggt cgtggtaccc agttaccgt gagctcagct      360 agtaccaagg gcccatcggt cttccccctg gcaccctcct ccaagagcac ctctgggggc     420
acagcggccc tgggctgcct ggtcaaggac tacttccccg aaccggtgac ggtgtcgtgg     480
```

```
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagagagt tgagcccaaa    660
tcttgtgaca aaactcacac atgcccaccg tgcccagcac ctgaactcct ggggggaccg    720
tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020 gccaagggc  agccccgaga  ccacaggtg  tacaccctgc ccccatcccg ggaggagatg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctatagc aagctcaccg tggacaagag caggtggcag   1260
caggggaacg tcttctcatg ctccgtgatg catgaggctc tgcacaacca ctacacgcag   1320
aagagcctct ccctgtctcc gggtaag                                       1347

<210> SEQ ID NO 14
<211> LENGTH: 660
<212> TYPE: DNA
<213> ORGANISM: Artificial Sequence
<220> FEATURE:
<223> OTHER INFORMATION: Nucleic acid sequence identified using
      molecular biology techniques.

<400> SEQUENCE: 14
gatatcgtga tgacccagtc tccagactcg ctagctgtgt ctctgggcga gagggccacc     60
atcaactgca gagctctca gagtctgtta aacagtggaa atcaaaagaa ctacttggcc    120
tggtatcagc agaaacccgg gcagcctcct aagttgctca tttacggggc gtcgactagg    180
gaatctgggg tacctgaccg attcagtggc agcgggtctg ggacagattt cactctcacc    240
atcagcagcc tgcaggctga agatgtggca gtatactact gtcagaatgt tcatagtttt    300
ccattcacgt tcggcggagg gaccaagttg gagatcaaac gtactgtggc ggcgccatct    360
gtcttcatct tcccgccatc tgatgagcag ttgaaatctg gaactgcctc tgttgtgtgc    420
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gcttcaacag gggagagtgt    660
```